US010300152B2

(12) United States Patent
Ortac et al.

(10) Patent No.: US 10,300,152 B2
(45) Date of Patent: May 28, 2019

(54) ENZYME-ENCAPSULATED NANOPARTICLE PLATFORM

(71) Applicants: The Regents of the University of California, Oakland, CA (US); DevaCell, Inc., San Diego, CA (US)

(72) Inventors: Inanc Ortac, San Diego, CA (US); Sadik C. Esener, Solana Beach, CA (US); Ibrahim Gokce Yayla, Del Mar, CA (US); Bradley Messmer, San Diego, CA (US)

(73) Assignees: The Regents of the University of California, Oakland, CA (US); Devacell, Inc., San Diego, CA (US)

( * ) Notice: Subject to any disclaimer, the term of this patent is extended or adjusted under 35 U.S.C. 154(b) by 211 days.

(21) Appl. No.: 15/022,551

(22) PCT Filed: Sep. 17, 2014

(86) PCT No.: PCT/US2014/056179
§ 371 (c)(1),
(2) Date: Mar. 16, 2016

(87) PCT Pub. No.: WO2015/042204
PCT Pub. Date: Mar. 26, 2015

(65) Prior Publication Data
US 2016/0243262 A1 Aug. 25, 2016

Related U.S. Application Data

(60) Provisional application No. 61/879,120, filed on Sep. 17, 2013.

(51) Int. Cl.
| A61B 5/00 | (2006.01) |
| A61K 9/51 | (2006.01) |
| C12Q 1/00 | (2006.01) |
| C12Q 1/30 | (2006.01) |
| C12Q 1/54 | (2006.01) |
| A61B 5/145 | (2006.01) |
| A61K 38/50 | (2006.01) |
| A61K 49/00 | (2006.01) |
| A61K 49/22 | (2006.01) |
| A61B 5/1455 | (2006.01) |

(52) U.S. Cl.
CPC ........ *A61K 49/0093* (2013.01); *A61B 5/1455* (2013.01); *A61B 5/14532* (2013.01); *A61B 5/6831* (2013.01); *A61B 5/7278* (2013.01); *A61K 9/5115* (2013.01); *A61K 49/225* (2013.01); *C12Q 1/00* (2013.01); *C12Q 1/30* (2013.01); *C12Q 1/54* (2013.01); *A61B 2503/40* (2013.01); *A61K 38/50* (2013.01)

(58) Field of Classification Search
None
See application file for complete search history.

(56) References Cited

U.S. PATENT DOCUMENTS

| 2003/0099574 A1 | 5/2003 | Bentsen et al. |
| 2004/0013728 A1 | 1/2004 | Oh et al. |
| 2010/0209354 A1 | 8/2010 | Horcajada-Cortes et al. |
| 2011/0002978 A1 | 1/2011 | Harrison |
| 2013/0006079 A1 | 1/2013 | Feldman et al. |

FOREIGN PATENT DOCUMENTS

| WO | 2011060129 A1 | 5/2011 |
| WO | WO-2012142625 A2 | 10/2012 |

OTHER PUBLICATIONS

Parrish et al.,Therapeutic Uses of Light, Ann N.Y. Acad. Sci., 453: 354-364 (1985) (Year: 1985).*
Rolinski et al.,"A time-resolved near-infrared fluorescence assay for glucose: opportunities for trans-dermal sensing", J. Photochem. Photobiol. B: Biol. 54: 26-34 (2000) (Year: 2000).*
Gius, et al., . Redox signaling in cancer biology. Antioxidants & Redox Signaling, 8(7-8):1249-1252, Jul. 2006.
Glasfeld, Arthur, Biochemistry: The chemical reactions of living cells, 2nd edition (david e. metzler). Journal of Chemical Education, 81(5):646, May 2004.
Goseki, et al., Synergistic effect of methionine-depleting total parenteral nutrition with 5-fluorouracil on human gastric cancer: a randomized, prospective clinical trial. Japanese journal of cancer research: Gann, 86(5):484-489, May 1995. PMID: 7790321.
Graham, Michael L., Pegaspargase: a review of clinical studies. Advanced drug delivery reviews, 55(10):1293-1302, Sep. 2003. PMID: 14499708.
Guo, et al., Facile synthesis of hierarchically mesoporous silica particles with controllable cavity in their surfaces. Langmuir, 26(2):702-708, 2009.
Gutiérrez Millán, et al., Factors associated with the performance of carrier erythrocytes obtained by hypotonic lialysis. Blood Cells, Molecules, and Diseases, 33(2):132-140, Sep. 2004.
Gutierrez Millán, et al., Drug, enzyme and peptide delivery using erythrocytes as carriers. Journal of Controlled Release, 95(1):27-49, Feb. 2004.

(Continued)

*Primary Examiner* — Anand U Desai
(74) *Attorney, Agent, or Firm* — Perkins Coie LLP

(57) ABSTRACT

Disclosed are methods, systems, and devices for implementing nanoparticles to encapsulate biomolecules such as enzymes. In one aspect, a nanoparticle device includes a shell structure including an internal layer structured to enclose a hollow interior region and include one or more holes penetrating through the internal layer, and an external layer formed of a porous material around the internal layer; and an enzyme contained within the interior region of the shell structure, the enzyme having entered the shell structure through the one or more holes and incapable of passing through the external layer, in which the pores are of a size that prevents the enzyme to pass through the pores while permitting substances smaller than the pore size to pass through the pores.

20 Claims, 17 Drawing Sheets

(56) References Cited

OTHER PUBLICATIONS

Hamidi, et al, Applications of carrier erythrocytes in delivery of biopharmaceuticals. 118(2):145-160, Apr. 2007. Journal of Controlled Release.
Hansen, et al., Arylboronic acids: A diabetic eye on glucose sensing. Sensors and Actuators B: Chemical, 161(1):45-79, Jan. 2012.
Hentze, et al., Silica hollow spheres by templating of catanionic vesicles. Society, 19(11):1069-1074, 2003.
Hoff, et al., Oscillations of polymeric microbubbles: effect of the encapsulating shell. The Journal of the Acoustical Society of America, 107(4):2272-80, 2000.
Hori, et al., Methylthioadenosine phosphorylase cDNA transfection alters sensitivity to depletion of purine and methionine in a549 lung cancer cells. Cancer research, 56(24):5653-5658, Dec. 1996. PMID: 8971171.
Hori, et al.,Gene cloning and characterization of pseudomonas putida I-methionine-alpha-deamino-gamma-mercaptomethanelyase. Cancer research, 56(9):2116-2122, May 1996. PMID: 8616859.
Hu, et al., Methionine depletion with recombinant methioninase: in vitro and in vivo efficacy against neuroblastoma and its synergism with chemotherapeutic drugs. International journal of cancer. Journal international du cancer, 124(7):1700-1706, Apr. 2009. PMID: 19089915.
Huennekens, Tumor targeting: Activation of prodrugs by enzyme-monoclonal antibody conjugates. Trends in Biotechnology, 12(6):234-239, Jun. 1994.
Im, et al., Polymer hollow particles with controllable holes in their surfaces. Nat Mater, 4(9):671-675, 2005.
Ishimoto, et al., Single-cell observation of phagocytosis by human blood dendritic cells. Japanese journal of infectious diseases, 61(4):294-297, Jul. 2008. PMID: 18653972.
Ivanova, et al., Comparative kinetic study of d-glucose oxidation by ruthenium(III) compounds catalyzed by FAD-Dependent glucose oxidase and PQQ-Dependent glucose dehydrogenase. Biochemistry (Moscow), 68(4):407-415, Apr. 2003.
Johansson, et al., IdeS: a bacterial proteolytic enzyme with therapeutic potential. PLoS ONE, 3(2):e1692, Feb. 2008.
Jokerst, et al., Nanoparticle PEGylation for imaging and therapy. Nanomedicine, 6(4):715-728, Jun. 2011.
Khanna, et al., 2012 American College of Rheumatology Guidelines for Management of Gout. Part 1: Systematic Nonpharmacologic and Pharmacologic Therapeutic Approaches to Hyperuricemia. Arthritis care & research, 64(10):1431-1446, Oct. 2012. PMID: 23024028.
Khanna, et al., 2012 American College of Rheumatology Guidelines for Management of Gout. Part 2: Therapy and Antiinflammatory Prophylaxis of Acute Gouty Arthritis. Arthritis Care & Research, 64(10):1447-1461, Oct. 2012. PMID: 23024029.
Kiernan, et al., Ruthenium-doped sol-gel derived silica films: Oxygen sensitivity of optical decay times. Journal of Sol-Gel Science and Technology, 2(1-3):513-517, Jan. 1994.
Killander, et al., Hyper-sensitive reactions and antibody formation during I-asparaginase treatment of children and adults with acute leukemia. Cancer, 37(1):220-228, Jan. 1976. PMID: 1061636.
Kim, et al., Intestinal goblet cells and mucins in health and disease: recent insights and progress. Current gastroenterology reports, 12(5):319-330, Oct. 2010. PMID: 20703838.
Kim, et al., Nanobiocatalysis and its potential applications. Trends in biotechnology, 26(11):639-646, Nov. 2008. PMID: 18804884.
Kim, et al., Single-enzyme nanoparticles armored by a nanometer-scale Organic/Inorganic network. Nano Letters, 3(9):1219-1222, Sep. 2003.
Kim, et al., The regulation of INK4/ARF in cancer and aging. Cell, 127(2):265-275, Oct. 2006.
Kim, et al.. Fabrication of hollow palladium spheres and their successful application to the recyclable heterogeneous catalyst for Suzuki coupling reactions. J. Am. Chem. Soc., 124(26):7642-7643, 2002.
Klibanov, et al., Detection of individual microbubbles of an ultrasound contrast agent: fundamental and pulse inversion imaging. Academic radiology, 9 Suppl 2:S279-81, 2002.
Knoderer, et al., Predicting asparaginase-associated pancreatitis. Pediatric blood & cancer, 49(5):634-639, Oct. 2007. PMID: 16937362.
Kravtzoff, et al., Improved pharmacodynamics of I-asparaginase-loaded in human red blood cells. European Journal of clinical pharmacology, 49(6):465-470, 1996. PMID: 8706771.
Kumar, et al., Hollow gold nanoparticles encapsulating horseradish peroxidase. Biomaterials, 26(33):6743-6753, Nov. 2005. PMID: 15951014.
Kyriakidis, et al., Antiproliferative activity of I-asparaginase of tetrahymena pyriformis on human breast cancer cell lines. Molecular and cellular biochemistry, 96(2):137-142, Aug. 1990. PMID: 2125695.
Lee, et al., In vivo imaging of hydrogen peroxide with chemiluminescent nanoparticles. Nature Materials, 6(10):765-769, Oct. 2007.
Lichtenstein, et al., The role of basophils in inflammatory reactions. The Journal of investigative dermatology, 71(1):65-69, Jul. 1978. PMID: 79620.
Lippert, et al., A hydrogen peroxide-responsive hyperpolarized 13C MRI contrast agent. Journal of the American Chemical Society, 133(11):3776-3779, Mar. 2011.
Liu, et al., From hollow nanosphere to hollow microsphere: Mild buffer provides easy access to tunable silica structure. J. Phys. Chem. C, 112(42):16445-16451, 2008.
Ma, et al., Solution-phase synthesis of inorganic hollow structures by templating strategies. Journal of Colloid and Interface Science, 335(1):1-10, Jul. 2009.
Ma, et al., Ultrasmall sub-10 nm near-infrared fluorescent mesoporous silica nanoparticles. Journal of the American Chemical Society, 134(32):13180-13183, Aug. 2012.
MacDonald, et al., Hybrid nanoscale inorganic cages. Nature Materials, 9:810-815, Sep. 2010.
Marinakos, et al., Gold particles as templates for the synthesis of hollow polymer capsules. control of capsule dimensions and guest encapsulation. J. Am. Chem. Soc., 121(37):8518-8522, 1999.
Müller, et al., Use of I-asparaginase in childhood ALL. Critical Reviews in Oncology/Hematology, 28(2):97-113, Aug. 1998.
Nachman, et al., Augmented berlin-frankfurt-munster therapy abrogates the adverse prognostic significance of slow early response to induction chemotherapy for children and adolescents with acute lymphoblastic leukemia and unfavorable presenting features: a report from the children's cancer group. Journal of clinical oncology: official journal of the American Society of Clinical Oncology,15(6):2222-2230, Jun. 1997. PMID: 9196134.
Nachman, et al., Augmented post-induction therapy for children with high-risk acute lymphoblastic leukemia and a slow response to initial therapy. New England Journal of Medicine, 338(23):1663-1671, 1998. PMID: 9614257.
Napierska, et al., The nanosilica hazard: another variable entity. Particle and Fibre Toxicology, 7(1):39, 2010. PMID: 21126379.
Ni, et al., Arginine deiminase, a potential anti-tumor drug. Cancer letters, 261(1):1-11, Mar. 2008. PMID: 18179862.
Nichols, et al., Biocompatible materials for continuous glucose monitoring devices. Chemical Reviews, 113(4):2528-2549, Apr. 2013.
Nobori, et al., Genomic cloning of methylthioadenosine phosphorylase: a purine metabolic enzyme deficient in multiple different cancers. Proceedings of the National Academy of Sciences of the United States of America, 93(12):6203-6208, Jun. 1996. PMID: 8650244.
Nowak-Göttl, et al., Changes in coagulation and fibrinolysis in childhood acute lymphoblastic leukaemia re-induction therapy using three different asparaginase preparations. European journal of pediatrics, 156(11):848-850, Nov. 1997. PMID: 9392397.
Oh, et al., Cellular uptake, cytotoxicity, and innate immune response of Silica Titania hollow nanoparticles based on size and surface functionality. ACS Nano, 4(9):5301-5313, Sep. 2010.
Ohnuma, et al., Effects of I-asparaginase in acute myelocytic leukemia. JAMA, 210(10):1919-1921, Dec. 1969.
Oliver, et al., Glucose sensors: a review of current and emerging technology. Diabetic Medicine, 26(3):197-210, 2009.
Ollenschläger et al., Asparaginase-induced derangements of glutamine metabolism: the pathogenetic basis for some drug-related

(56) References Cited

OTHER PUBLICATIONS side-effects. European journal of clinical investigation, 18(5):512-516, Oct. 1988. PMID: 3147904.
Olson, et al., Toward in vivo detection of hydrogen peroxide with ultrasound molecular imaging. Biomaterials, 34(35):8918-8924, Nov. 2013.
Ortac, et al., "Nanoparticle Encapsulated L-Asparaginase," Blood (55th Annual Meeting of the American Society of Hematology, Dec. 7-10, 2013, New Orleans, LA, Nov. 1, 2013, p. 2669.
Ortega, et al., L-asparaginase, vincristine, and prednisone for induction of first remission in acute lymphocytic leukemia. Cancer Research, 37(2):535-540, Feb. 1977.
Ow, et al., Bright and stable Core Shell fluorescent silica nanoparticles. Nano Letters, 5(1):113-117, Jan. 2005.
Pan, et al., A novel synthesis of micrometer silica hollow sphere. Materials Research Bulletin, 44(2):280-283, Feb. 2009.
Patterson, et al., "Nanoreactors by Programmed Enzyme Encapsulation Inside the Capsid of the Bactiophase P22," ACS NANO (American Chemical Society), vol. 6, No. 6, Jun. 26, 2012.
Pavillard, et al., Methionine dependence of tumours: A biochemical strategy for optimizing paclitaxel chemosensitivity in vitro. Biochemical Pharmacology, 71(6):772-778, Mar. 2006.
Pession, Andrea, First-line treatment of acute lymphoblastic leukemia with pegasparaginase. Biologics: Targets & Therapy, p. 359, Jul. 2009.
Petrovsky, et al., Vaccine adjuvants: Current state and future trends. Immunology and Cell Biology, 82(5):488-496, Sep. 2004.
Pickup, et al., In vivo glucose monitoring: the clinical reality and the promise. Biosensors and Bioelectronics, 20(10):1897-1902, Apr. 2005.
Pickup, et al., In vivo glucose sensing for diabetes management: progress towards non-invasive monitoring. BMJ, 319(7220):1289-1289, Nov. 1999.
Pieters, et al., L-asparaginase treatment in acute lymphoblastic leukemia. Cancer, 117(2):238-249, 2011.
Piras, et al., A new biocompatible nanoparticle delivery system for the release of fibrinolytic drugs. International Journal of Pharmaceutics, 357(1-2):260-271, Jun. 2008. PMID: 18313868.
Pohaku Mitchell, et al., Iron(III)-Doped, silica nanoshells: A biodegradable form of silica. Journal of the American Chemical Society, 134(34):13997-14003, Aug. 2012.
Popplewell, et al., Kinetics of uptake and elimination of silicic acid by a human subject: a novel application of 32Si and accelerator mass spectrometry. Journal of Inorganic Biochemistry, 69(3):177-180, Feb. 1998. PMID: 9629677.
Pui, et al., "Acute Lymphoblastic Leukemia", New England Journal of Medicine, 350(15):1535-1548, 2004. PMID: 15071128.
Radin, et al., In vitro bioactivity and degradation behavior of silica xerogels intended as controlled release materials. Biomaterials, 23(15):3113-3122, Aug. 2002.
Radin, et al., In vivo tissue response to resorbable silica xerogels as controlled-release materials. Biomaterials, 26(9):1043-1052, Mar. 2005.
Rapoport, et al., Hollow nanoparticles of WS2 as potential solid-state lubricants. Nature, 387(6635):791-793, 1997.
Reddy, et al., Nanoparticle-mediated delivery of superoxide dismutase to the brain: an effective strategy to reduce schemia-reperfusion injury. The FASEB Journal: Official Publication of the Federation of American Societies for Experimental Biology, 23(5):1384-1395, May 2009. PMID: 19124559.
Rooseboom, et al., Enzyme-catalyzed activation of anticancer prodrugs. Pharmacological Reviews, 56(1):53-102, Mar. 2004.
Rotoli et al., Inhibition of glutamine synthetase triggers apoptosis in asparaginase-resistant cells. Cellular physiology and biochemistry: international journal of experimental cellular physiology, biochemistry, and pharmacology, 15(6):281-292, 2005. PMID: 16037693.
Ryabov, et al., Redox mediation and photomechanical oscillations involving photosensitive cyclometalated ru(II) complexes, glucose oxidase, and peroxidase. Analytical chemistry, 77(4):1132-1139, Feb. 2005. PMID: 15858996.

Ryabov, et al., Spectrophotometric kinetic study and analytical implications of the glucose oxidase-catalyzed reduction of [MIII(LL)2CI2]+ complexes by d-glucose (M=Os and ru, LL=2,2-bipyridine and 1,10-phenanthroline type ligands). JBIC Journal of Biological Inorganic Chemistry, 4(2):175-182, May 1999.
Salzer, et al., Erwinia asparaginase achieves therapeutic activity after pegaspargase allergy: a report from the children's oncology group. Blood, Jun. 2013. PMID: 23741010.
Sato, et al., Methionine gamma-lyase: the unique reaction mechanism, physiological roles, and therapeutic applications against infectious diseases and cancers. IUBMB life, 61(11):1019-1028, Nov. 2009. PMID: 19859976.
Schalkwijk et al., An experimental model for hydrogen peroxide-induced tissue damage. effects of a single inflammatory mediator on (peri)articular tissues. Arthritis and rheumatism, 29(4):532-8, 1986.
Sherman, et al., PEG-uricase in the management of treatment-resistant gout and hyperuricemia. Advanced Drug Delivery Reviews, 60(1):59-68, Jan. 2008.
Skrabalak, et al., Facile synthesis of ag nanocubes and au nanocages. Nat. Protocols, 2(9):2182-2190, 2007.
Slezak, et al., Hydrogen peroxide changes in ischemic and reperfused heart. cytochemistry and biochemical and ray microanalysis. The American journal of pathology, 147(3):772-81, 1995.
Slowing, et al., Mesoporous silica nanoparticles as controlled release drug delivery and gene transfection carriers. Advanced Drug Delivery Reviews, 60(11):1278-1288, Aug. 2008.
Sokolov, et al., Novel fluorescent silica nanoparticles: Towards ultrabright silica nanoparticles. Small, 4(7):934-939, Jul. 2008.
Stone, J. R., An assessment of proposed mechanisms for sensing hydrogen peroxide in mammalian systems. Archives of Biochemistry and Biophysics, 422(2):119-124, Feb. 2004.
Story, et al., L-asparaginase kills lymphoma cells by apoptosis. Cancer chemotherapy and pharmacology, 32(2):129-133, 1993. PMID: 8485807.
Sun, et al., In vivo efficacy of recombinant methioninase is enhanced by the combination of polyethylene glycol conjugation and pyridoxal 5'-phosphate supplementation. Cancer research, 63(23):8377-8383, Dec. 2003. PMID: 14678999.
Sundy, et al., Efficacy and tolerability of pegloticase for the treatment of chronic gout in patients refractory to conventional treatment: two randomized controlled trials. JAMA: the journal of the American Medical Association, 306(7):711-720, Aug. 2011. PMID: 21846852.
Sundy, et al., Uricase and other novel agents for the management of patients with treatment-failure gout. Current rheumatology reports, 9(3):258-264, Jun. 2007. PMID: 17531181.
Swartz, Melody A., The physiology of the lymphatic system. Advanced Drug Delivery Reviews, 50(1-2):3-20, Aug. 2001.
Szatrowski, et al., Production of large amounts of hydrogen peroxide by human tumor cells. Cancer Research, 51(3):794-798, Feb. 1991. PMID: 1846317.
Tan, et al., Broad selective efficacy of recombinant methioninase and polyethylene glycol-modified recombinant methioninase on cancer cells in vitro. Anticancer research, 30(4):1041-1046, Apr. 2010. PMID: 20530407.
Tang, et al., Increasing the therapeutic index of 5-fluorouracil and 6-thioguanine by targeting loss of MTAP in tumor mils. Cancer biology & therapy, 13(11):1082-1090, Sep. 2012. PMID: 22825330.
Tasciotti, et al., Mesoporous silicon particles as a multistage delivery system for imaging and therapeutic applications. Nat Nano, 3(3)151-157, Mar. 2008.
Taylor, et al., A phase i and pharmacodynamic evaluation of polyethylene glycol-conjugated l-asparaginase in patients with advanced solid tumors. Cancer Chemotherapy and Pharmacology, 47(1):83-88, Jan. 2001.
Terkeltaub, R. A., Clinical practice. gout. The New England journal of medicine, 349(17):1647-1655, Oct. 2003. PMID: 14573737.
Terkeltaub, R., Learning how and when to employ uricase as bridge therapy in refractory gout. The Journal of rheumatology, 34(10):1955-1958, Oct. 2007. PMID: 17924606.
Tonegawa, Susumu, Somatic generation of antibody diversity. Nature, 302(5909):575-581, Apr. 1983.

(56) References Cited

OTHER PUBLICATIONS

Abakumova, et al., "Antitumor activity of l-asparaginase from erwinia carotovora against different human and animal leukemic and solid tumor cell lines", Biochemistry (Moscow) Supplement Series B: Biomedical Chemistry, 6(4):307-316, Oct. 2012.
Alpar, et al., "Therapeutic efficacy of asparaginase encapsulated in intact erythrocytes", Biochemical pharmacology, 34(2):257-261, Jan. 1985. PMID: 3966927.
Armogida, et al., "The protective role of catalase against cerebral ischemia in vitro and in vivo", International journal of immunopathology and pharmacology, 24(3):735-747, Dec. 2010. PMID: 21978706.
Armstrong, et al., "Antibody Against Poly(Ethylene Glycol) Adversely Affects PEG-Asparaginase Therapy in Acute Lymphoblastic Leukemia Patients", Cancer, 110(1):103-111, Jul. 2007. PMID: 17516438.
Armstrong, Jonathan K., "The occurrence, induction, specificity and potential effect of antibodies against poly (ethylene glycol)", PEGylated Protein Drugs: Basic Science and Clinical Applications, Milestones in Drug Therapy, pp. 147-168. Birkhäuser Basel, Jan. 2009.
Arnal, et al., "High-Temperature Stable Catalysts by Hollow Sphere Encapsulation", Angewandte Chemie, 118(48):8404-8407, Dec. 2006.
Ascierto, et al., "Pegylated Arginine Deiminase Treatment of Patients with Metastatic Melanoma: Results from Phase I and II Studies", Journal of Clinical Oncology, 23(30):7660-7668, Oct. 2005.
Avramis, et al., "Pharmacoanalytical Assays of Erwinia Asparaginase Eerwinase) and Pharmacokinetic Results in High-risk Acute Lymphoblastic Leukemia (HR ALL) Patients: Simulations of Erwinase Population PK-PD Models", Anticancer research, 27(4C):2561-2572, Aug. 2007. PMID: 17695416.
Bagshawe, Kenneth D., "Antibody-directed enzyme prodrug therapy (ADEPT) for cancer", Future Drugs Ltd., 2006, pp. 1421-1431.
Banchereau, et al., "Immunobiology of Dendritic Cells", Annual Review of Immunology, 18(1):767-811, 2000.
Belkaid, et al., "Natural regulatory T cells in infectious disease", Nature Immunology, 6(4):353-360, Apr. 2005.
Bertino, et al., "Targeting tumors that lack methylthioadenosine phosphorylase (MTAP) activity: current strategies", Cancer biology & therapy, 11(7):627-632, Apr. 2011.
Blanco, et al., "Large-scale synthesis of a silicon photonic crystal with a complete three-dimensional bandgapnear 1.5 micrometres", Nature, 405(6785):437-440, May 2000.
Bode, et al., "CpG DNA as a vaccine adjuvant", Expert Review of Vaccines, 10(4):499-511, Apr. 2011.
Bohney, et al., "Identification of Lys190 as the primary binding site for pyridoxal 5'-phosphate in human serum albumin", FEBS letters, 298(2-3):266-268, Feb. 1992.
Brodell et al., "Skin structure and Function: The Body's Primary Defense Against Infection", Infectious Diseases in Clinical Practice, 16(2):113-117, Mar. 2008.
Bush, et al., "Updated Functional Classification of B-lactamases", Antimicrobial Agents and Chemotherapy, 54(3):969-976, Mar. 2010.
Cai, et al., "The vascular Nad(P)H oxidases as therapeutic targets in cardiovascular diseases", Trends in Pharmacological Sciences, 24(9):471-478, Sep. 2003.
Caliceti, et al., "Pharmacokinetic and biodistribution properties of poly(ethylene glycol)—protein conjugates", Advanced Drug Delivery Reviews, 55(10):1261-1277, Sep. 2003.
Caruso, et al., "Nanoengineering of Inorganic and Hybrid Hollow Spheres by Colloidal Templating", Science, 282(5391):1111-1114, 1998.
Caruso, F., "Nanoengineering of Particle surfaces", Advanced Materials, 13(1):11-22, Jan. 2001.
Chen, et al., "Classic and contemporary approaches to modeling Biochemical reactions", Genes & development, 24(17):1861-1875, Sep. 2010.
Cheng, et al., "Efficient clearance of poly(ethylene glycol)-modified immunoenzyme with anti-PEG monoclonal antibody for prodrug cancer therapy", Bioconjugate chemistry, 11(2):258-266, Apr. 2000.
Cheong, et al., "Ammonia-induced autophagy is independent of ULK1/ULK2 kinases", Proceedings of the National Academy of Sciences, Jun. 2011.
Chiu, et al., "Enzyme-encapsulated silica nanoparticle for cancer chemotherapy," Jounal of Nanoparticle Research; An Interdisciplinary Forum for Nanoscale Science and Technology (Kluwer Academic Pblishers), vol. 14, No. 4, Mar. 31, 2012.
Cochran, Ceramic hollow spheres and their applications:, Current Opinion in Solid State and Materials Science, 3(5):474-479, 1998.
Dave, et al., "Pegloticase and the patient with treatment-failure gout", Expert Review of Clinical Pharmacology, 5(5):501-508, Sep. 2012.
Denny, William A., "Prodrug strategies in cancer therapy", European Journal of Medicinal Chemistry, 36(7-8):577-595, Aug. 2001.
Dinarello, C.A., Proinflammatory Cytokines:, Chest, 118(2):503-508, Aug. 2000.
Dinsmore, et al., "Colloidosomes: Selectively Permeable Capsules Composed of Colloidal Particles", Science, 2002, pp. 1006-1009.
Distasio, et al., Alteration in Spleen Lymphoid Populations Associated with Specific Amino Acid Depletion during L-Asparaginase Treatment:, Cancer Research, 42(1):252-258, Jan. 1982.
Distasio, et al., "Antilymphoma activity of a glutaminase-free l-asparaginase of microbial origin. Proceedings of the Society for Experimental Biology and Medicine", Society for Experimental Biology and Medicine (New York, N.Y.), 155(4):528-531, Sep. 1977.
Dobrucki, J. W., Interaction of oxygen-sensitive luminescent probes ru(phen)32+ and ru(bipy)32+ with animal and plant cells in vitro: Mechanism of phototoxicity and conditions for non-invasive oxygen measurements. Journal of Photochemistry and Photobiology B: Biology, 65(2-3):136-144, Dec. 2001.
Domenech, et al., l-asparaginase loaded red blood cells in refractory or relapsing acute lymphoblastic leukaemia in children and adults: results of the GRASPALL Jan. 2005 randomized trial. British Journal of Haematology, 153(1):58-65, 2011.
Douer, D., Is asparaginase a critical component in the treatment of acute lymphoblastic leukemia? Best Practice & Research Clinical Haematology, 21(4):647-658, Dec. 2008.
Dübbers, et al., Asparagine synthetase activity in paediatric acute leukaemias: AML-M5 subtype shows lowest activity. British Journal of Haematology, 109(2):427-429, 2000.
Dziubla, et al., Polymer nanocarriers protecting active enzyme cargo against proteolysis. Journal of Controlled Release, 102(2):427-439, Feb. 2005.
Edwards, et al., Work productivity loss due to flares in patients with chronic gout refractory to conventional therapy. Journal of medical economics, 14(1):10-15, 2011. PMID: 21138339.
El-Sayed, A. S., Microbial l-methioninase: production, molecular characterization, and therapeutic applications. Applied microbiology and biotechnology, 86(2):445-467, Mar. 2010. PMID: 20146062.
Epner, D. E., Can dietary methionine restriction increase the effectiveness of chemotherapy in treatment of advanced cancer? Journal of the American College of Nutrition, 20(5 Suppl):443S-449S; discussion 473S-475S, Oct. 2001. PMID: 11603655.
Esaki, et al., L-methionine gamma-lyase from pseudomonas putida and aeromonas. Methods in enzymology, 143:459-465, 1987. PMID: 3657560.
Fensterl, et al., Interferons and viral infections. BioFactors (Oxford, England), 35(1):14-20, Feb. 2009. PMID: 19319841.
Fleming, et al., Nanosphere Microsphere assembly: methods for Core Shell materials preparation. Chem. Mater., 13(6):2210-2216, 2001.
Fonda, et al., The binding of pyridoxal 5'-phosphate to human serum albumin. Archives of biochemistry and piophysics, 288(1):79-86, Jul. 1991. PMID: 1898027.
Fujiwara, et al., Direct encapsulation of BSA and DNA into silica microcapsules (hollow spheres). Journal of Biomedical Materials Research. Part A, 81(1):103-112, Apr. 2007. PMID: 17109429.
Gaberc-Porekar, et al., Obstacles and pitfalls in the PEGylation of therapeutic proteins. Current opinion in drug discovery & development, 11(2):242-250, Mar. 2008. PMID: 18283612.
Gaffney, et al., Hydrogen peroxide contrast echocardiography. The American Journal of Cardiology, 52(5):607-609, Sep. 1983.
Ganson, et al., Control of hyperuricemia in subjects with refractory gout, and induction of antibody against poly (ethylene glycol)

(56) References Cited

OTHER PUBLICATIONS (PEG), in a phase i trial of subcutaneous PEGylated urate oxidase. Arthritis Research & Therapy, 8(1):R12, Dec. 2005. PMID: 16356199.
Gao, et al., Novel fluorogenic substrates for imaging 6-lactamase gene expression. Journal of the American Chemical Society, 125(37):11146-11147, Sep. 2003. WOS:000185341800005.
Garay, et al., Antibodies against polyethylene glycol in healthy subjects and in patients treated with PEG-conjugated agents. Expert opinion on drug delivery, 9(11):1319-1323, Nov. 2012. PMID: 22931049.
Torney, et al., Mesoporous silica nanoparticles deliver DNA and chemicals into plants. Nat Nano, 2(5):295-300, May 2007.
Tsuji, et al., Studies on antigenicity of the polyethylene glycol (PEG)-modified uricase. International Journal of Immunopharmacology, 7(5):725-730, 1985.
Jusitalo et al., "Recent Advances in Intracellular and In Vivo ROS Sending: Focus on Nanoparticle and Nanotube Applications", International Journal of Molecular Sciences, vol. 13, No. 12, 2012, pp. 10660-10679.
Van Den Berg, H., Asparaginase revisited. Leukemia and Lymphoma, 52(2):168-178, 2011.
Van Furth, et al., The origin and kinetics of mononuclear phagocytes. The Journal of Experimental Medicine, 128(3):415-435, Sep. 1968. PMID: 5666958.
Vander Heiden, et al., Understanding the warburg effect: the metabolic requirements of cell proliferation. Science (New York, N.Y.), 324(5930):1029-1033, May 2009. PMID: 19460998.
Vashist, S. K., Non-invasive glucose monitoring technology in diabetes management: A review. Analytica Chimica Acta, 750:16-27, Oct. 2012.
Veronese, Francesco M., Peptide and protein PEGylation: a review of problems and solutions. Biomaterials, 22(5):405-417, Mar. 2001.
Volodkin, et al., Matrix polyelectrolyte microcapsules: new system for macromolecule encapsulation. Langmuir, 20(8):3398-3406, Apr. 2004.
Vrudhula, et al., Cephalosporin derivatives of doxorubicin as prodrugs for activation by monoclonal antibody-.beta.-lactamase conjugates. J. Med. Chem., 38(8):1380-1385, 1995.
Wang, et al., Enzyme encapsulation in nanoporous silica spheres. Chemical Communications, (13):1528-1529, Jun. 2004.
Wang, et al., Mesoporous silica spheres as supports for enzyme immobilization and encapsulation. Chemistry of Materials, 17(5):953-961, Mar. 2005.
Warrell, Jr., et al., Clinical evaluation of succinylated acinetobacter glutaminase-asparaginase in adult leukemia. Cancer treatment reports, 66(7):1479-1485, Jul. 1982. PMID: 7046929.
Whiting, et al., IDF diabetes atlas: Global estimates of the prevalence of diabetes for 2011 and 2030. Diabetes Research and Clinical Practice, 94(3):311-321, Dec. 2011.
Willer, et al., Anti-E. coli asparaginase antibody levels determined the activity of second line treatment with pegylated E. coli asparaginase: a retrospective analysis within ALL-BFM-trials. Blood, 2011.
Xu, et al., Inorganic nanoparticles as carriers for efficient cellular delivery. Chemical Engineering Science, 61(3):1027-1040, Feb. 2006.
Xu, et al., Strategies for Enzyme/Prodrug cancer therapy. Clinical Cancer Research, 7(11):3314-3324, Nov. 2001.
Yang, et al., Magnetite-containing spherical silica nanoparticles for biocatalysis and bioseparations. Anal. Chem., 76(5):1316-1321, 2004.
Yang, et al., Neutrophils exert protection in the early tuberculous granuloma by oxidative killing of my cobacteria phagocytosed from infected macrophages. Cell host & microbe, 12(3):301-312, Sep. 2012. PMID: 22980327.
Yang, et al., PEGylation confers greatly extended half-life and attenuated immunogenicity to recombinant methioninase in primates. Cancer research, 64(18):6673-6678, Sep. 2004. PMID: 15374983.
Yang, et al., Synthesis of hollow silica and titania nanospheres. Chem. Mater., 20(9):2875-2877, 2008.
Yu, et al., Impact of silica nanoparticle design on cellular toxicity and hemolytic activity. ACS Nano, 5(7):5717-5728, Jul. 2011.
Zahr, et al., Macrophage uptake of Core Shell nanoparticles surface modified with poly(ethylene glycol). Langmuir, 22(19):8178-8185, Sep. 2006.
Zeidan, et al., Pegasparaginase: where do we stand? Expert Opinion on Biological Therapy, 9(1):111-119, Jan. 2009.
Zhao, et al., Fabrication of silica nanoparticles and hollow spheres using ionic liquid microemulsion droplets as templates. Colloids and Surfaces A: Physicochemical and Engineering Aspects, 346(1-3):229-236, Aug. 2009.
Zhong, et al., Preparation of mesoscale hollow spheres of TiO2 and SnO2 by templating against crystalline arrays of polystyrene beads. Advanced Materials, 12(3):206-209, Feb. 2000.
Zhu, et al., Comorbidities of gout and hyperuricemia in the US general population: NHANES 2007-2008. The American journal of medicine, 125(7):679-687.e1, Jul. 2012. PMID: 22626509.
Zhu, et al., Prevalence of gout and hyperuricemia in the US general population: the national health and nutrition examination survey 2007-2008. Arthritis and rheumatism, 63(10):3136-3141, Oct. 2011. PMID: 21800283.
Zhu, et al., Stimuli-responsive controlled drug release from a hollow mesoporous silica sphere/polyelectrolyte multilayer core-shell structure. Angewandte Chemie (International Ed. in English), 44(32):5083-5087, Aug. 2005. PMID: 16015668.
Zlokarnik, et al., Quantitation of transcription and clonal selection of single living cells with -lactamase as reporter. Science, 279(5347):84-88, Jan. 1998.
Partial European Search Report for European Patent Application No. 14846394.6; dated Mar. 2, 2017.
Extended European Search Report for European Patent Application No. 14846394.6; dated Jun. 1, 2017.
International Search Report and Written Opinion of International Application No. PCT/US2015056179; dated Dec. 31, 2014; 16 pages.
Official Action for European Patent Application No. 14846394.6, dated Apr. 20, 2018, 4 pages.
Asselin, et al., "Prognostic significance of early response to a single dose of asparaginase in childhood acute lymphoblastic leukemia", Journal of Pediatric Hematology/Oncology, 21(1):6-12, Feb. 1999. PMID: 10029805.
Becker, et al., "Quality of life and disability in patients with treatment-failure gout", The Journal of rheumatology, 36(5):1041-1048, May 2009. PMID: 19332629.
Caruso, et al., "Hollow titania spheres from layered precursor deposition on sacrificial colloidal core particles", Advanced Materials, 13(10):740-744, May 2001.
Cheung, et al., "Antibody response to Escherichia coli I-asparaginase. prognostic significance and clinical utility of antibody measurement", The American journal of pediatric hematology/oncology, 8(2):99-104, 1986. PMID: 3526939.
Durden, et al., "Characterization of the effects of asparaginase from Escherichia coli and a glutaminase-free asparaginase from vibrio succinogenes on specific cell-mediated cytotoxicity", International Journal of Cancer, 27(1):59-65, 1981.
Tan, et al., "Recombinant methioninase infusion reduces the biochemical endpoint of serum methionine with minimal toxicity in high-stage cancer patients", Anticancer research, 17(5B):3857-3860, Oct. 1997. PMID: 9427792.
Tan, et al., "Serum methionine depletion without side effects by methioninase in metastatic breast cancer patients", Anticancer research, 16(6C):3937-3942, Dec. 1996. PMID: 9042316.
Terkeltaub, R., "Update on gout: new therapeutic strategies and options", Nature reviews. Rheumatology, 6(1):30-38, Jan. 2010. PMID: 20046204.
Zalewska-Szewczyk, et al., "The cross-reactivity of anti-asparaginase antibodies against different I-asparaginase preparations", Clinical and Experimental Medicine, 9(2):113-116, Jun. 2009.

\* cited by examiner

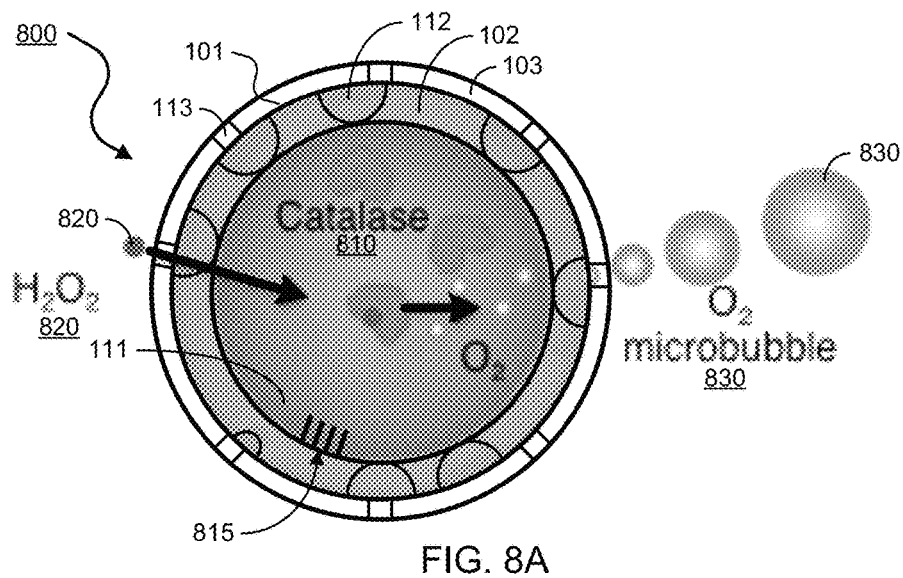
FIG. 8A
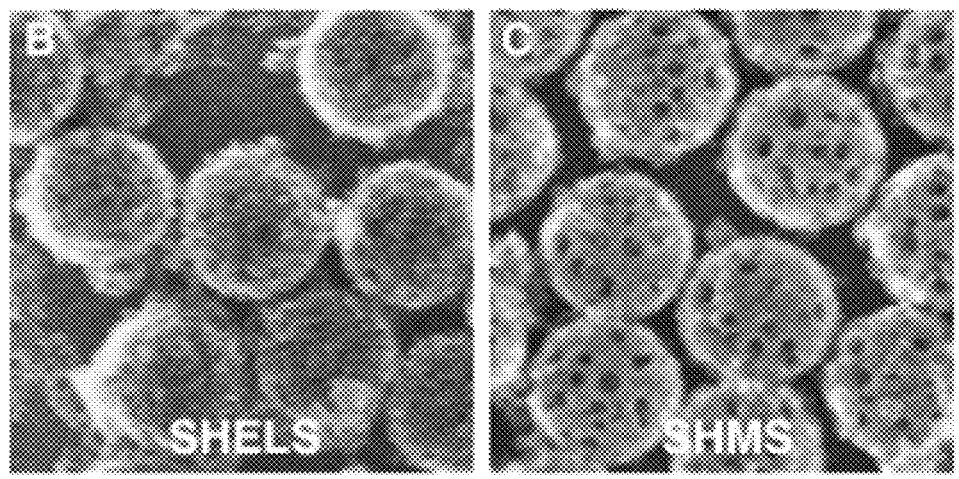
FIG. 8B
FIG. 8C

ENZYME-ENCAPSULATED NANOPARTICLE PLATFORM

CROSS REFERENCE TO RELATED APPLICATIONS

This patent document is a 35 USC § 371 National Stage application of International Application No. PCT/US2014/056179 filed Sep. 17, 2014, which further claims the benefit of priority of U.S. Provisional Patent Application No. 61/879,120, entitled "ENZYME ENCAPSULATED NANOPARTICLE DEVICES", filed on Sep. 17, 2013. The entire content of the aforementioned patent applications are incorporated by reference as part of the disclosure of this application

TECHNICAL FIELD

This patent document relates to systems, devices, and processes that use nanoparticle technologies.

BACKGROUND

Nanotechnology provides techniques or processes for fabricating structures, devices, and systems with features at a molecular or atomic scale, e.g., structures in a range of one to hundreds of nanometers in some applications. For example, nanometer scale devices can be configured to sizes within one hundred to ten thousand times smaller than human cells, e.g., similar in size to some large biological molecules (biomolecules) such as enzymes and receptors. Nanometer-sized materials used to create a nanostructure, nanodevice, or a nanosystem can exhibit various unique properties that are not present in the same materials scaled at larger dimensions and such unique properties can be exploited for a wide range of applications.

SUMMARY

Methods, systems, and devices are disclosed for implementing enzyme-encapsulated nanoparticles, e.g., including synthetic hollow enzyme-loaded nanospheres (SHELS), for use in a variety of diagnostic and therapeutic biomedical and environmental sensing applications.

In one aspect, a nanoparticle of the disclosed technology includes a shell structure including an internal layer and an external layer, in which the internal layer is structured to enclose a hollow interior region and structured to form one or more holes penetrating through the internal layer, and the external layer is formed of a porous material around the internal layer. The nanoparticle includes an enzyme contained within the interior region of the shell structure, the internal layer is structured to form the one or more holes sized to allow the enzyme to pass through the internal layer. In implementations, the enzyme is incapable of passing through the external layer, but small molecules of a size smaller than the pores are capable of passing into and out of the interior region of the shell structure. In some implementations, for example, the nanoparticle can be configured to have a diameter in a range between 100 nm to 500 nm.

Implementations of the nanoparticle can include one or more of the following features. For example, the enzyme contained within the shell structure can include a catalase enzyme. For example, the nanoparticle can be configured to detect hydrogen peroxide in a fluid via a catalytic interaction between the catalase enzyme and the hydrogen peroxide, in which the shell structure of the nanoparticle provides a nucleation site for formation of oxygen microbubbles as a result of the catalytic interaction. In some implementations, for example, the enzyme contained within the shell structure can include an enzyme in the L-asparaginase enzyme family. For example, the nanoparticle can further include a ligand molecule conjugated to the shell structure, in which the ligand molecule has an affinity to a receptor molecule found on a target structure to attract and bind the shell structure to the target structure. In some examples, the target structure can be a living tissue within an organism, the shell structure bound to the living tissue, e.g., in which the target structure is a tumor. In some implementations, for example, the enzyme contained within the shell structure can include methioninase. For example, the nanoparticle can be configured to deliver the methioninase to a tumor in a living tissue within an organism, in which the shell structure inhibits antibodies and other substances that degrade methioninase from entering the interior region. In some implementations, for example, the enzyme contained within the shell structure can include uricase. For example, the nanoparticle can be configured to deliver the methioninase to arthritic tissue in a living tissue within an organism, in which the shell structure inhibits antibodies and other substances that degrade uricase from entering the interior region.

In one aspect, a nanoparticle for catalyzing an analyte includes a shell structure including an internal layer and an external layer, the internal layer structured to enclose a hollow interior region and structured to form one or more holes penetrating through the internal layer, and the external layer formed of a porous material arranged around the internal layer; an enzyme contained within the interior region of the shell structure, the internal layer is structured to form the one or more holes sized to allow the enzyme to pass through the internal layer; and a biochemical cofactor corresponding to the enzyme, in which the biochemical enzyme is contained in the interior region and capable of binding to the enzyme, and the porous material of the external layer is structured to prevent the enzyme from passing through the external layer while permitting an analyte smaller than the enzyme to pass through the external layer with the enzyme structured to catalyze the analyte.

In one aspect, an ultrasound-interactive nanoparticle sensor device for detecting reactive oxidative species includes a nanoparticle structured to include a shell structure including an internal layer and an external layer, the internal layer enclosing a hollow interior region and structured to form one or more holes penetrating through the internal layer, and the external layer formed of a porous material arranged around the internal layer; and an enzyme encapsulated within the interior region of the shell structure, in which the internal layer is structured to form the one or more holes sized to allow the enzyme to pass through the internal layer, and the enzyme is structured to catalyze a reactive oxidative species (ROS) to decompose and produce oxygen. The enzyme-encapsulated nanoparticle can produce microbubbles from the oxygen produced by decomposition of the ROS within the nanoparticles, and the produced microbubbles can cause a change in a returned acoustic waveform carrying information on the microbubbles responsive to an application of an ultrasonic acoustic energy.

In one aspect, a nanoparticle sensor device for detecting analyte includes enzyme-encapsulated nanoparticles capable of being injected into a biological system, in which the enzyme-encapsulated nanoparticles is structured to include a shell structure including an internal layer and an external layer, the internal layer enclosing a hollow interior region and structured to form one or more holes penetrating through the internal layer, and the external layer formed of a porous material arranged around the internal layer. The shell structure includes an enzyme contained within the interior region of the shell structure with the internal layer structured to form the one or more holes sized to allow the enzyme to pass through the internal layer. The external layer is structured to prevent the enzyme from passing through the external layer but allow an analyze smaller than an enzyme to pass through the external layer. The enzyme is structured to catalyze the analyte that enters the interior region. The enzyme-encapsulated nanoparticles is structured to include a fluorophore attached to the shell structure and capable of emitting an optical fluorescent signal based on the concentration of a chemical reactant or chemical product of a catalytic interaction of the enzyme and the analyte. The nanoparticle sensor device includes a light source to direct an excitation light into the biological system to cause emission of the optical fluorescent signal. The nanoparticle sensor device includes an optical detector to detect the emitted optical fluorescent signal generated by the enzyme-encapsulated nanoparticle based on catalytic interaction between the enzyme and the analyte within the shell structure.

BRIEF DESCRIPTION OF THE DRAWINGS

FIG. 8A shows a schematic illustration of an exemplary catalase-loaded SHELS (catSHELS) structure.

FIGS. 8B and 8C show scanning transmission electron microscopy (STEM) and scanning electron microscopy (SEM) images of exemplary fabricated catSHELS.

DETAILED DESCRIPTION

Figure 1:
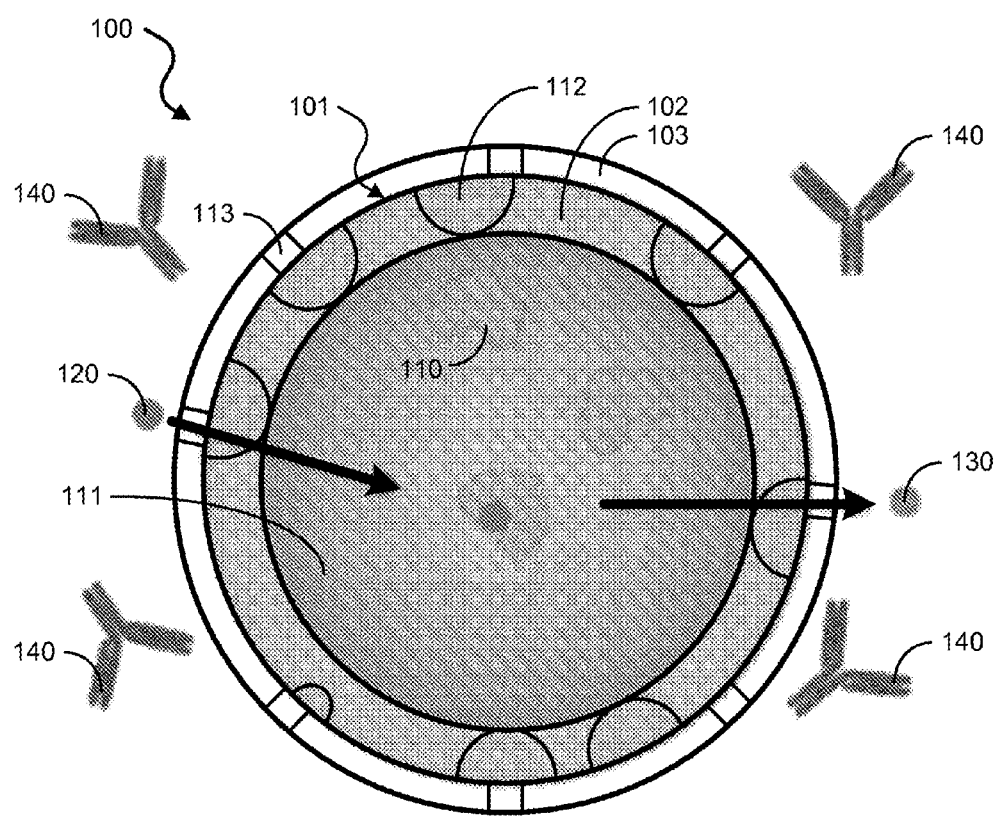
FIG. 1 shows a diagram of an exemplary synthetic hollow enzyme-loaded nanospheres (SHELS) particle structure.

Techniques, systems, and devices are disclosed for implementing enzyme-encapsulated nanoparticle structures for use in a variety of diagnostic and therapeutic biomedical and environmental sensing applications. In some implementations, the disclosed nanoparticle structures include synthetic hollow enzyme-loaded nanospheres (SHELS).

In one aspect, a nanoparticle to encapsulate an enzyme of the disclosed technology includes a shell structure including an internal layer and an external layer, in which the internal layer is structured to enclose a hollow interior region and include one or more holes penetrating the internal layer, and the external layer is formed of a porous material around the internal layer. The nanoparticle includes an enzyme contained within the interior region of the shell structure, the enzyme having entered the shell structure through the one or more holes and is incapable of passing through the external layer. In implementations, the enzyme is incapable of passing through the porous material, but small molecules of a size smaller than the pores are capable of passing into and out of the interior region of the shell structure. For example, some pores of the external layer may directly penetrate through the external layer, while the pores of the external layer can form a network of pores that allow the passage of the small molecules through the external layer. In some examples, the pores may align with the penetrating holes of the internal layer, whereas in some examples, the internal layer is formed of a porous material that allows the passage of the small molecules similar to that of the external layer while preventing the encapsulated enzyme from escaping the interior region. In some embodiments of the nanoparticles, for example, the shell structure can be configured to have a diameter in a range between 100 nm to 500 nm. In some embodiments, for example, the external layer can include nanoporous silica. In such embodiments, for example, the internal layer can also include nanoporous silica.

In some implementations of the enzyme-encapsulated nanoparticle, for example, the enzyme contained within the shell structure can include a catalase enzyme. For example, the nanoparticle can be configured to detect hydrogen peroxide in a fluid via a catalytic interaction between the catalase enzyme and the hydrogen peroxide, in which the shell structure of the nanoparticle provides a nucleation site for formation of oxygen microbubbles as a result of the catalytic interaction. In some implementations of the enzyme-encapsulated, for example, the enzyme contained within the shell structure can include an enzyme in the L-asparaginase enzyme family. For example, the nanoparticle can further include a ligand molecule conjugated to the shell structure, in which the ligand molecule has an affinity to a receptor molecule found on a target structure to attract and bind the shell structure to the target structure. In some examples, the target structure can be a living tissue within an organism, the shell structure bound to the living tissue, e.g., in which the target structure is a tumor. In some implementations of the enzyme-encapsulated, for example, the enzyme contained within the shell structure can include methioninase. For example, the nanoparticle can be configured to deliver the methioninase to a tumor in a living tissue within an organism, in which the shell structure inhibits antibodies and other substances that degrade methioninase from entering the interior region. In some implementations of the enzyme-encapsulated, for example, the enzyme contained within the shell structure can include uricase (uric acid oxidase or urate oxidase). For example, the nanoparticle can be configured such that the shell structure inhibits antibodies and other substances that degrade uricase from entering the interior region.

Disclosed are localized nanoparticles capable of encapsulating, carrying, and controllably releasing enzymes to achieve systemic effects in vivo and in vitro to biological tissue in living organisms, e.g., such as humans and non-human animals, in a variety of diagnostic and therapeutic applications. The disclosed enzyme-encapsulated nanoparticle platform has a number of benefits. For example, it allows more manageable and predictable in vivo distribution and circulation of the multi-layered hollow porous nanoparticles. Also for example, the disclosed nanoparticle system is capable of localized activity that enables more stable in vivo enzyme kinetics, e.g., since complicated variations due to accumulation of nanoparticles at the clearance organs is eliminated to a great extent. The disclosed nanoparticle system therefore provides a more straightforward and governable solution for already complicated in vivo applications.

The disclosed nanoparticle platform is designed to preserve the bioactivity of the enzyme during the encapsulation of the enzyme, the carrying of the enzyme in a biological system (e.g., during circulation of the nanoparticle in the circulatory system for targeted delivery to the target biological tissue), and facilitate within the nanoparticle interactions between the encapsulated enzymes and specific biological and/or chemical entities in the localized environment of the target tissue. The enzymes encapsulated within the nanoparticles can cause changes to such biological and/or chemical entities that achieve a localized systemic effect on the targeted biological tissue. The disclosed nanoparticle platform can thereby be used to control outcomes in the biological system that can be used for therapeutic and/or diagnostic purposes.

FIG. 1 shows a diagram of an exemplary SHELS nanoparticle 100. The SHELS particle 100 includes a shell structure 101 including an internal and an external layer 103. The internal layer 102 is structured to include holes or mesopores 112 penetrating through the internal layer 102 and enclose a hollow interior region 111. The external layer 103 is formed around the internal layer 102 and structured to include pores 113, in which at least some of the pores 113 penetrate through the external layer 103. The SHELS nanoparticle 100 can be loaded with an enzyme 110 contained within the interior region 111 of the shell structure 101, in which the enzyme 110 is loaded in the interior region 111 through the holes 112 prior to forming the external layer 103 over the internal layer 102, and is incapable of passing through the pores 113 of the external layer 102. Enzymes 110 encapsulated within the hollow core of the SHELS particle 100 cannot escape, while small molecules of a size less than the size of the pores 113, e.g., which can include enzyme substrates 120, can diffuse through the nanoporous shell structure 101 and interact with the enzyme 110, e.g., including becoming modified by the enzyme 110 to form a new product 130. The SHELS nanoparticle 100 also protects the encapsulated enzyme 110 from antibody binding, as antibodies 140 are not capable of penetrating into the SHELS nanoparticle 100. In some implementations, for example, the SHELS nanoparticle 100 can optionally include a charged material layer formed in mesopores 112, e.g., to provide an electrostatic force to further prevent substances (e.g., such as the enzymes 110) from escaping the hollow interior region 111.

I. Exemplary Therapeutic Biomedical Applications of SHELS

I.1. L-Asparaginase Encapsulation within SHELS (Synthetic Hollow Enzyme-Loaded Nanospheres)

I.1.1. Background of L-Asparaginase and L-Asparaginase Based Therapies

L-Asparaginase

The enzyme family of L-asparaginases (L-asparagine amidohydrolases, EC 3.5.1.1) catalyzes the reaction of conversion of the amino acid L-asparagine into L-aspartate and ammonia. L-asparaginase is one of the few enzymes that successfully find use in the treatment of cancer. The use of L-asparaginases in the treatment of cancer is based on the reliance of cancerous cells to exogenous asparagine due to their lack of sufficient asparagine synthetase activity. Therefore, the depletion of exogenous L-asparagine by L-asparaginase compromises protein synthesis leading to apoptosis of cancerous cells. On the other hand, non-cancerous cells are not affected due to sufficient activity of asparagine synthetase.

Currently, asparaginases are approved to be used for acute lymphoblastic leukemia. For example, *Escherichia coli* (e.g., Kidrolase, EUSA Pharma, Oxford, UK; Elspar, Ovation Pharmaceuticals, Deerfield, Ill.; Crasnitin, Bayer AG, Leverkusen, Germany; Leunase, Sanofi-Aventis, Paris, France; Asparaginase Medac, Kyowa Hakko, Tokyo, Japan) and *Erwinia chrysanthemi* (e.g., Erwinase, EUSA Pharma, Oxford, UK.) are the two species of bacteria from which clinical asparaginase can be obtained. There is also a polyethylene glycol (PEG) modified version of *Escherichia coli* asparaginase (e.g., Oncaspar, Sigma-Tau Pharmaceuticals, Inc., Gaithersburg, Md.). The PEG modified version has a long circulation half-life and in vivo activity, which requires fewer injections. Aside from asparaginase's use in Acute Lymphoblastic Leukemia (ALL), asparagine depletion has been shown to be effective against other cancer types, e.g., including acute myeloid leukemia (AML), chronic myeloid leukemia, T-cell acute lymphoblastic leukemia, promyelocytic leukemia, prostate and hepatocarcinoma, carcinoma, breast and ovarian adenocarcinoma, fibrosarcoma and gastrointestinal cancer.

Side Effects of L-Asparaginase Using Conventional Delivery Approaches

Despite the great potential of asparaginases and their current use in the clinic for ALL, their utility can be limited by the toxicities associated with asparaginase, e.g., such as hepatic and central nervous system toxicity and pancreatitis. Moreover, asparagine depletion also can cause a reduction in synthesis of blood clotting factors, which might lead to hemorrhage or thrombosis.

More importantly, asparaginases are both antigenic and immunogenic due to their foreign origin. This causes life-threatening hypersensitivity reactions and anaphylactic shocks. Although PEG-asparaginase have less toxicity with its longer circulation half-life and requirement of reduced number of administrations compared to native asparaginase, antibodies generated against enzyme and PEG itself can still render the therapy completely useless. Currently, for the first line treatment PEG-asparaginase is preferred due to its more manageable toxicity profile and requiring less number of injections. Once an allergic and immunogenic reaction is generated against the first line asparaginases, the asparaginase in the regimen is replaced by *Erwinia chrysanthemi* asparaginase. Although *Erwinia chrysanthemi* asparaginase has a remarkably shorter half-life requiring a lot of injections, antibodies generated against *Escherichia coli* asparaginases are not cross-reactive with it.

Pancreatitis as a result of asparaginase use is mostly associated with glutamine depletion, disrupting protein synthesis, since glutamine is involved in about one-half of the whole body resources of all free amino acids. To date, there is not a clear relation with the occurrence and severity of the pancreatitis with the source and formulation of the asparaginase. However, in the case of PEG-asparaginase the number of pancreatitis cases increases about two times. Currently, clinically available asparaginases also possess glutaminase activity in addition to asparaginase depletion. Glutamine is important in the rescue pathway for normal cells since it is used by asparagine synthetase to produce asparagine. There are studies that have suggested that limiting glutaminase activity would decrease toxicity and increase apoptosis in cells treated with asparaginase.

Multiple other toxicities have been associated with clinical use of *E. coli*-, PEG-, or *Erwinia*-asparaginase. Decreased liver synthetic function in addition to direct hepatotoxicity leads to liver function abnormalities. Pancreatic cells are also damaged, resulting in elevated blood glucose levels and pancreatitis. Both thrombosis and bleeding, frequently affecting the central nervous system, can occur due to abnormalities in clotting proteins. Animal and human studies have also demonstrated significant humoral and cell-mediated immune suppression, with a decrease in T cell dependent antigens on sheep red blood cells and a decrease in the number of immunoglobulin producing B cells in the germinal centers of the spleen.

L-Asparaginase for the Treatment of Acute Lymphoblastic Leukemia (ALL)

L-asparaginase is a critical component of the therapeutic regimen that is used for treatment of pediatric ALL for over 40 years. The regimen includes vincristine, prednisone, cyclophosphamide and doxorubicin besides asparaginase and has a cure rate of 80%.

The use of asparaginase is mostly limited to pediatric leukemia due to its side effects, which becomes especially more significant in adults. The first line of ALL for pediatric leukemia includes Elspar® or Oncaspar®. Oncaspar has a plasma half-life of about 6 days, and the plasma half-life of Elspar is around one day. If there is an allergic reaction against Oncaspar or Elspar, the asparaginase in the treatment regimen is switched to Erwinase® (*Erwinia chrysanthemi*-type asparaginase) since antibodies produced against is not cross-reactive. Erwinase has the shortest plasma half-life of around 15 hours among all the clinically approved formulations.

Polyethylene Glycol (PEG) Functionalization of Asparaginase

Due to its foreign origin, native L-asparaginase is immunogenic leading to severe allergic reactions such as hypersensitivity reactions and anaphylaxis. L-asparaginase also has a short circulation half-life that requires frequent administrations. To reduce immunogenicity of foreign proteins, the common approach is to attach polyethylene glycol (PEG) to proteins. By masking the protein surface, PEG reduces antibody binding as well as degradation of proteins by proteolytic enzymes. PEG conjugation also increases the molecular weight of the enzyme, which reduces ultrafiltration in the kidneys.

PEG functionalized L-asparaginase (e.g., such as Oncaspar, Sigma-Tau Pharmaceuticals, Inc., Gaithersburg, Md.) have a remarkable longer circulation half-life with significantly less immunogenicity as compared to the native enzyme. While PEG functionalization increases the circulation half-life of L-asparaginase and delays the formation of antibodies to the enzyme, it does not completely eliminate the eventual production of neutralizing antibodies and compromises enzyme activity.

Nevertheless, the functionalized PEG does not completely prevent binding of anti-L-asparaginase antibodies. Clinical studies have shown that intensive use of L-asparaginase results in improved disease free survival in ALL. These studies also have indicated that 35% of patients that received *E. coli* L-asparaginase produced neutralizing antibodies to the enzyme. These neutralizing antibodies were cross-reactive with the PEG-L-asparaginase in 80% of the cases reducing enzyme activity, e.g., both by preventing depletion of asparagine and by accelerating the clearance of the enzyme. In the patients that develop antibodies against L-asparaginase, lower remission rates are observed.

In addition, there are antibodies produced against PEG causing rapid clearance of PEG-L-asparaginase. Currently, about a quarter of the healthy population already have antibodies against PEG (anti-PEG). Continuous treatment with PEGylated proteins increases the number of cases that fail the PEGylated protein therapy.

Furthermore, precisely defined and reproducible conjugation of PEG to proteins is a laborious and expensive process.

Despite the immune responses against l-asparaginase, the therapeutic regimen including L-asparaginase has close to 80% cure rate in pediatric ALL mainly due to the fact that the patients are already immune-suppressed. However, the unsuccessful 20% in pediatric ALL, the limited effectiveness in adult ALL, and the limited clinical success for other types of cancer are mainly due to these immune-responses and toxicity effects, which have yet to be effectively addressed.

Encapsulation of L-Asparaginase within Red Blood Cells

Another conventional approach to attempt prolonged in vivo activity and reduce allergic reactions is the encapsulation of enzymes within red blood cells (RBC). For example, RBC encapsulation of L-asparaginase has been explored for a few decades showing extended asparagine depletion up to few weeks, with very little allergic reactions, demonstrating better results than PEG-L-asparaginase in some cases. First, to prepare RBC for loading with a payload, freshly collected blood is centrifuged followed by several washes in isosmotic solution to remove other blood components. To load enzymes into the RBCs, there are various methods including osmosis-based methods, electroporation, and drug induced endocytosis.

Osmosis based methods for encapsulating L-asparaginase within RBCs include loading the enzymes through the pores generated by exposing RBC membranes to a hypotonic solution and swelling the cells. There are various methods that take advantage of this process including hypotonic dilution, hypotonic pre-swelling, the osmotic pulse, hypotonic hemolysis and hypotonic dialysis. Hypotonic dialysis is by far the most commonly used method. In hypotonic dialysis, for example, the suspension of RBCs is dialyzed against a hypo osmotic buffer at 4° C. Here, the variation comes from the osmolality of the medium, which requires a compromise between the efficiency of the encapsulation and the least possible hemolysis of the dialyzed RBCs. Immersion in hypo osmotic buffer is followed by annealing of RBCs in an isosmotic medium and resealing in a hyperosmotic buffer. Here, several factors affect the result such as the tonicity of the solutions employed, duration of dialysis, pH and temperature of the medium, and concentration of the protein in contact with the erythrocytes.

Electroporation methods for encapsulating L-asparaginase within RBCs include loading of payloads through pores induced in RBC membrane by application of a strong external electric field.

In drug-induced endocytosis methods for encapsulating L-asparaginase within RBCs, the drugs such as primaquine, hydrocortisone, vinblastine and chlorpromazine are used to induce stomatocyte formation in the cell membrane. RBCs, as carriers of enzymes, are highly biocompatible and they provide prolonged therapeutic levels of the enzymes. They effectively prevent access of antibodies to the encapsulated L-asparaginase delaying and reducing immune responses. On the other hand, since they are biological origin, they are removed by reticulo-endothelial system (RES) limiting their useful life and, at the same time, might pose toxicological problems. Nonetheless, during the loading process, the physiology of the erythrocyte may change accelerating the clearance by RES. Compared to other conventional carrier and encapsulation technologies, they present greater variability and lesser standardization in their in preparation due to their biological origin. Another issue that limits their successful implementation in the clinic is their storage. Storing of RBCs involves additional processes and additives to improve their stability. These processes affect the original structure of RBCs and accelerate their removal from the circulation. They are also liable to biological contamination due to the origin of the blood, the equipment, exposure to environment and the environment. Therefore, their preparation requires strict control during collection, handling and loading of RBC, which complicates and limits their use in clinical settings.

Conventional enzymatic therapies are based on circulating enzymes. Once an immune response is generated resulting in specific antibody production, antibodies bind to the enzymes and cause them to be cleared or be neutralized.

One way of preventing immune response is encapsulating enzymes within nanoparticles, which prevents access of antibodies to the enzyme. However, existing nanoparticles have limited circulation half-life, and are very unlikely to compete with the circulation half-life of PEGylated enzymes, and exhibit increased toxicity as compared to PEGylated enzymes.

I.1.2. Encapsulation of Asparaginase within SHELS
Systemic L-Asparagine Depletion with Localized Asparaginase Loaded SHELS In one example, L-asparaginase is utilized as the localized enzyme encapsulated in the synthetic hollow enzyme-loaded nanospheres of the present technology.

Figure 2:
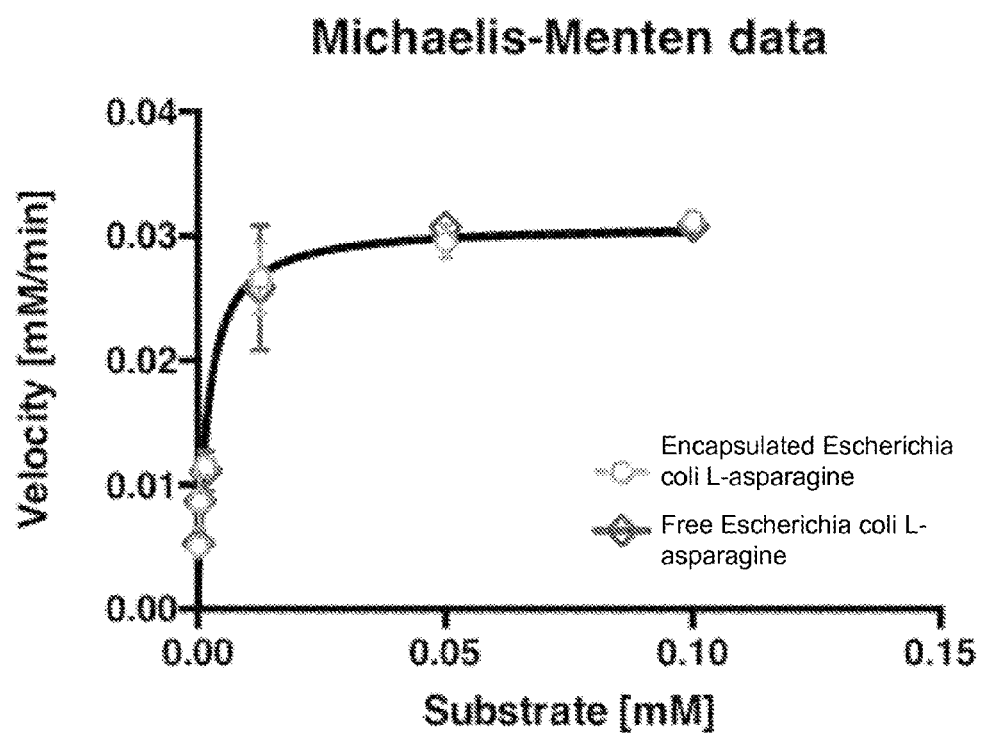
FIG. 2 shows a data plot depicting the Michaelis-Menten kinetics for both free and encapsulated L-asparaginase.

Exemplary implementations of the disclosed SHELS nanoparticle 100 were performed to demonstrate the effects of SHELS encapsulation on the activity of the L-asparaginase. To determine whether encapsulated enzymes are in free state within the hollow interior region 111 or embedded within the shell or adsorbed on the interior of the shell, the kinetic parameters of encapsulated and free *Escherichia coli* L-asparaginase were compared. The Michaelis-Menten kinetics model can be depicted by $$v = \frac{V_{max}[S]}{K_m + [S]},$$

where: v represents the reaction rate of an enzyme with a substrate having a concentration [S], $V_{max}$ represents the maximum rate achieved by the system, and $K_m$ represents the Michaelis constant that is the substrate concentration at which the reaction rate is half of $V_{max}$. FIG. 2 shows a data plot depicting the Michaelis-Menten kinetics for both free and encapsulated L-asparaginase, e.g., Elspar encapsulated within exemplary SHELS (circles) and free Elspar (diamonds). The maximum rate achieved by the enzyme substrate system at saturating substrate concentration, $V_{max}$, was 0.3087 µM/min for encapsulated whereas was 0.3108 µM/min for the free enzyme. The Michaelis constant, Km, was calculated as 0.001838 mM for encapsulated L-asparaginase and 0.001989 for free L-asparaginase. The turnover number, kcat, was derived as 108.8 for encapsulated and 109.6 for free enzyme. This similar behavior might indicate that the majority of the encapsulated enzyme is at free state within the hollow interior.

The disclosed SHELS nanoparticles are capable of protecting L-asparaginase while enabling L-asparaginase to remain bioactive and function in a therapeutically relevant setting. Exemplary implementations of the L-asparaginase-loaded SHELS nanoparticles 100 were performed for in vivo L-asparagine depletion using exemplary SHELS introduced intramuscularly.

For over 40 years, L-asparaginase from *Escherichia coli* has been used to treat acute lymphoblastic leukemia (ALL) in order to deplete circulating L-asparagine, which cannot be synthesized by leukemic cells unlike normal cells. L-asparagine is converted into aspartic acid and ammonia by L-asparaginase, thereby starving selectively leukemic cells and causing cell death. Yet, immune responses generated against the L-asparaginase are a significant clinical problem and can cause rapid neutralization and clearance of the enzyme as well as significant side effects such as hypersensitivity reactions and anaphylaxis. Because an extended residence time in tissue was observed with intramuscular injection previously, this route of administration was chosen for testing systemic depletion of L-asparagine. L-asparaginase was presented as either free enzyme or loaded in the exemplary SHELS nanostructures. In both cases for the exemplary implementations, a clinically approved L-asparaginase enzyme, brand name Elspar®, was used, and the same total enzyme activity (5 IU) was given to all mice. The duration of L-asparagine depletion by equivalent amounts of Elspar in either naïve (FIG. 3A) or passively immunized (FIG. 3B) mice was determined.

Figure 3A:
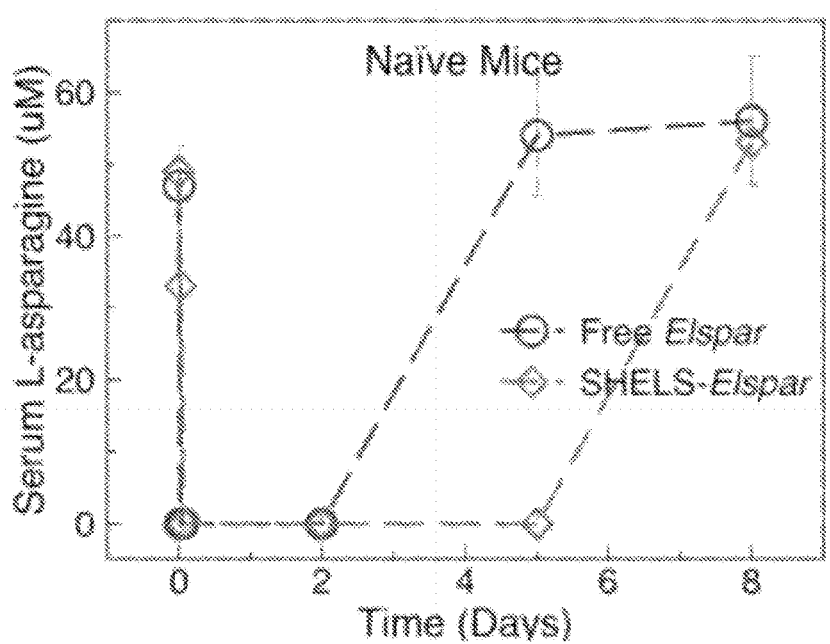
FIGS. 3A and 3B show plots depicting exemplary data of asparagine depletion by free and encapsulated L-asparaginase in vivo in naïve mice and in passively immunized mice, respectively.
Figure 3B:
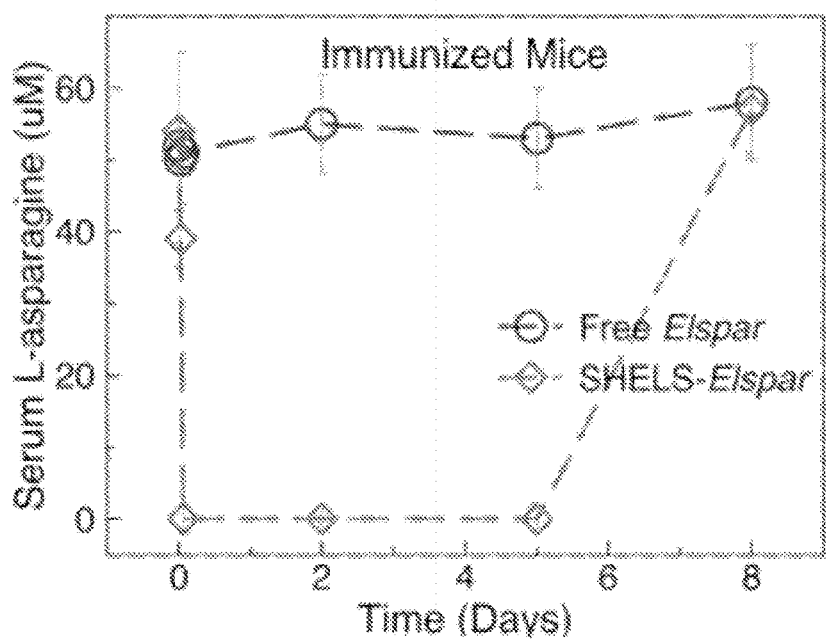

FIGS. 3A and 3B show plots depicting exemplary asparagine depletion data by free and encapsulated L-asparaginase in vivo in naïve mice and in passively immunized mice, respectively. Free Elspar (circles) and Elspar-loaded SHELS (diamonds) were injected intramuscularly into naïve mice with equivalent units of activity. Serum L-asparagine levels pre- and post-injection up to 8 days were measured. Also, free Elspar (circles) and Elspar-loaded SHELS (diamonds) were injected intramuscularly to passively immunized mice with equivalent units of activity. Serum L-asparagine levels pre- and post-injection up to 8 days were also measured. The exemplary error bars shown in FIGS. 3A and 3B correspond to standard deviation of at least three replicate experiments.

As shown in FIG. 3A, in naïve mice, free enzyme rapidly depleted the serum L-asparagine and kept it at undetectable levels for at least two days. By day five, the serum L-asparagine had recovered completely. Elspar provided by the exemplary SHELS of the disclosed technology (SHELS-Elspar) produced a more durable L-asparagine depletion of greater than five days, as shown in FIG. 3A. As shown in FIG. 3B, no L-asparagine depletion occurred for free Elspar in immunized mice, whereas the immune response demonstrated no effect against Elspar-encapsulated SHELS, which caused L-asparagine depletion of greater than five days in the passively immunized mice.

The enzyme-encapsulated platform of the present technology can also include functionalization of the exemplary SHELS particle surface to improve tissue retention, reduce cell uptake, and protein binding without affecting encapsulated enzyme activity, which can further prolong the in vivo activity.

Exemplary implementations of the disclosed SHELS nanoparticle 100 were performed to demonstrate anti-tumor efficacy. There are various types of tumors that are sensitive to asparagine depletion. One example of solid tumors includes pancreatic cancer. PancO2 cells are known to be sensitive to asparaginase depletion. The exemplary implementations described here used a subcutaneous model of pancreatic cells. For example, 6U of L-asparaginase loaded SHELS were injected every 5 days to the pancreatic tumor, e.g., to keep the asparagine levels down, as demonstrated in FIGS. 4A and 4B.

Figure 4A:
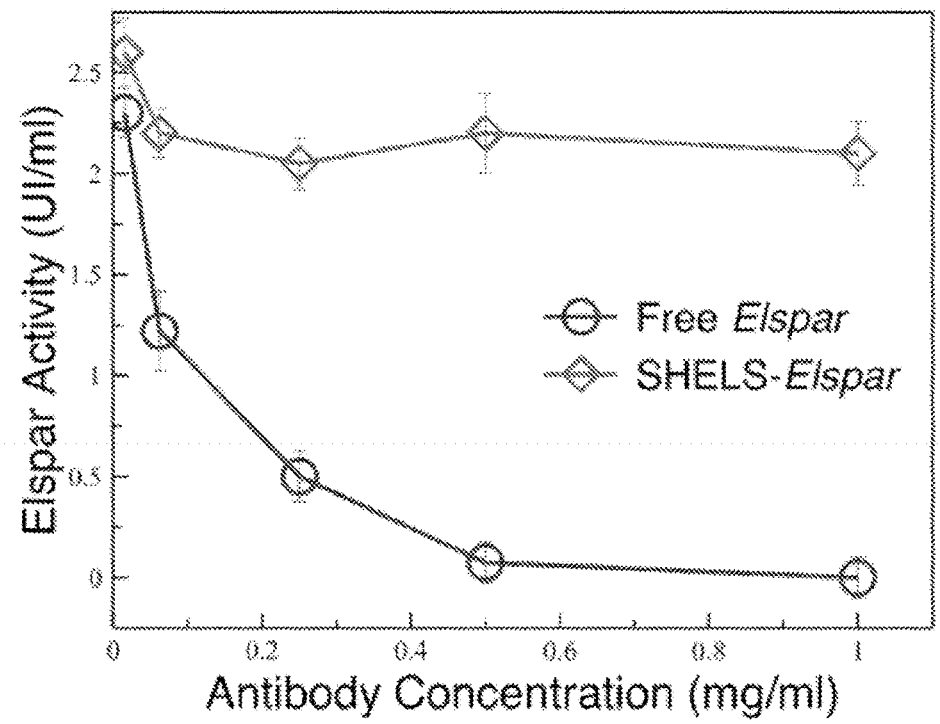
FIG. 4A shows a data plot depicting exemplary data of neutralization assay in the presence of rabbit polyclonal antibodies against free and encapsulated L-asparaginase in vitro.

FIG. 4A shows a plot depicting exemplary data of a neutralization assay in the presence of rabbit polyclonal antibodies against free Elspar and Elspar-encapsulated SHELS in vitro, e.g., in 1×PBS. The activity of each data point was adjusted to 2.5 UI/mL before introduction of antibodies. Remaining activity (y axis) in the presence of various concentrations of antibodies (x axis) was measured. In the data plot, the free Elspar data is depicted with circles, and the Elspar-loaded SHELS data is depicted with diamonds. The exemplary error bars shown in FIG. 4A correspond to standard deviation of at least three replicate experiments.

When neutralizing anti-L-asparaginase antibodies were given before free Elspar, L-asparagine depletion was not observed, as shown in FIG. 4A. However, the exemplary Elspar-encapsulated SHELS were unaffected by the prior introduction of neutralizing antibodies as shown in FIG. 4A, e.g., verifying the protected operation of enzymes in therapeutically relevant in vivo setting.

Figure 4B:
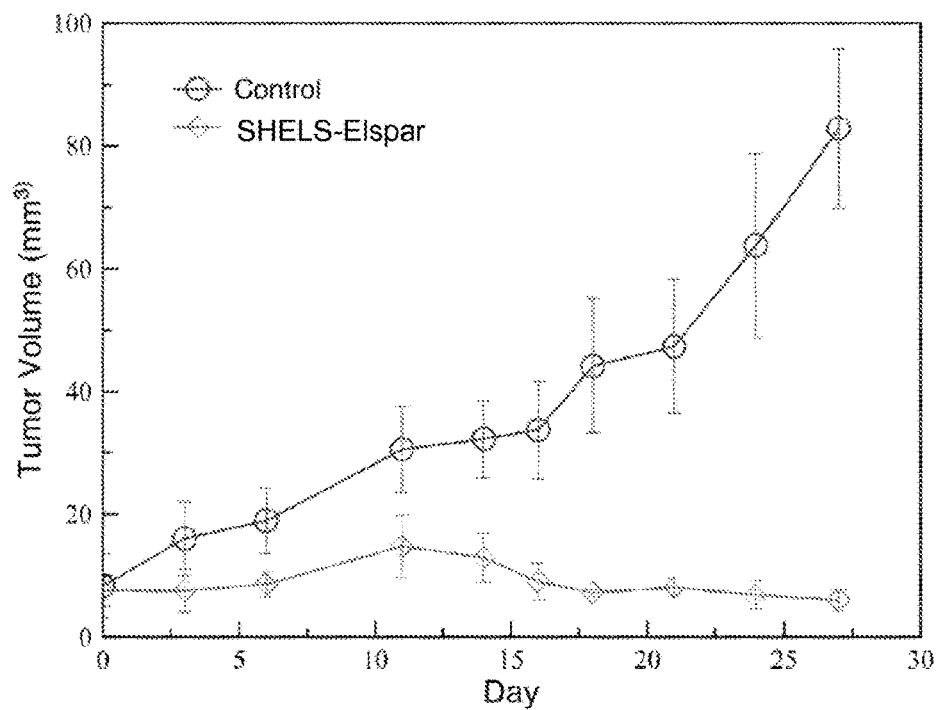
FIG. 4B shows a plot depicting exemplary data of anti-tumor efficacy of L-asparaginase loaded SHELS in the PancO2 mouse models.

FIG. 4B shows a plot depicting exemplary data of anti-tumor efficacy of Elspar-encapsulated SHELS in vivo in exemplary PancO2 mouse models. Tumor-bearing mice were treated started from tumor volume 7-10 mm³. The subcutaneous tumor volume was measured by caliper and calculated. Y-axis represented the volume of the tumor, and X-axis represents the number of days following treatment start day. The control injected in the PancO2 mouse model was saline, and Elspar-encapsulated SHELS correspond to 6 units of activity and $1 \times 10^{12}$ particles injected every 5 days.

As shown in FIG. 4B, an immediate reduction in the rate of tumor growth is observed for the Elspar-encapsulated SHELS, as opposed to the continued tumor growth using the control. It is noted that in this exemplary implementation, the reduction in tumor growth rate for the Elspar-encapsulated SHELS was followed by a remission after around 3rd injection. This exemplary result is important in various ways. It shows that localized particles can achieve a systemic effect, which will have efficacy against a localized tumor. This can have various benefits. For example, the selectivity is achieved by biology, not physical confinement of particles at the tumor. Also, it gives more manageable distribution and circulation kinetics. Additionally, it gives a rather stable activity compared to circulation half-life, which has a decaying response.

When all these are considered, for example, the use of SHELS compared to other enzyme encapsulation approaches also has other several benefits. To achieve a systemic effect, the amount of enzyme becomes important. This will be limited to the carrier materials. Therefore, amount of carrier material per enzyme is an important feature. SHELS with high loading efficiency will be important in that sense. Therapeutic treatments typically require having multiple administration, therefore, clearance and/or degradation is another variable. In another advantage, SHELS can exhibit excellent clearance dynamics from the biological system. Furthermore, SHELS can provide protection from immune system.

I.1.3. Exemplary Methods of the Implementations Using L-Asparaginase Enzyme

Asparaginase was labeled using Cy5 using NHS ester chemistry. Briefly, for example, Cy5 has a mono reactive NHS (N-HydroxySuccinimide) ester that reacts with amino groups on the enzyme. Measurement of activity of asparaginase with CCF2 included measuring activity in 100% normal mouse serum as the initial rate of increase of the ratio of blue fluorescence (447 nm) to green fluorescence (520 nm) with excitation at 409 nm.

Nessler's Assay was performed for measurement of asparaginase activity. 100 μL of asparaginase and asparagine solution was reacted at 37° C. followed by stopping with 100 μL of 5% trichloro acetic acid. 20 μL of Nessler's reagent was added to each reaction at 5 min and absorbance at 492 nm was measured at 37° C. on a Tecan Infinite 200 PRO Plate reader. Enzyme activity was quantified based on the standard curve of ammonia obtained by Nessler's reagent.

Enzyme kinetics was analyzed using Prism 6 Software by Graphpad Software Inc.

I.2. Methioninase Encapsulated within SHELS: met-SHELS

I.2.1. Methioninase Depletion as an Exemplary Therapeutic Approach

Depletion of amino acid methionine has been shown to be effective in the treatment of many types of cancer. Cancer cells are sensitive to methionine depletion if based on deletion of the genes CDKN2A (p16IN K4a) and methylthioadenosine phosphorylase (MTAP), both of which are co-located on chromosome 9p21. The deletion of MTAP makes cells hypersensitive to depletion of methionine, which is an essential amino acid obtained only through diet. Many cancer cells, especially solid tumors, have hypersensitivity to methionine depletion. The deletion of CDKN2A is one of the most common mutations encountered in cancer, especially seen melanoma, pancreatic adenocarcinoma, glioblastoma, non-small cell lung cancer, bladder carcinoma, and some leukemias.

Methionine depletion can produce cell arrest in S and G2 phases of cell cycle. For example, many cytotoxic drugs, such as paclitaxel, are the most effective at these phases, thus, making methionine depletion a factor for combinatorial therapeutic approaches. As a promising anti-cancer agent, recombinant methioninase from *Pseudomonas putida* entered phase I clinical trials and was found to be safe. Although it was found safe, methionine depletion could only be achieved for a short time, and thus insufficient for therapeutic efficacy. Initially, rapid clearance due to immune responses against the foreign enzyme was thought to be the main reason behind short duration of the depletion. To reduce immune responses generated against unmodified enzyme, a PEGylated form of methioninase was developed and entered primate pre-clinical studies, which also failed to show durable depletion.

Eventually, it was found that the short duration of methionine depletion was due to inactivation of enzyme through rapid loss of the cofactor, pyroxidal-5'-phosphate (PLP), to blood proteins. When PLP is supplied at super-physiological levels by a mini osmotic pump, as studied in mouse studies, the enzyme activity was restored, which supported the reason that rapid loss of activity was, in fact, cofactor loss. PLP, also called vitamin B6, is covalently bound to a lysine side chain of enzyme. During catalytic interaction of methionine with methioninase, PLP is transferred to methionine re-associating with the enzyme following the resolution of the $\alpha$, $\gamma$ elimination reactions. However, due to the high affinity of PLP to human albumin, PLP is sequestered by albumin and become unavailable for the enzyme causing rapid loss of activity.

I.2.2. Encapsulation of Methioninase within SHELS (metSHELS)

Encapsulation of methioninase can have a number of benefits. For example, encapsulation would protect methioninase from immune response, similar to asparaginase. Second, encapsulation will not only prevent the access of antibodies to the enzyme, but also access of albumin to the enzyme. Also for example, the exemplary SHELS nanoparticle platform can create an environment in where there is a high concentration of enzymes and PLP without albumin. Moreover, for example, PLP loss may be reduced because when PLP is released, it is more likely to be captured by another methioninase before it leaves the hollow interior of the SHELS structure. In addition, the negatively charged nature of SHELS can also reduce the diffusion of negatively charged PLP through the shell, therefore confine PLP within the particle in higher concentrations.

Figure 5:
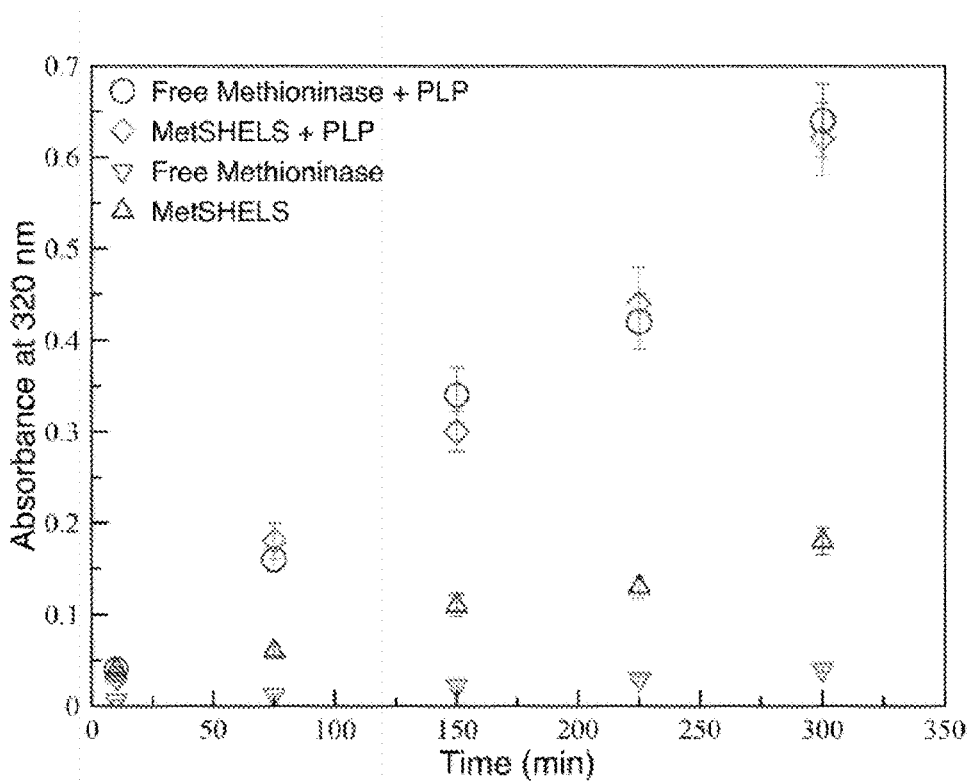
FIG. 5 shows a plot depicting exemplary data of in vitro activity of free and methioninase encapsulated SHELS (met-SHELS).

Exemplary implementations were performed using methioninase encapsulated within SHELS (metSHELS). FIG. 5 shows a plot depicting exemplary data of in vitro activity of free and methioninase encapsulated SHELS (metSHELS). Recombinant methioninase was produced from a custom expression vector. Methioninase in the exemplary metSHELS retained its bioactivity in the reaction media including PLP with a concentration of 10 µM. For example, activity was measured by the production α-ketobutyrate that has an absorbance at 320 nm. Furthermore, in the absence of additional PLP in the reaction media, the encapsulated methioninase enzyme retained considerably more activity. This result supports that having a high concentration of enzyme within the hollow interior of the disclosed SHELS nanostructure can reduce extensive diffusion of PLP out of the interior. In the data plot, reaction with free methioninase in the absence of additional PLP is represented by down triangles; reaction with metSHELS in the absence of additional PLP is represented by up triangles; reaction with free methioninase in the presence of 10 µM PLP is represented by circles; and reaction with metSHELS in the presence of 10 µM PLP is represented by diamonds.

Figure 6:
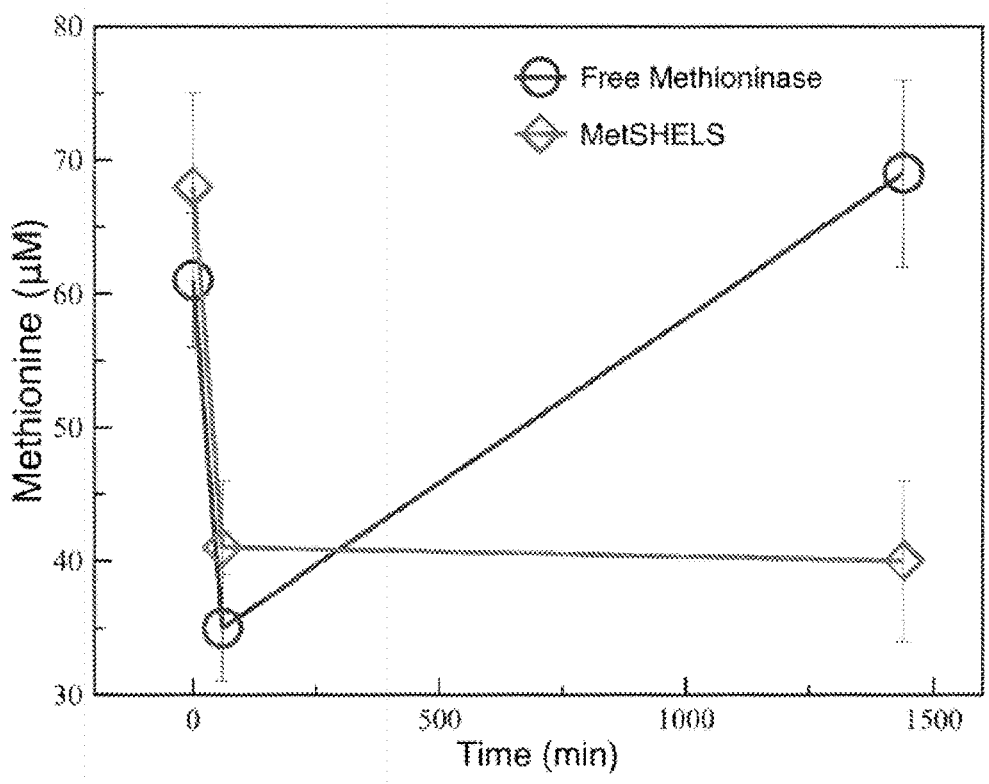
FIG. 6 shows a plot depicting exemplary data of in vivo methionine depletion in naïve mice.

The exemplary implementations included an evaluation of in vivo activity of metSHELS compared with an equivalent dose of free methioninase. FIG. 6 shows a data plot depicting exemplary data of in vivo methionine depletion in naïve mice. Mice were injected intramuscularly and serum methioninase measured over time. A dose of 1.5 IU (international units) of free methioninase (circles) of activity and 0.75 UI metSHELS (diamonds) were injected intramuscularly into left flank of naïve mice. Serum was collected pre and post injection at 60 minutes and 24 hours and methioninase level in serum was measured. Exemplary error bars in FIG. 6 represent standard deviations. In this example, as shown in FIG. 6, the exemplary metSHELS with an activity of 1.5 UI maintained a roughly 50% depletion of methionine, whereas the same depletion initially produced by the free enzyme with 3 UI was no longer seen after 24 hours even in the case. The exemplary results demonstrated sustained methionine depletion using metSHELS for 24 hours, which suggests that PLP loss is abrogated by the metSHELS.

It is noted that the methioninase used in these exemplary implementations was purified and stored with 10 µM PLP such that all of the methioninase enzyme was a holoenzyme with bound PLP. For example, PLP can be lost as a reaction proceeds if there is no supplemental cofactor present in the local environment. Yet, such loss of cofactor is prevented or at least substantially reduced in SHELS. The SHELS structure can allow for loading of apoenzymes and their cofactors (e.g., loaded together individually and/or together pre-bound, and/or loaded separately) to create the holoenzymes within the SHELS. In one example, the apoenzyme can be loaded through the holes or mesopores 112, while the cofactor can be loaded through the pores 113 of the sealed shell structure 101.

Figure 7:
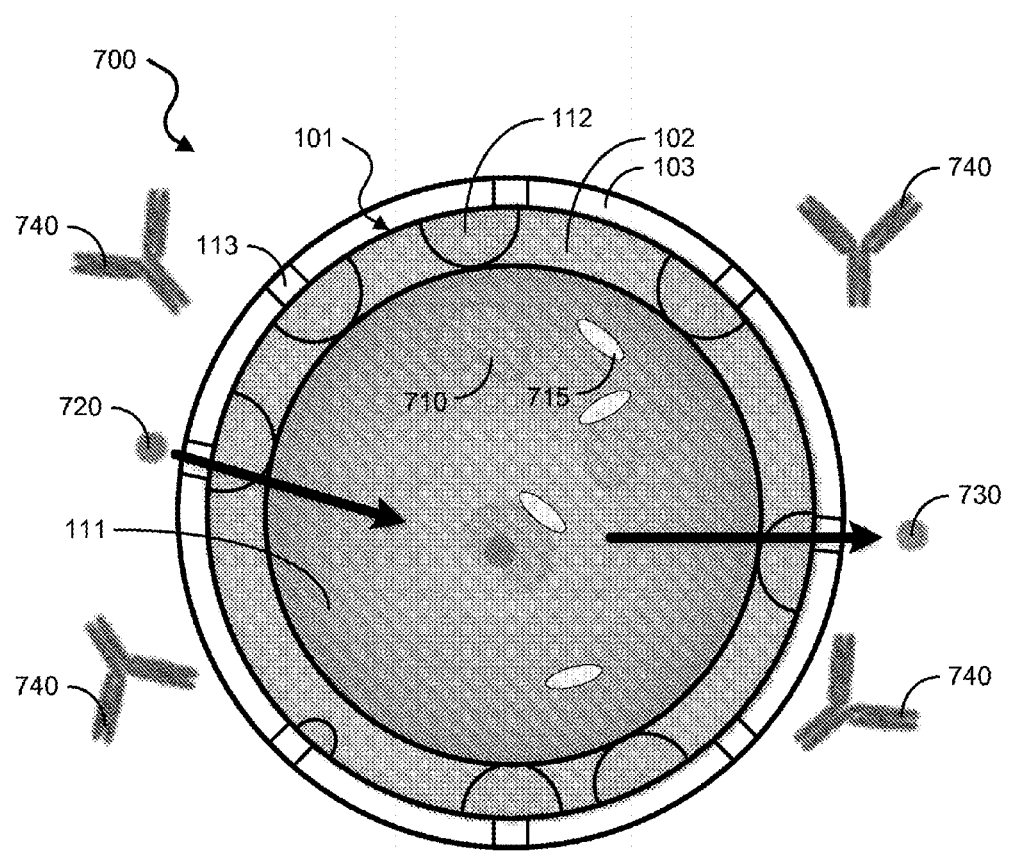
FIG. 7 shows a diagram of an exemplary synthetic hollow enzyme and cofactor encapsulating nanosphere (SHECENS) particle structure.

FIG. 7 shows a diagram of an exemplary synthetic hollow enzyme and cofactor encapsulating nanosphere (SHECENS) particle 700 that encapsulates an enzyme 710 and a cofactor 715 to the enzyme 710 within the SHECENS particle, such that the enzyme 710 and the cofactor 715 are both bioactive and protected from nonspecific binding. The SHECENS particle 700 includes the shell structure 101 that includes the internal layer 102 and the external layer 103, in which the internal layer 102 is structured to include holes or mesopores 112 penetrating through the internal layer 102 and enclose the hollow interior region 111, and in which the external layer 103 is formed around the internal layer 102 and structured to include the pores 113 of a size smaller than the encapsulated enzyme 710 that permit diffusion and/or other types of particle-transfer of small molecules through the pores 113 while preventing the encapsulated enzyme 710 to pass through the pores 113. Such small molecules of a size less than the size of the pores 113 can transfer into the hollow interior region 111. For example, such small molecules can include enzyme substrates 720 that react upon interaction (e.g., binding) with the encapsulated enzyme 710 and become modified by the enzyme 710, e.g., forming a new product 730. The SHECENS nanoparticle 700 also protects the encapsulated enzyme 710 from antibody binding, as antibodies 740 are not capable of penetrating into the SHECENS nanoparticle 700. In some implementations, for example, the SHECENS particle 700 can also include the charged material layer formed in mesopores 112 to provide an electrostatic force to prevent enclosed substances (e.g., such as the enzymes 710 and/or the cofactor 715) from exiting the interior region 111.

Implementations of the SHECENS particle 700 can include methioninase as the encapsulated enzyme 710 and PLP as the encapsulated cofactor 715. In some implementations, for example, the SHECENS particle 700 can first be loaded with the exemplary methioninase enzyme 710 through the holes 112 prior to forming the external layer 103, and the exemplary PLP cofactor 715 can be loaded through the pores 113 of the external layer 103. Whereas, in some implementations, for example, the SHECENS particle 700 can be loaded with the exemplary methioninase enzyme 710 and the exemplary PLP cofactor 715, either pre-bound together, individually, or both, via the holes 112 prior to forming the external layer 103. For example, the cofactor can be pre-bound to the enzyme, and in addition, the cofactor can also be constantly in solution during enzyme loading and formation of the external layer; therefore, one can achieve a given concentration within the particle eventually. For example, the negatively charged nature of the exemplary shell structure of can also reduce the diffusion of negatively charged PLP through the shell structure, and therefore confine the PLP within the particle in higher concentrations. Furthermore, for example, in implementations of the SHECENS particle 700 including nanoporous silica, the exemplary PLP cofactor 715 can be attached within a silica gel matrix formed within the interior region 111 of the SHECENS particle 700, which would be slowly released for constantly supplying the enzyme 710 (e.g., methioninase) with the exemplary PLP cofactor 715, e.g., in a controlled rate and manner.

I.3. Uricase Encapsulated within SHELS: uriSHELS

I.3.1. Background of Uricase, Gout, and Uricase Based Therapies for Treatment of Refractory Gout Gout Gout is a type of inflammatory arthritis that is triggered by the crystallization of uric acid within the joints, tendons and surrounding tissues. If the concentration of uric acid exceeds the solubility limit in plasma and extracellular fluids, monosodium urate crystals are formed leading to gout. Currently up to 3.9% of adults suffer from gout in the United States.

Conventional, frontline treatment of gout involves maintaining serum urate below the solubility limit of 7 mg/mL using drugs inhibiting xanthine oxidase, the enzyme that catalyzes xanthine to uric acid, or promoting renal urate excretion. However, frontline treatment fails for 30,000-120,000 patients out of 8.3 million that suffer from gout (in the United States) due to noncompliance, intolerance, inadequate dosage, or inefficacy.

Gout has radically altered in clinical complexion over the last two decades in the United States, due to large numbers of cases with iatrogenic factors, multiple co-morbidities, advanced age, and with hyperuricemia and tophaceous, destructive arthropathy and inflammatory arthritis refractory to treatment. Treating gout flares is expensive and fraught with risks of NSAID, colchicine, and corticosteroid side effect risks. Better strategies and recent evolution in the evidence basis to employ allopurinol, febuxostat, probenecid, and anti-inflammatory agents have validated cost-effective treatment strategies for the average patient. However, gout refractory to all standard uric acid lowering therapy (ULT) is common, and the severe subset of chronic tophaceous gouty arthropathy is estimated as 50 to 200 thousand cases in the United States, and at least as disabling as rheumatoid arthritis in many patients, and far more painful.

Humans are susceptible to gout because they do not express uricase enzyme that degrades uric acid to allantoin. Recently, non-human uricases are being employed to lower urate levels in blood. For example, FDA approval of the recombinant PEGylated porcine-baboon uricase (pegloticase) has provided a substantial and unique advance in treatment for severe, treatment-refractory gout, particularly for those with intolerance to other drugs used in gout or with co-morbidities that include CKD, where effectiveness and tolerance of allopurinol and other oral ULT agents are decreased. PEGylation of uricases does suppress immunogenicity and increases half-life, and allows uricase to work remarkably well in those who maintain drug response. Specifically, in pivotal phase 3 clinical studies in subjects with particularly severe gout (70% with visible tophi), intravenous pegloticase treatment (8 mg every 2 weeks) achieved target serum urate <6 mg/dL at 6 months in 42% (intent to treat analysis), and this regimen also achieved complete resolution of one or more tophi in 20% by 13 weeks and 40-45% by 25 weeks. Concordantly, overall improvement in health related quality of life (HRQOL) is markedly improved in sustained pegloticase responders. This compares favorably to HRQOL, and American College of Rheumatology 70% (ACR70) response and remission response rates, using biologics including anti-TNF drugs in rheumatoid arthritis. As such, successful uricase therapy provides a major clinical advance for patients with the most severe and incapacitating chronic tophaceous gouty arthropathy, and is recommended as an option for severe forms of treatment-refractory gout in the ACR gout treatment 2012 guidelines.

However, due to their foreign origin, FDA-approved uricase therapies for tumor lysis syndrome prevention (non-PEGylated IV rasburicase) and pegloticase for gout management are hugely limited by the antigenicity of the foreign uricase enzyme tetramer, including PEGylated uricase. Antibodies to the recombinant PEGylated porcine-baboon uricase (pegloticase) develop within a few months in about 89% of the patients, and this mandates use of high dose corticosteroids prior to infusion to limit infusion reactions. In almost half of the patients with a high anti-pegloticase antibody level, pegloticase does not show any efficacy. Furthermore, infusion reactions correlated with the production of these antibodies. The anti-pegloticase antibodies in many patients are IgG2 and are specific to PEG. Thus there is still a considerable need for a therapeutic option for the majority of chronic gout sufferers.

For example, in the phase III study, infusion reactions were observed in more than a quarter of subjects, and were classified as moderate to severe in 10% of subjects, and included anaphylaxis. Treatment-emergent antibodies to pegloticase negatively impacted on both pharmacokinetics and pharmacodynamics overall.

I.3.2. Encapsulation of Uricase within SHELS (uriSHELS)

Sustained activity of provided by uricase encapsulated within SHELS (uriSHELS) nanostructures of the disclosed technology can prevent or at least substantially reduce anti-uricase antibody mediated clearance and treatment failure while maintaining urate in blood below solubility limit. Similar to the exemplary asparaginase-encapsulated SHELS, intramuscularly administered uriSHELS offer a more manageable circulation and distribution behavior compared to pegloticase. At the same time, since antibody production does not cause rapid clearance of the uriSHELS, unlike pegloticase, and the uriSHELS can allow effective treatment with a reduced amount of enzyme used and reduced number of injections, thus, achieving a better quality of life for patients. Also, for example, conversion of endogenous plasma uric acid to hydrogen peroxide at the site of a diseased tissue, e.g., such as cancer tumors, where the locally produced hydrogen peroxide creates a therapeutic effect, such as causing the death of cancer cells. Uricase protected within SHELS devices would be protected from degradation in diseased tissue.

II. Exemplary Diagnostic Biomedical Applications of SHELS

II.1. Catalase Encapsulation within SHELS for In Vivo Hydrogen Peroxide Sensing

Reactive oxygen species (ROS) are chemically reactive molecules containing oxygen. In living organisms, ROS are formed as a natural byproduct of the normal metabolism of oxygen and have important roles in cell signaling and homeostasis. However, during times of environmental stress (e.g., UV or heat exposure), ROS levels can increase dramatically and result in significant damage to cell structures, known as oxidative stress. Some examples of ROS include oxygen ions and peroxides. For example, hydrogen peroxide ($H_2O_2$) is the simplest form of a peroxide that plays an important role in mediating the damage caused by inflammation, cancer, diabetes, aging, and cardiovascular disease.

Ultrasound refers to sound waves operating at frequencies higher than that of the upper level of typical human hearing. Ultrasound signals can be used in a variety of biomedical and other applications for imaging and therapeutic purposes. For example, ultrasound imaging (also referred to as sonography) is a medical imaging modality that employs the properties of sound waves traveling through a medium to render a visual image of internal structures and functions of animals and humans. Ultrasound imaging can include contrast enhanced ultrasound, which utilizes a contrast medium to enhance an ultrasound image. For example, ultrasound contrast agents can reflect the ultrasound waves in a variety of ways from interfaces between the agents and this ability of reflecting the ultrasound waves of such agents is measured by the degree of echogenicity. Ultrasound contrast agents can include gas-filled micro-sized bubbles (microbubbles) that have a greater degree of echogenicity with respect to the surrounding tissue. For example, microbubbles can be used as ultrasound contrast agents to enhance the reflection of the ultrasound waves and produce a higher resolution image due to the high echogenicity difference. However, microbubble ultrasound contrast agents can have short in vivo circulation times, poor tissue extravasation, and short-lived ultrasound signal contrast enhancement due to their instability, e.g., rapid dissolution or coalescence resulting in larger microbubbles that provide little to no signal enhancement in standard contrast-sensitive modes of diagnostic ultrasound imaging systems.

Due to its widespread clinical use and low detection threshold for small gas-filled microbubbles, ultrasound can be used as a modality for clinical detection of pathophysiologic hydrogen peroxide, and catalase-based precursor molecules can be used in several settings for local generation of oxygen microbubbles in vitro and in vivo applications.

In some aspects of the disclosed nanoparticle platform, exemplary silica-based nanoparticles are described to operate as sensors for $H_2O_2$. Such nanoparticle $H_2O_2$-sensors can be designed to appropriate size and configuration for injectable in vivo applications. In one example, a nanoparticle $H_2O_2$-sensor of the disclosed technology can include synthetic enzyme-loaded nanospheres (SHELS) particles that encapsulate an enzyme that interacts with $H_2O_2$ for local production of oxygen microbubbles.

Figure 8D:
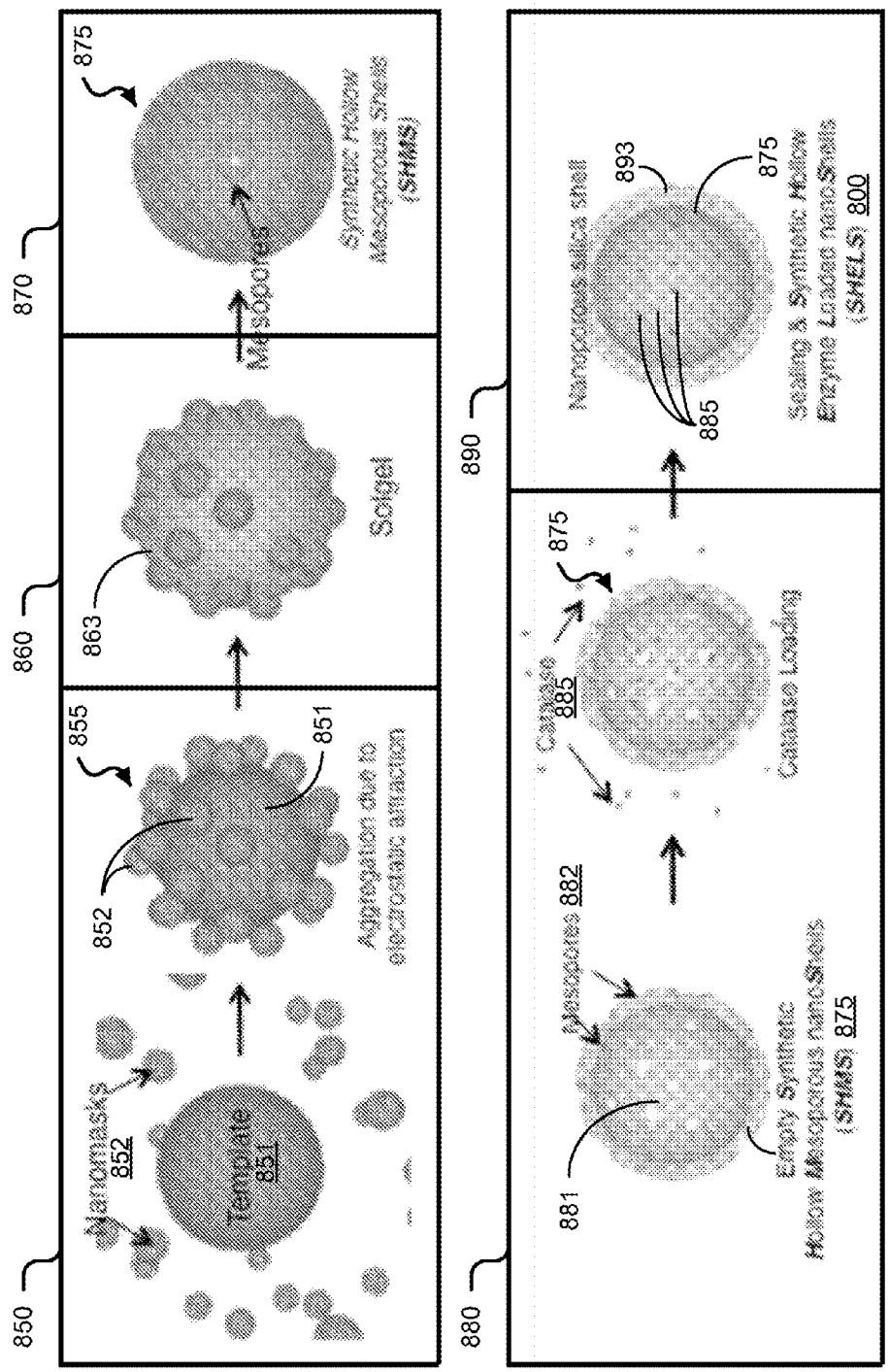
FIG. 8D shows a schematic illustration of an exemplary fabrication method to synthesize exemplary catSHELS.

FIGS. 8A-8D show schematic illustrations and images of exemplary catalase-loaded SHELS (catSHELS) structures and their synthesis. FIG. 8A shows a schematic illustration of an exemplary catSHELS structure 800 capable of causing the breakdown of $H_2O_2$ that enters the interior region of the SHELS structure encapsulating the catalase to produce oxygen microbubbles that exit the SHELS structure in the local environment. The exemplary catSHELS structure 800 can be configured to have a similar structure as the SHELS particle 100 shown in FIG. 1. For example, as shown in FIG. 8A, the exemplary catSHELS structure 800 includes a shell structure 101 including an internal layer 102 and an external layer 103. The internal layer 102 is structured to include holes or mesopores 112 penetrating through the internal layer 102 and enclose a hollow interior region 111. The external layer 103 is formed around the internal layer 102 and structured to include pores 113, in which at least some of the pores 113 penetrate through the external layer 103. The catSHELS nanostructure 800 can be loaded with the enzyme catalase 810, which is contained within the interior region 111 of the shell structure 101, by which the catalase enzyme 810 is loaded in the interior region 111 through the holes 112 prior to forming the external layer 103 over the internal layer 102, and is incapable of passing through the pores 113 of the external layer 102. While the catalase enzymes 810 encapsulated within the hollow core of the catSHELS particle 800 cannot escape, small molecules like $H_2O_2$ 820 having a size less than the size of the pores 113 can diffuse through the shell structure 101 of the catSHELS particle 800 and interact with the catalyze enzyme 810, where the catalase enzymes 810 cause the breakdown of the $H_2O_2$ molecules to form oxygen and water inside the interior region 111 of the shell structure 101. The produced oxygen forms oxygen microbubbles 130, which can diffuse out of the shell structure 101 and in the local outer environment. Additionally, the catSHELS particle 800 shields the catalase enzyme 810 from degradation by external proteases while allowing free diffusion of hydrogen peroxide. In some implementations, for example, the catSHELS particles 800 can be configured as porous silica particles.

In some implementations of the catSHELS particles 800, for example, the interior surface of the internal layer 102 facing the interior region 111 can be structured to include nanoscale features 815. For example, such nanoscale features can include a rough surface structure or include nanoscale structures, e.g., such as nanowires and/or small nanoparticles (e.g., such as gold nanowires or nanoparticles) protruding from the interior surface inwardly toward the interior. Such nanoscale features can further improve and initiate cavitation of oxygen bubbles by the catSHELS structure 800.

FIGS. 8B and 8C show scanning transmission electron microscopy (STEM) and scanning electron microscopy (SEM) images of exemplary fabricated catSHELS. As shown in FIG. 8B, the STEM micrograph features exemplary 200 nm catSHELS taken by secondary electron mode. As shown in FIG. 8C, the SEM micrograph features exemplary 200 nm synthetic hollow mesoporous nanospheres (SHMS).

In some implementations, for example, exemplary catSHELS can be configured to be between 100 nm to 500 nm in diameter and designed such that large molecular weight enzymes are trapped inside hollow interiors of nanoporous silica shells. Small molecular substrates can still diffuse through nanoporous shell and access encapsulated enzymes without the need for releasing and exposing the payload. For example, catalase enzymes are encapsulated within the catSHELS particles to produce an in vivo hydrogen peroxide sensor. Catalase is a well-characterized enzyme that turns hydrogen peroxide into water and oxygen. Once the local concentration of oxygen produced as a result of the catalysis of environmental hydrogen peroxide with encapsulated catalase exceeds the solubility threshold, the nanoporous surface of the SHELS structure acts as a nucleation site for oxygen microbubble formation. Also, for example, implementations of the catSHELS structures in the biological system to catalyze hydrogen peroxide can cause a high concentration of oxygen that exceeds the solubility limit of oxygen in the local environment and produce the oxygen microbubbles.

The disclosed SHELS structures can be fabricated by first utilizing a template-based fabrication method referred to here as nanomasking that yields empty dual-scale-porosity nanoparticles that form the internal layer 102 of the shell structure 101, which is also referred to as synthetic hollow mesoporous nanospheres (SHMS). In some examples, SHMS can be made of nanoporous silica and produced through a template-based nanofabrication method (e.g., nanomasking). In nanomasking, for example, the blocking materials (e.g., nanomasks) prevent the growth reaction on parts of the surface of template nanoparticles and act as masks to create mesopore features on the surface of the shell after removal of templates and nanomasks. Later, enzymes (e.g., such as catalase) are filled into the hollow interior of the exemplary SHMS structures through the mesopores. The external layer 103 of the shell structure 101 can be formed by coating a material, e.g., a porous material, over the SHMS structures, in which the loaded enzymes are thereby shielded from interfering blood proteins and proteases once the mesopores are sealed with a new layer of nanoporous silica yielding the SHELS particles.

FIG. 8D shows a schematic illustration of this exemplary fabrication method to synthesize exemplary SHELS particles, e.g., such as catSHELS. The method includes a process 850 to form a nanomask structure 855 by attaching nanomasking particles 852 on the outer surface of a template particle 851. For example, the nanomasking particles 852 can attach to the template particle 851 by aggregating to its outer surface through electrostatic interaction. In some implementations, for example, the template particle 851 can include aminated functional groups creating a positively charged surface, and the nanomasking particles 852 can include carboxylated functional groups that have a negatively charged surface. Such carboxylated nanomasking particles 852 can repel negative ions and prevent sol-gel reaction on their surfaces, e.g., which can provide blocking of some positively charged regions of the outer surface of the exemplary aminated template particle 851. In some implementations, the nanomasking particles 852 can be attached to the template particle 851 by other particle attraction schemes, e.g., including, but not limited to, hydrogen bonding, covalent bonding, magnetic attraction, hydrophobic interactions, etc. In some implementations, for example, the process 850 can be performed in a mixed solution containing a solution of the template particles 851 and a solution of the nanomasking particles 852. For example, the nanomasking particles 852 prevent growth reaction on parts of the surface of template nanoparticles 851 in subsequent processes of the method.

The method includes a process 860 to form a coating layer 863 over the nanomask structure 855. The process 860 can produce the coating layer 863 to cover the exposed surface of the template particle 851 while not covering locations on the template particle 851 where the nanomasking particles 852 are present. For example, the coating layer 863 can include a porous material, e.g., such as silica, to produce a porous coating layer 863. In some implementations of the process 860, for example, sol-gel reagents can be added to the solutions containing the nanomask structures 855. For example, sol-gel reactions can be controlled to occur only in the positively charged regions along the surface of the template particle 851, e.g., the regions that are not covered or blocked by the nanomasking particles 852. For example, addition of sol-gel reactants in the process 860 can initiate silica growth, e.g., rooted from the amino groups of the exemplary aminated functionalized surface of the template particle 851. In other implementations, for example, the process 860 can include adding the coating layer 863 to the nanomask structure 855 by other techniques, e.g., including material based exclusivity, or redox chemistry. In other examples, the coating layer 863 can be a non-porous material or a degradable material that can dissolve or degrade in certain environments or under particular conditions or by an exemplary trigger, e.g., including pH, temperature, pressure, molecular interaction, etc.

The method includes a process 870 to form a dual-scale porosity nanoparticle 875, the SHMS particle, by removing the nanomask structure 852 such that the coating layer 863 remains and forms the SHMS particle. In some implementations of the process 870, for example, the template particle 851 and the nanomasking particles 852 are removed by calcination. In some implementations of the process 870, for example, the nanomask structure 855 can be removed by other various techniques including dissolving them by solvents, melting, or burning, or a combination of these or other similar methods. In one example, the process 870 can include introducing dimethylformamide (DMF), acetone, or other solvent and/or heat to the coating layer 863-covered nanomask structure 855.

The method includes a process 880 to load enzymes 885, e.g., such as catalase, into the hollow interior region 881 of the SHMS particle 875 through the mesopores 882 that are formed on the structure of the SHMS particle 875. In some implementations of the process 880, for example, a solution of the enzyme 885 can be added to a solution of the SHMS particles 875. The process 880 can be implemented by one of several techniques. For example, the enzymes 885 can diffuse into the hollow, mesoporous shell structure of the SHMS particles through the mesopores 882. In another example, the enzymes 885 can enter the hollow interior region 881 of the SHMS particle 875 by electrophoretic forces.

The method includes a process 890 to form an outer coating layer 893 on the SHMS particles 875 encapsulating the enzymes 885 to produce a SHELS structure, e.g., the catSHELS particle 800. For example, the external coating layer 893 can include nanoporous material, e.g., such as silica, yielding the exemplary catSHELS particle. In some implementations of the process 890, for examples, the mesopores 882 (e.g., holes) of the SHELS structure 800 can be sealed with a further outer layer of a non-porous material, e.g., including a metal.

In implementations of the catSHELS for in vivo diagnostic applications, e.g., including ultrasound imaging of the exemplary $H_2O_2$ sensor catSHELS, the individual microbubbles produced by catSHELS can be detected using standard clinical ultrasound technology at depths of up to 20 cm in tissue using specialized pulses that elicit and detect non-linear oscillations of microbubbles, thereby molecularly sensing the presence of hydrogen peroxide. For example, the oxygen microbubbles are typically short-lived (e.g., such as sub-seconds to a few seconds), e.g., which allows for real-time analysis of the effects of the deployed $H_2O_2$ sensor catSHELS. The disclosed catSHELS can be made small enough for in vivo injection (e.g., including configured to a 50-200 nm size range) and can be made to be biodegradable.

Figure 9A:
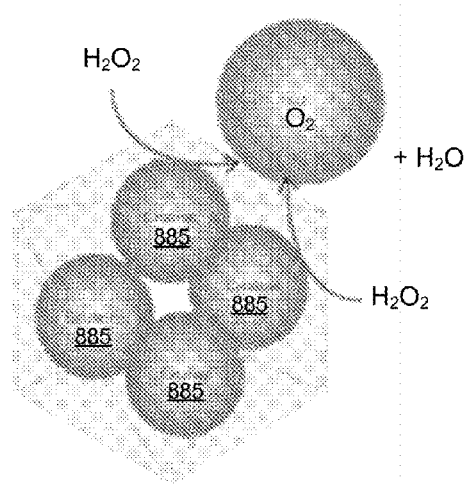
FIGS. 9A-9C shows diagrams and images depicting implementation of exemplary $H_2O_2$ sensor catSHELS to cause oxygen microbubble accumulation in response to environmental hydrogen peroxide.
Figure 9B:
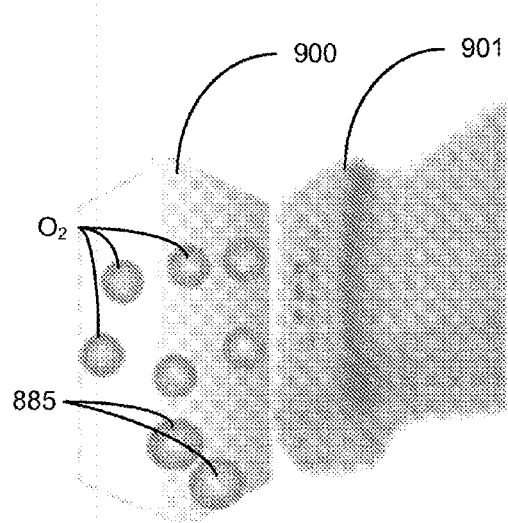
Figure 9C:
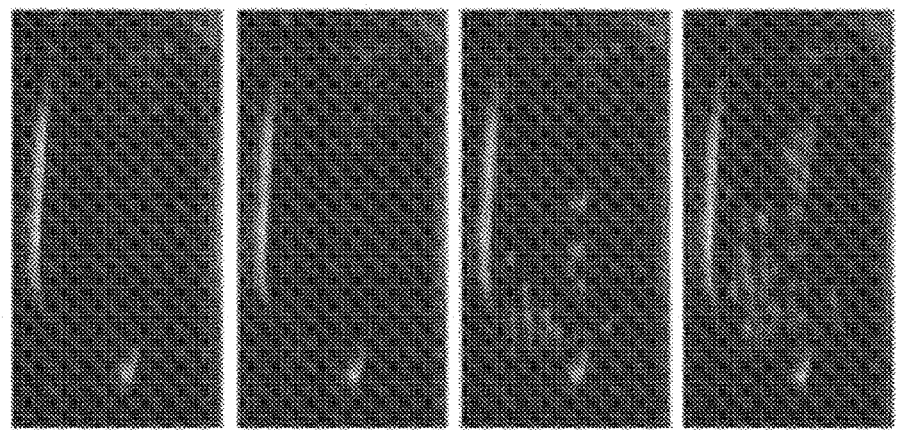

FIGS. 9A-9C shows diagrams and images depicting implementation of exemplary $H_2O_2$ sensor catSHELS to cause oxygen microbubble accumulation in response to environmental hydrogen peroxide. FIG. 9A shows a illustrative diagram depicting how catalases trapped inside SHELS structures that are porous to $H_2O_2$ break down the $H_2O_2$ that have entered the SHELS structure (e.g., by diffusion through the porous outer layer of the shell structure) to produce oxygen that aggregates to form oxygen microbubbles. FIG. 9B shows an illustrative diagram (not drawn to scale) depicting how, upon sufficient $H_2O_2$ in the surrounding milleau, oxygen microbubbles are formed at the surface of an exemplary catSHELS structure 900 that are detectable by an ultrasound transducer 901. FIG. 9C shows multiple frames of ultrasound images showing rising gas-filled microbubbles following injection of $H_2O_2$ through a side port, allowing differentiation from surrounding echogenic material. For example, in an exemplary implementation, the exemplary catSHELS were initially injected in solution. Once the catSHELS settled in the bottom of the tube, $H_2O_2$ was injected in solution. As a result of the interaction of the catSHELS and $H_2O_2$, $O_2$ bubbles were produced originating from the bottom of the tube. The oxygen bubbles eventually disappeared as oxygen dissolves in solution while the bubble is rising.

II.1.1. Exemplary Implementations of the catSHELS Hydrogen Peroxide Sensor

Figure 10A:
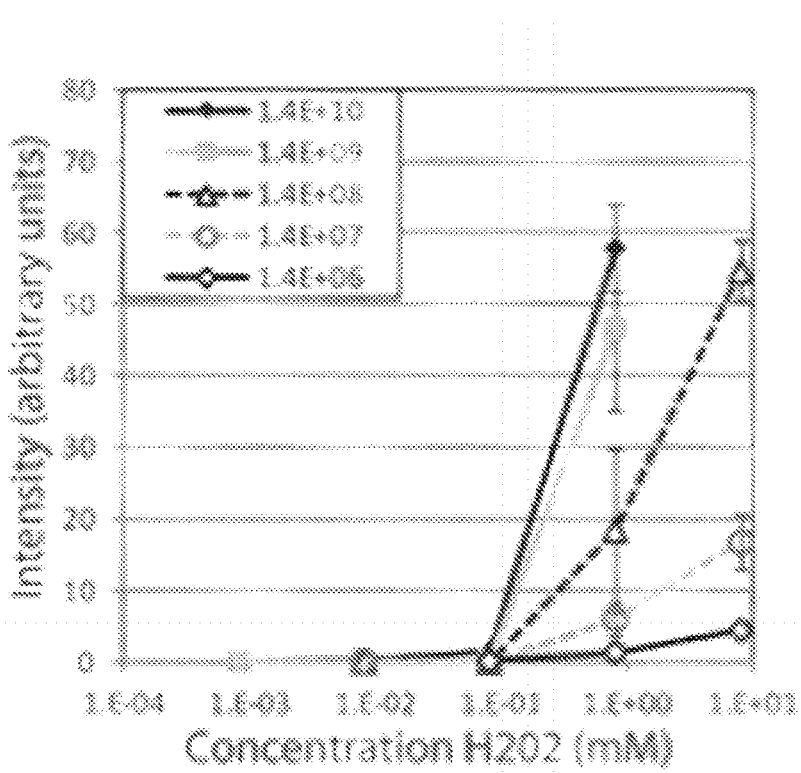
FIGS. 10A-10D show plots of exemplary data depicting the dependence of microbubble formation on particle size, enzyme concentration, and particle number.

Exemplary implementations of exemplary $H_2O_2$ sensor catSHELS were conducted in a series of in vitro tests performed in buffer to determine the effect of the exemplary catSHELS's size, interior catalase concentration, and total catSHELS concentration on microbubble formation. FIGS. 10A-10D show plots of exemplary data depicting the dependence of microbubble formation on particle size, enzyme concentration, and particle number. FIG. 10A shows a data plot depicting the effect of increasing hydrogen peroxide concentration on ultrasound signal intensity for decreasing particle number. In the exemplary implementation, the exemplary catSHELS particle size was held constant at 200 nm, and concentration was held constant at 80 mg/mL. As demonstrated by the exemplary results shown in FIG. 10A, an increasing the number of catSHELS, while holding the interior catalase concentration and size constant, resulted in higher echogenicity on ultrasound due to increased microbubble formation.

Figure 10B:
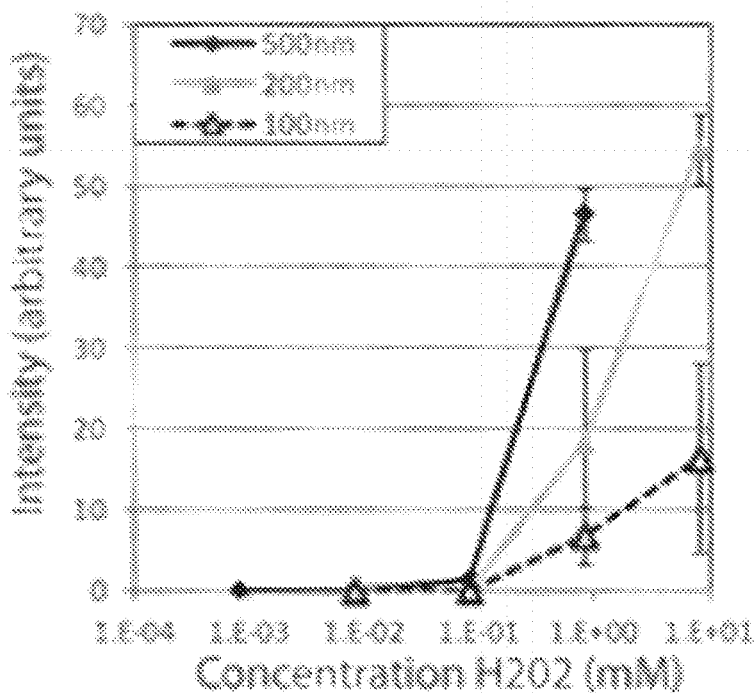

FIG. 10B shows a data plot depicting the effect of particle size on total ultrasound signal. For these exemplary implementations, the particle concentration was held constant at 80 mg/mL, and the particle number was held constant at $1\times10^8$. As demonstrated by the exemplary results shown in FIG. 10B, increasing the exemplary catSHELS particles' size also resulted in more signal when the particle number and catalase concentration were held constant.

Figure 10C:
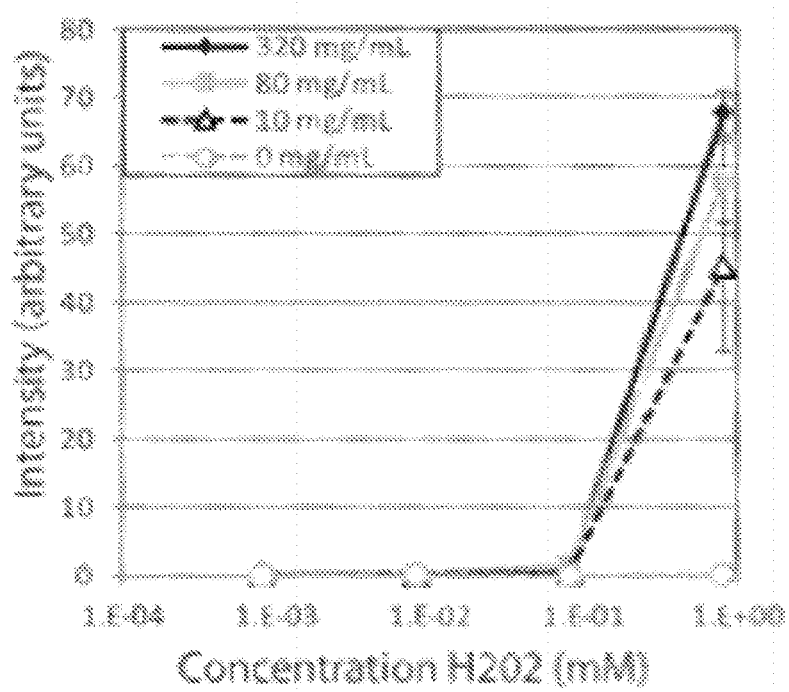

FIG. 10C shows a data plot depicting the effect of catalase concentration on total ultrasound signal. For these exemplary implementations, the particle number was held constant at $1\times10^8$, and the particle diameter was held constant at 200 nm. As demonstrated by the exemplary results shown in FIG. 10C, while increasing the interior catalase concentration from 10 mg/mL to 80 mg/mL did have an effect on total signal, a further increase in the interior catalase concentration from 80 mg/mL to 320 mg/mL did not have a substantial effect. For example, this may be due to a combined effect of decreased catalase adjacent to nucleation sites on the exterior of the molecule and relative paucity of $H_2O_2$ perfusion.

Figure 10D:
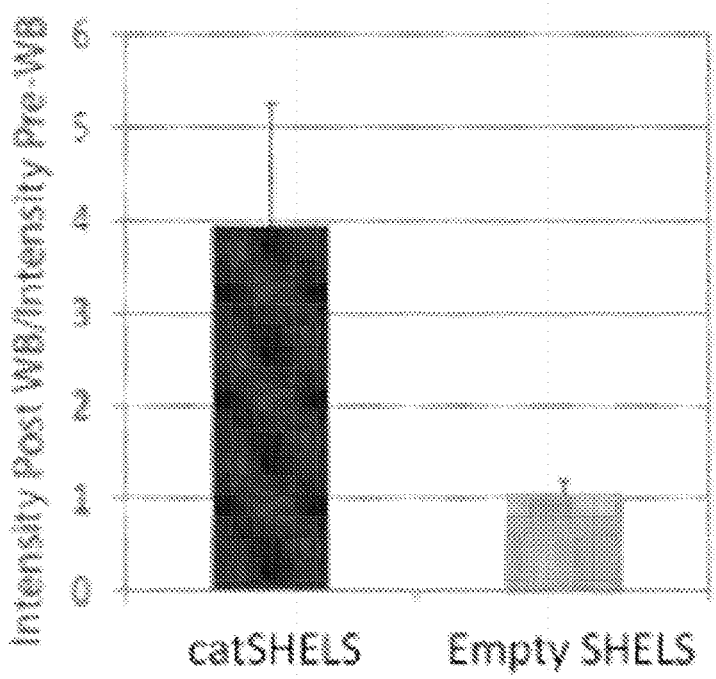

FIG. 10D shows a data plot depicting a comparison of signal from $1.4\times10^{10}$ 200 nm catalase (80 mg/mL)-SHELS and empty SHELS in rabbit plasma at increasing $H_2O_2$ concentrations. These exemplary implementations were done in triplicate, and the exemplary error bars shown in FIG. 10D represent standard error of the mean. As demonstrated by the exemplary results shown in FIG. 10D, the detection limits were yet lower when performed in rabbit plasma.

Figure 11A:
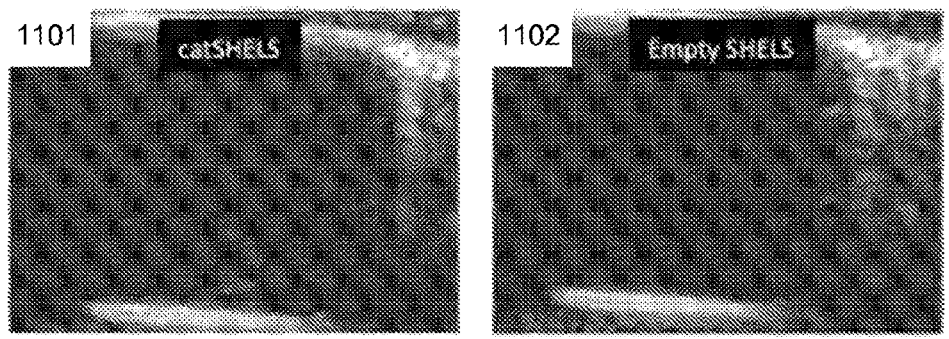
FIGS. 11A-11C show images and plots of exemplary data depicting endogenous hydrogen peroxide from human abscess fluid is detectable by exemplary catSHELS ex vivo.

Exemplary implementations of exemplary $H_2O_2$ sensor catSHELS were conducted to demonstrate whether sufficient hydrogen peroxide could be produced by human neutrophils to activate the catSHELS. Abscess fluid was collected from 12 patients and used within 24-72 hours of drainage. The abscess fluid was first centrifuged to reduce potentially echogenic debris and reduce viscosity. Among 11 abscess specimen collected, eight were sufficiently non viscous for in vitro testing of catSHELS. Microbubbles were seen in 4/8 abscesses when exemplary 200 nm catSHELS with 80 mg/mL interior catalase were added to a final catSHELS concentration of 1.4-10 M, as shown in image 1101 of FIG. 11A. The exemplary specimens were collected, divided into 2 mL aliquots and added to non PEGylated catSHELS or empty SHELS, e.g., 200 nm, 80 mg/mL or 0 mg/mL catalase. FIG. 11A shows image data in the image 1101 from test abscesses where exemplary catSHELS were deployed, and image data in the image 1102 where empty SHELS were deployed. No microbubbles were observed in the control abscesses group.

Figure 11B:
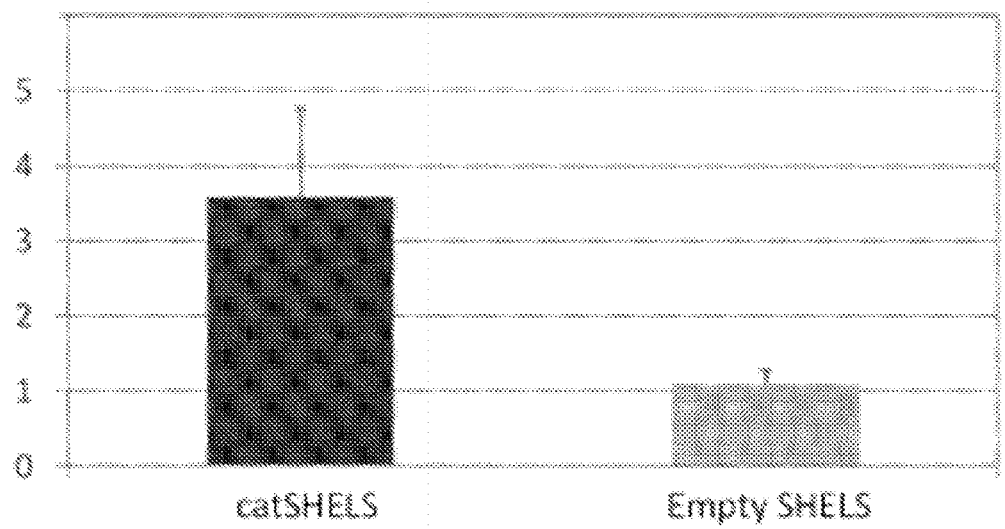
Figure 11C:

As shown in FIG. 11B, quantitative analysis showed a 3.6-fold difference in total signal from abscess fluid added to catSHELS versus empty SHELS (n=4, p=0.02). As shown in FIG. 11C, independent quantification of $H_2O_2$ concentration using established optical techniques was stymied by the broad spectral absorption of hemoglobin, present to varying degrees between samples. A 200 nm size of the exemplary catSHELS was chosen for these exemplary implementations based on the ease of synthesis and being of sufficiently small size for systemic injection. Of the four abscess fluid samples that were tested from four different abscesses and deemed to be positive at the time of the test, the ratio of signal before to signal after catSHELS addition was 3.6±1.2 for the catSHELS and 1.1±0.2 for the control SHELS. Of the remaining four abscesses, two yielded limited supernatant and were highly echogenic prior to addition of catSHELS, limiting the ability to detect new microbubbles and the other two samples did not yield bubbles upon addition of cat-SHELS. Unfortunately attempts at quantifying the hydrogen peroxide concentration in the abscess fluids themselves met with limited success, since the presence of heme interferes with conventional spectroscopic techniques (FIG. 11C). However given the frequent contamination of body fluids with blood products, this highlights the potential clinical utility of catSHELS as even spectrally clear samples such as urine are frequently contaminated with blood.

The disclosed enzyme-encapsulated nanoparticle platform provides a new method for visualizing the presence of hydrogen peroxide in tissue. The exemplary $H_2O_2$ sensor SHELS structures can provide several advantages and features, e.g., including: (1) SHELS can be doped with small amounts of iron or other paramagnetic agents so that they biodegrade more rapidly; (2) catalase is protected from outside proteases; (3) compounds can be PEGylated, and/or targeting moieties can be added for improved in vivo biodistribution; (4) the pores of the SHELS structures create increased nucleation sites for microbubbles; and (5) SHELS can be loaded with catalase in very high concentrations (e.g., around 100-200 mg/ml interior concentration of SHELS) without affecting enzyme kinetics. The disclosed $H_2O_2$ sensor SHELS technology can detect physiologic amounts of hydrogen peroxide in aspirated human abscess with contrast ratios as high as 4-fold. Furthermore, unlike fluorescence based agents, ultrasound has a much greater depth of penetration, as high as 20 cm in the abdomen.

Unlike other spectroscopic methods for quantitating hydrogen peroxide, there is no potential for spectroscopic interference from hemoglobin using the disclosed methods employing the $H_2O_2$ sensor SHELS structures. For example, since the concentration of catSHELS can affect the signal generated, concentrated larger number of catSHELS at the site of interest could be used to detect lower amounts of hydrogen peroxide in vitro. Given that signal is seen in the physiologic human abscess samples when the local catSHELS concentration is subnanomolar, obtaining sufficient catSHELS at the site of hydrogen peroxide production is possible even in larger animals and potentially human patients. Moreover, both the exemplary SHELS and catalase are stable when dehydrated, which is an important feature when considering their use as a contrast or laboratory agent.

Detection of hydrogen peroxide with ultrasound has a wide range of potential clinical applications. For example, the exemplary catSHELS can be applied to the tip of a catheter and used at bedside to detect the presence of bacteria in biologic fluid. For example, the biodistribution and pharmacokinetic properties of SHELS may also be improved by conjugation to PEG moieties for in vivo injection. The exemplary catSHELS can provide a hydrogen peroxide sensitive contrast agent that can help in identifying abscesses in unusual locations and locations with limited percutaneous access. In some implementations, for example, bedside renal ultrasound using catSHELS as agents can allow for differentiation of renal ischemia from other causes of acute kidney injury, e.g., particularly in ICU patients who would otherwise need to be transported to the CT scanner. Similarly, a similar approach can be taken toward imaging early ischemia in the heart or even the brain using the disclosed $H_2O_2$ sensor SHELS structures. Catalase-based imaging of the heart and the brain may even be therapeutic, as free radicals contribute to the lasting damage caused by vessel ischemia. In contrast to the clinically available microbubble formulations, the microbubbles created by the disclosed technology at physiologic concentrations of $H_2O_2$ are locally produced, last only a few minutes, are more readily detected, and are much fewer in number than the clinically approved injectable microbubbles, which may correlate with greater effectivity and a more favorable side effect profile.

II.1.2. Exemplary Methods of Fabricating and Utilizing the catSHELS Hydrogen Peroxide Sensor in the Exemplary Implementations Exemplary catSHELS particles can be fabricated as described previously in FIG. 8B. In one example, catSHELS hydrogen peroxide sensors were fabricated as follows. A 50 µL template particle solution was mixed with the corresponding amount of masking particle solution to prepare the desired ratio of particle concentrations. The resultant mixture was shaken overnight and 1000 µL of anhydrous ethanol was added to the solution. To generate the silica precursor and initiate the silica growth, 1 µL of tetramethoxysilane (tetramethyl orthosilicate, TMOS) was added to the solution. The mixture was shaken overnight, and the suspended particles were collected by centrifugation (e.g., 5 min at 14000 rpm), washed with deionized water a few times and dried in vacuum overnight on a coverslide. To remove the organic compounds, a coverslide carrying the nanoparticle powder was placed over a hot plate and calcined overnight at 450° C. The calcined powder was transferred to a tube and suspended in 50 µL water and dispersed by gentle sonication. SHMS was suspended in 50 µL 80 mg/mL catalase solution in 1×PBS and incubated overnight. The solution was diluted with 1000 µL phosphate buffered saline and 50 µL 0.1% poly-L-lysine with a molecular weight of 150-300 kDa. The solution was diluted to prevent aggregation and encapsulated enzyme does not seem to leak out rapidly to cause a significant difference in loading when compared with the undiluted reaction. TMOS was added to 1 mM HCl in 74:500 volume ratio and mixed for a few minutes to make a silicic acid solution. 25 µL of the silicic acid solution was added to the above SHMS solution immediately after dilution and shaken for 1 hour in order to generate SHELS. Later, suspended SHELS were collected with centrifugation (e.g., 5 min 14000 rpm) and washed several times with water. Samples were exposed to proteinase-K enzyme overnight at a concentration of 0.1 mg/mL in 1× phosphate buffered saline (PBS) solution at 37° C. followed by removal of proteinase-K by successive washing again by 1×PBS by centrifugation (e.g., 5 min 14000 rpm).

The exemplary catSHELS were utilized in ultrasound phantoms and in vitro implementations. For example, catSHELS were concentrated to a stock solution of $1.82 \times 10^8$/µL (e.g., 500 nm), $2.8 \times 10^9$/µL (e.g., 200 nm), $2.8 \times 10^{10}$/µL (e.g., 100 nm) and diluted in 1×PBS prior to testing. The exemplary catSHELS were placed into a transfer pipette modified to contain a port that could be pinned to the back of a water bath. Either 3 mL phosphate buffered saline (PBS)+0.04 M sodium hydrate cholate (NaCH) or rabbit plasma as indicated was added to the NSCs through the port, and samples were allowed to sit for approximately five minutes. Under ultrasound operating in contrast mode (e.g., using a GE LogiqE9, 6-15 MHz linear transducer, MI<0.20, 14 frames per second), the concentration of hydrogen peroxide was increased by factors of ten (e.g., 8 µM, 80 µM, 800 µM) delivered in low volume (3 µL or 30 µL). The exemplary catSHELS were tested side by side with empty SHELS of the same geometry without catalase. Detection limits were obtained at time of study by two independent observers blinded to the identity of the tubes. The detection limit was defined as the first point at which characteristic rising bubbles were observed and was recorded at the time of the experiment. These exemplary implementations were performed in triplicate.

Regions were drawn near the bottom of the modified transfer pipette with care taken to avoid artifact associated with transducer motion. The region was averaged over three images to obtain a (pre) value and over 20 images to obtain a "post" value. The "pre" value was then subtracted from the (post) value to obtain the change in signal due to addition of nanoparticles. For saline tests, statistical significance was assessed by an unpaired 2-tailed Student's t-test.

Patient abscess fluid was obtained from the microbiology laboratory and brought to the laboratory for analysis within 72 hours of collection. At least 2 mL of abscess fluid was required for testing. Approximately $10 \times 10^{10}$ 200 nm catSHELS containing 80 mg/mL catalase was added to the side port under direct ultrasound observation (e.g., using Siemens *Sequoia*, 7 MHz, MI 0.2 or 1.9). Once microbubbles had subsided, the same number of empty control catSHELS were added to the same sample. Finally, at the end of the exemplary implementation, 3% $H_2O_2$ was added as a positive control to confirm that catSHELS were functional. Cine loops were collected and loaded into Image J for quantitation as described previously. Background sample echogenicity was assessed as the 20 frames taken immediately prior to addition of catSHELS. 50 frames subsequent to the addition of catSHELS were averaged as the post SHELS echogenicity. Once signal had returned to baseline, a second 'background' was taken immediately prior to adding the control (empty) SHELS. For example, since abscess fluid specimen were collected on different days and each was essentially an independent experiment with its own controls, aggregate statistical significance was assessed by a paired two-tailed t-test. Abscess sample collection and subsequent analysis was done in accordance with by an institutional review board.

II.2. Glucose Oxidase Encapsulation with $Ru(phen)_3^{+2}$ Doped SHELS: gRuSHELS II.2.1. Background of Diabetes and Blood Glucose Monitoring Techniques Diabetes Diabetes mellitus, or shortly diabetes, is a disease characterized by chronically raised blood glucose (sugar), due to either lack of insulin or sensitivity of cells to insulin, a pancreatic hormone. There are mainly three types of diabetes. Type 1: In patients with type 1 diabetes, pancreas cannot produce insulin requiring patients to obtain insulin externally. Type 2: In patients with type 2 diabetes, the cells in the body fail to use insulin properly, even though insulin is produced at pancreas. Gestational: This form occurs when pregnant women develop a high level of blood sugar, which may potentially lead to the development of type 2 diabetes.

The number of diabetics has been constantly increasing at epidemic rates and has been estimated to be around 366 million worldwide in 2011, which is expected to reach around 552 million by 2030. Diabetes causes long-term tissue complications affecting both small and large blood vessels including microangiopathy, atherosclerosis, increased rates of coronary heart disease, peripheral vascular disease and stroke. Most of these complications can be prevented if blood glucose levels are maintained within the physiological range of 4-8 mM and 2-30 mM, which can be achieved by frequent monitoring of blood glucose and external administration of insulin with amounts adjusted to the blood glucose level. However, maintaining normal blood glucose concentration is very difficult due to often unpredictable fluctuations, which requires a reliable continuous monitoring.

In particular, monitoring blood glucose level is very critical for prevention or early detection of hypoglycemia (low blood glucose). Hypoglycemia is a serious condition and can lead to neuroglycopenia, mild dyshoria, seizures, unconsciousness, and even permanent brain damage.

Existing Blood Glucose Monitoring Techniques

Currently, there are mainly two broad classes of monitoring techniques: point sample and continuous. Point sample techniques involve measurement of glucose from collected bodily fluids such as urine and blood. However, this kind of techniques are not convenient for the patient at the same time does not offer solution to monitoring the cases like hypoglycemia, which is serious case and can be encountered during sleep.

Continuous monitoring solutions offer more convenience for the patient as well as they are good for maintaining blood levels. There are numerous studies aiming continuous monitoring with varying invasiveness. Optical methods are considered totally non-invasive and rely on different spectroscopic methods, which mainly suffer from scattering of light reducing the signal-to-noise ratios. Scattering is also a variable effect and depends of hydration, blood flow and temperature. Nevertheless, non-glucose metabolites frequently interfere with the measurement. The heterogeneity of light-absorbing and light-scattering structures between individuals and within individuals over time requires frequent calibration bringing inconvenience to the patient making it error-prone.

Transdermal methods are minimally invasive methods that involve tissue sampling, obtaining fluids from skin using techniques such as reverse iotophoresis, sonophoresis or skin suction blister technique. However, they suffer from high error and low sensitivity. Collection of liquid for analysis takes up to 15-20 minutes and the glucose concentration in these fluids are about three orders of magnitude less compared to blood levels in blood. These techniques also suffer from variable flux of glucose across the skin, and the effects of prolonged use at one skin site prevent their successful commercialization.

Among minimally invasive sensors, amperometric enzyme electrodes are the most explored type of glucose sensors. In this kind of electrodes, enzyme glucose oxidase is immobilized on a charged electrode, and through the following reaction of glucose with glucose oxidase, hydrogen peroxide is produced: $Glucose+O_2 \rightarrow H_2O_2+gluconic$ acid. Production of hydrogen peroxide results in a change in the current flowing through the electrode, and although less common, sometimes this current change is also correlated with the consumption of oxygen.

Currently, glucose levels can be determined using existing devices based on this concept from a finger prick blood sample. These kinds of sensors are typically implemented as a fine needle or some kind of a flexible wire form with the active site located at or near the tip, which is implanted subcutaneously. Although intravascular placement is also possible, subcutaneous implantation is preferred to reduce the interference of the signal with blood clot formation. Subcutaneous glucose levels are proportional to the blood glucose concentration under most circumstances, however with a lag of several minutes. For the detection of hypoglycemia, this slight variation becomes an advantage, since drop is lagged by blood level in this case serving as an early detection for hypoglycemia.

The main problem of live monitoring sensors is that the output of the sensor is affected from in vivo conditions. This variability is associated with the interference with proteins, small molecules and inhibitors. Several approaches have been sought to reduce such interference. One of the approaches is microperfusion, to wash away inhibiting molecules or cells, hydrate tissues and generate a thin mobile aqueous film to provide a protective barrier. Another approach was to implant the sensors totally into the tissue to prevent a wound response inflammation that attracts immune cells towards the area. Artificial chemistries have also been explored such as artificial glucose receptors, which are based on attachment of the glucose reactive boronic acid moiety to a reporting unit to generate a detectable fluorescence, colorimetric or electrochemical change. However, none of the techniques have addressed all the issues required by an effective glucose sensor that would achieve the sensitivity and convenience required by the application.

II.2.2. Exemplary Devices and Methods of Glucose Oxidase Encapsulation within Ru(Phen)$_3^{+2}$ Doped SHELS: gRuSHELS An effective glucose sensor should offer quick and predictable response to changing glucose concentration while achieving a reversible and reproducible signal. A solution for a chronic disease like diabetes, cost and scalability of the synthesis and fabrication becomes important. The sensor should have a long operational lifetime in physiological conditions and should also be biocompatible and convenient for the patient. For the estimation of the adequate amount and the right timing of insulin administration, continuous monitoring throughout the day and night giving direction, magnitude, duration, frequency and potential causes of fluctuations in blood glucose levels are crucial because insulin therapy increases the risk of hypoglycemia.

For example, a comprehensive solution involves closed-loop systems, where the automated glucose administration through a pump is adjusted by the reading of the glucose sensor. Although there are some solutions, inaccuracies in glucose monitoring together with inconvenience to the patience currently limit their widespread use.

Disclosed are nanoparticle sensor devices and techniques to measure an analyte using an enzyme encapsulated in the disclosed SHELS structure. In one aspect, a nanoparticle sensor device for detecting analyte includes enzyme-encapsulated nanoparticles capable of being injected into a biological system, in which the enzyme-encapsulated nanoparticles is structured to include a shell structure including an internal layer and an external layer, the internal layer enclosing a hollow interior region and structured to form one or more holes penetrating through the internal layer, and the external layer formed of a porous material around the internal layer, an enzyme contained within the interior region of the shell structure, wherein the enzyme is smaller than the penetrating holes and larger than the pores of the shell structure and thereby incapable of passing through the external layer, wherein the enzyme is capable of a catalyzing an analyte that enters the interior region through the pores, and a fluorophore attached to the shell structure and capable of emitting an optical fluorescent signal based on the concentration of a chemical reactant or chemical product of a catalytic interaction of the enzyme and the analyte. The nanoparticle sensor device includes a light source to direct an excitation light into the biological system to cause emission of the optical fluorescent signal. The nanoparticle sensor device includes an optical detector to detect the emitted optical fluorescent signal generated by the enzyme-encapsulated nanoparticle based on catalytic interaction between the enzyme and the analyte within the shell structure.

One exemplary embodiment of the disclosed nanoparticle sensor device includes glucose oxidase (GLOX) as the encapsulated enzyme to measure glucose within Ru(phen)$_3^{+2}$ doped SHELS (gRuSHELS). The disclosed gRuSHELS provides a platform capable of in vivo glucose sensing. This platform involves encapsulation of glucose oxidase enzyme within the disclosed hollow nanoparticles of the present technology (e.g., the synthetic enzyme-loaded nanospheres), which are doped with ruthenium(II) compound, dichlorotris (1,10 phenanthroline)ruthenium(II) hydrate Ru(phen)$_3^{+2}$.

For example, the oxygen sensitive dye ruthenium(II) and ruthenium(III) compounds can be used in the measurement of glucose. The fluorescence of ruthenium(II) and ruthenium(III) compounds increases with decreasing concentration of oxygen.

Figure 12:
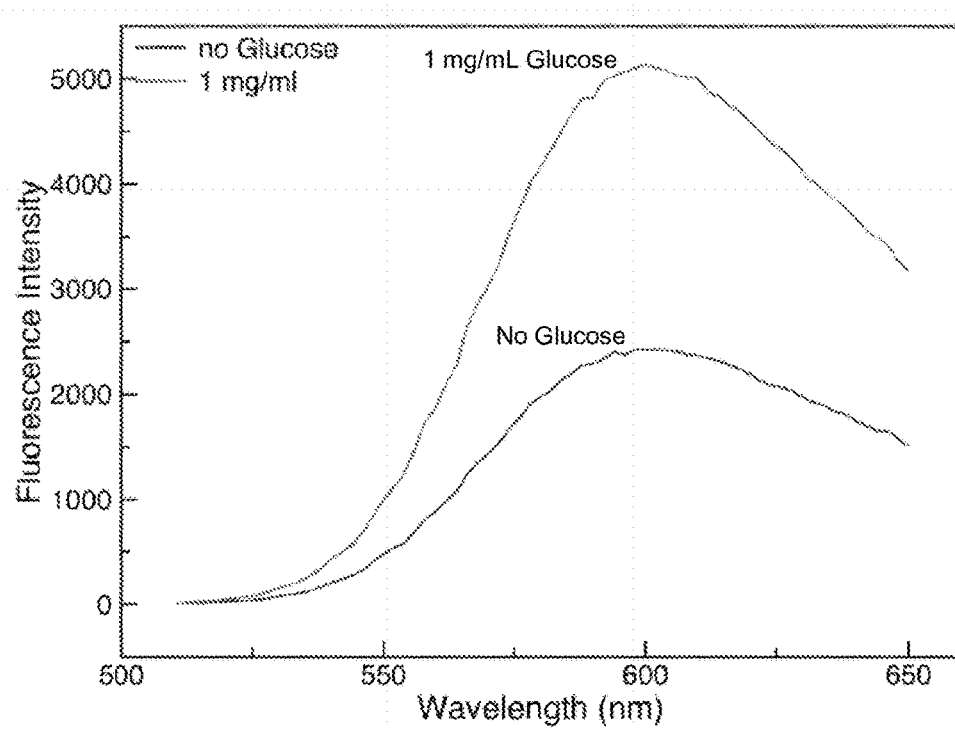
FIG. 12 shows a plot of exemplary data depicting the fluorescence spectra of $Ru(phen)_3^{+2}$ in the absence and presence of glucose with a concentration of 1 mg/mL.

When glucose diffuses into the SHELS particles, it reacts with the encapsulated glucose oxidase. As a result of the reaction, oxygen in solutions is consumed resulting in an increase in the fluorescence of Ru(phen)$_3^{+2}$. FIG. 12 shows a plot of exemplary data depicting the fluorescence spectra of Ru(phen)$_3^{+2}$ in the absence and presence of glucose with a concentration of 1 mg/mL (e.g., excitation at 456 nm).

Figure 13:
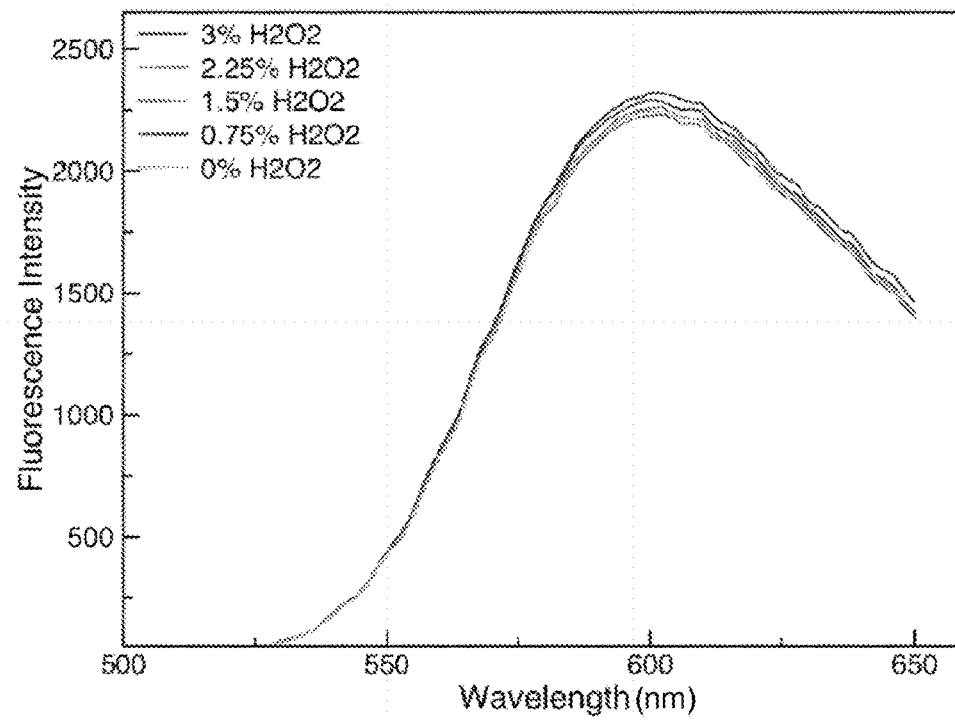
FIG. 13 shows a plot of exemplary data depicting the fluorescence spectra of $Ru(phen)_3^{+2}$ in the absence and presence of 0.75%, 1.5%, 2.25%, 3% of $H_2O_2$.

Nevertheless, the Ru(phen)$_3^{+2}$ fluorescence is not affected by H$_2$O$_2$. FIG. 13 shows a plot of exemplary data depicting the fluorescence spectra of Ru(phen)$_3^{+2}$ in the absence (0% H$_2$O$_2$) and presence of 0.75%, 1.5%, 2.25%, 3% of H$_2$O$_2$ (e.g., excitation at 456 nm). As shown in the plot of FIG. 13, the data curves follow relatively the same pattern and exhibit almost the same fluorescence intensity along the measured wavelengths. It is noted that at 600 nm wavelength, the top-most curve to the bottom-most curve is 0.75% H$_2$O$_2$, 3% H$_2$O$_2$, 1.5% H$_2$O$_2$, 0% H$_2$O$_2$, and 2.25% H$_2$O$_2$.

Figure 14:
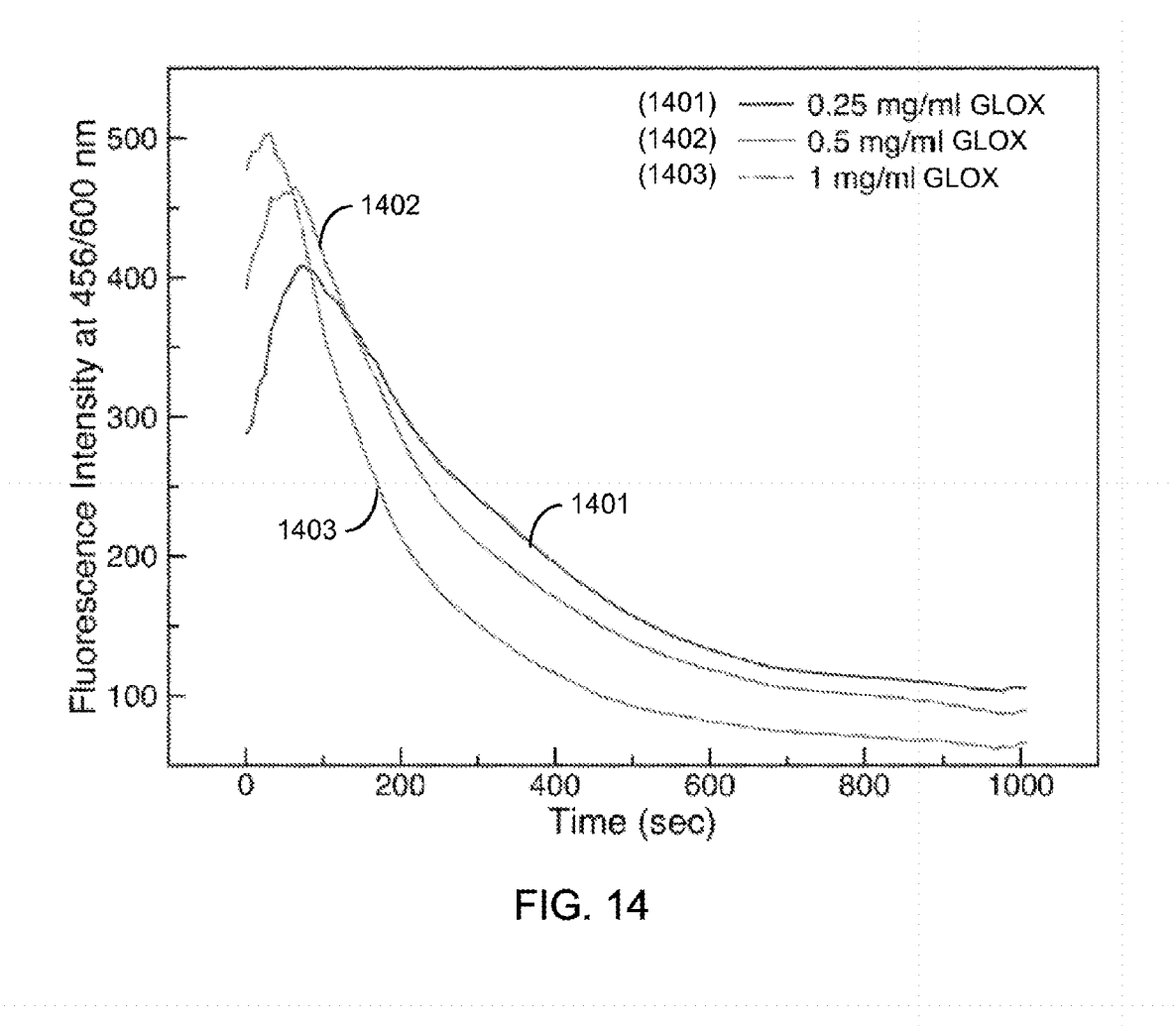
FIG. 14 shows a plot of exemplary data depicting the time evolution of the fluorescence intensity of $Ru(phen)_3^{+2}$ at 456/600 nm in the presence of glucose oxidase with 0.25, 0.5 and 1 mg/mL concentrations.

With the addition of glucose to the glucose oxidase (GLOX), the fluorescence obtained from Ru(phen)$_3^{+2}$ increases quickly reaching a maximum which indicates highest instantaneous velocity of the enzyme. Since glucose is consumed, a decaying fluorescence intensity curve is obtained. FIG. 14 shows a plot of exemplary data depicting the time evolution of the fluorescence intensity of Ru(phen)$_3^{+2}$ at 456/600 nm in the presence of glucose oxidase with a 0.25 mg/mL concentration (data curve 1401), a 0.5 mg/mL concentration (data curve 1402), and 1 mg/mL concentration (data curve 1403). Therefore, the higher the glucose oxidase concentration, the higher maximum point the intensity reaches. The higher glucose oxidase concentration is also correlated with a faster decaying curve due to faster consumption of oxygen.

II.2.3. Exemplary gRuSHELS

Figure 15:
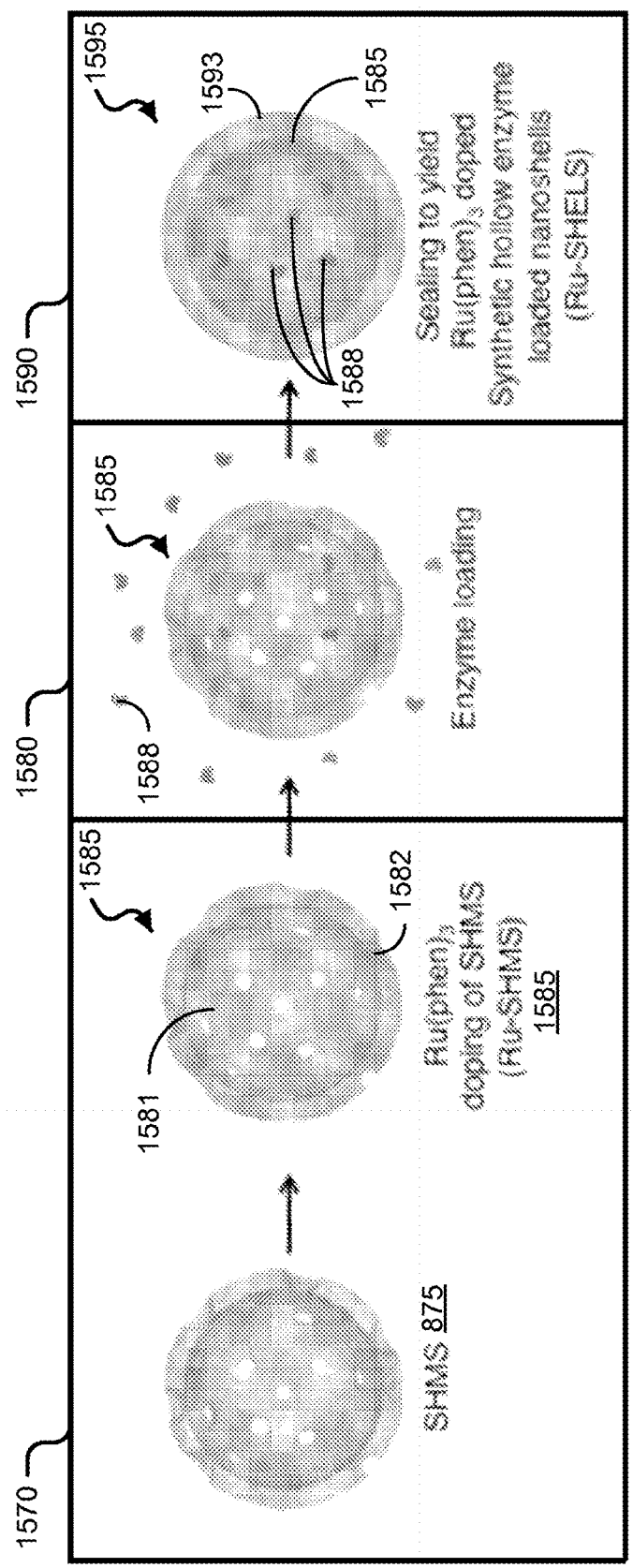
FIG. 15 shows an illustrative diagram of an exemplary method to produce exemplary gRuSHELS particles.

FIG. 15 shows an illustrative diagram of an exemplary method to produce exemplary gRuSHELS particles. The method can include acquiring synthetic hollow mesoporous shells (SHMS) particles 875. For example, the SHMS particles 875 can be acquired by implementing the processes 850, 860, and 870 to produce the synthetic hollow mesoporous shells particles, as previously described in FIG. 8D. For example, in implementations of the process 850, the template particles 851 can include amine-functionalized polystyrene nanoparticles, and the nanomasking particles 852 can include carboxy-functionalized polystyrene nanoparticles, in which the template particles 851 and nanomasking particles 852 are mixed in solution. For example, in implementations of the process 860, the coating layer 863 can include porous silica, in which sol-gel reagents are added to the solutions containing the nanomask structures 855, and a silica polycondensation reaction occurs on the template surface while nanomasking particles 852 block the reaction at the point of contact with the template particles 851. For example, in implementations of the process 870, the exemplary polymer template particles 851 and nanomasking particles 852 can be removed by calcination or dissolution to generate the SHMS structure 875.

As shown in the illustrative diagram of FIG. 15, the method included a process 1570 to dope the shell structure of the SHMS particles 875 with Ru(phen)$_3^{+2}$ to produce Ru-SHMS particles 1585. In some implementations of the process 1570, for example, the SHMS particles 875 are incubated in Ru(phen)$_3^{+2}$ solution followed by sol-gel reaction and removal of reactants, which yields exemplary Ru-SHMS particles 1585. For example, the SHMS particles 875 can be suspended in Ru(phen)$_3^{+2}$ solution followed by addition of TMOS to the solution and reacted overnight. Later, inbound Ru(phen)$_3^{+2}$ can be washed out by ethanol followed by addition of more TMOS, to initiate further sol-gel reactions. Later unreacted regents can be washed away, which yields exemplary Ru-SHMS particles 1585.

The method includes a process 1580 to load enzymes 1588, e.g., such as glucose oxidase, into the hollow interior region of the Ru-SHMS particle 1585 through the mesopores of the SHMS's shell structure. In some implementations of the process 1580, for example, a solution of the enzyme glucose oxidase 1588 can be added to a solution of the Ru-SHMS particles 1585. The process 1580 can be implemented by diffusion of the enzymes 1588 into the hollow, mesoporous shell structure of the Ru-SHMS particles through the mesopores (e.g., >5 nm), and/or by electrophoretic forces that cause the enzymes 1588 to enter the hollow interior region of Ru-SHMS particles 1585. For example, a high concentration of the enzyme glucose oxidase (e.g., 100-200 mg/ml) can be added to the Ru-SHMS suspension and diffuses into the Ru-SHMS particles 1585. Also for example, the interior enzyme concentration can be equilibrated with exterior concentration.

The method includes a process 1590 to form an outer coating layer 1593 on the Ru-SHMS particles 1585 encapsulating the enzymes 1588 to produce a doped SHELS structure 1595, e.g., the exemplary gRuSHELS particles. For example, the external coating layer 1593 can include nanoporous silica or other nanoporous material, e.g., sealing the exemplary glucose oxidase enzymes 1588 within the gRuSHELS particle 1595. In an example using nanoporous silica for the external coating layer 1593, since the surface of the Ru-SHMS structures 1585 is negatively charged due to SiO— groups, a positively charged polymer, e.g., such as poly-l-lysine, is added to adsorb to the particles' surface and change the surface charge to positive. For example, the addition of PLL can cover the mesopores preventing the escape of the enzymes trapping them in the hollow interior. Then, TMOS can be added to grow new silica on the surface and close the mesopores of Ru-SHMS particles 1585 converting them to doped SHELS structure 1595. This reaction occurs in near neutral buffer conditions and does not damage the enzyme. Once the mesopores are closed, the load is encapsulated within SHELS and cannot escape. However, the load can still interact with small molecules in the surrounding environment via diffusion through nanopores.

For example, the doped SHELS particles produced by the method shown in FIG. 15 is capable of providing a high loading efficiency and durability, which is required for successful in vivo implementations with a large degree of control of the effects of the particle system on the biological environment. Exemplary implementations of the doped SHELS particles were performed using silica as a material used in the SHELS structures, glucose oxidase as the encapsulated enzymes, and $Ru(phen)_3^{+2}$ as the doping agent. For example, silica provides a biocompatible and safe material for such in vivo applications with long-enough degradation, a porous nature allowing high specific surface area for the $Ru(phen)_3^{+2}$ doping, thermal and mechanical stability, low density and nanoporosity that would allow diffusion of small molecules, e.g., glucose and oxygen, for diffusion through the shell.

Figure 16:
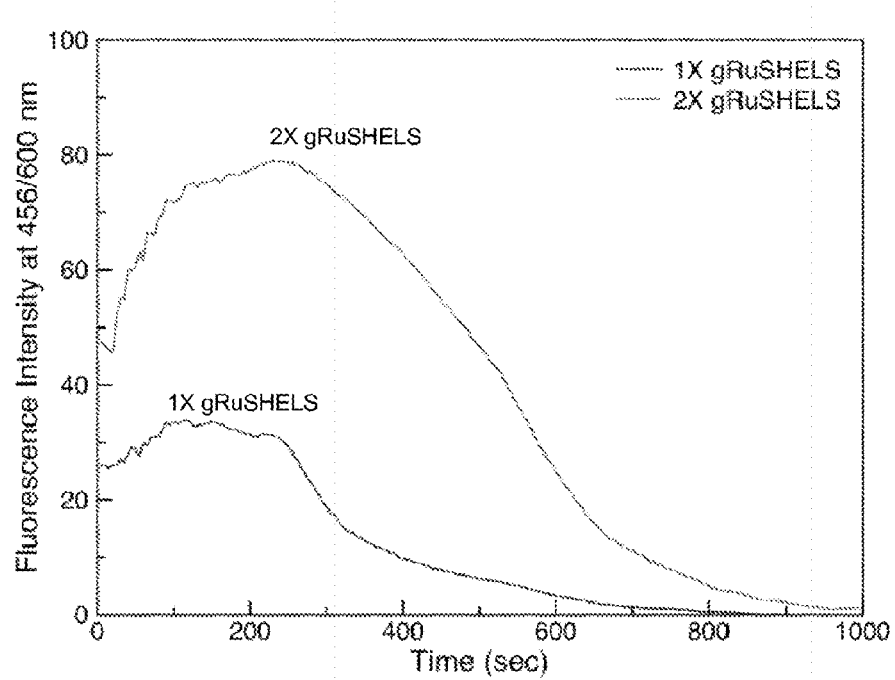
FIG. 16 shows a plot of exemplary data depicting the time evolution of the fluorescence intensity of gRuSHELS at 456/600 nm with concentrations of $1 \times 10^{12}$ pts/mL (1×) and $2 \times 10^{12}$ pts/mL (2×).

When the exemplary shell structures are doped with $Ru(phen)_3^{+2}$ and glucose oxidase (GLOX) is encapsulated within the doped SHELS particles, the behavior of particles can resemble free $Ru(phen)_3^{+2}$. FIG. 16 shows a plot of exemplary data depicting the time evolution of the fluorescence intensity of gRuSHELS at 456/600 nm with concentrations of $1\times10^{12}$ pts/mL (1x) and $2\times10^{12}$ pts/mL (2x). When number of particles has changed, both amount of $Ru(phen)_3^{+2}$ and the number of enzymes also change. For example, since there are more GLOX, the consumption rate of oxygen is also increased when the number of particles is doubled, similar to the behavior of free $Ru(phen)_3^{+2}$.

Figure 17:
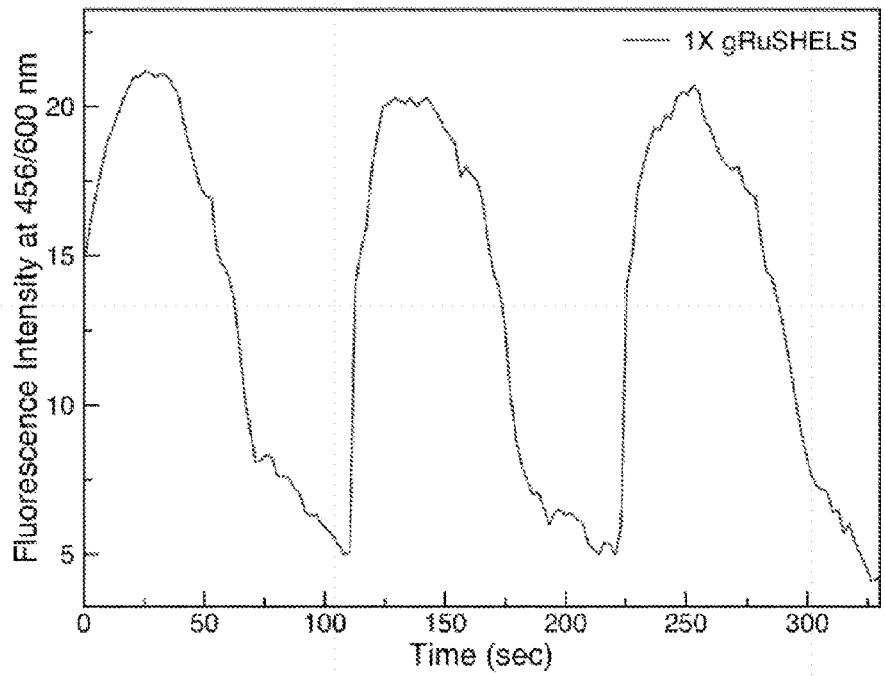
FIG. 17 shows a plot of exemplary data depicting the time evolution of the fluorescence intensity of gRuSHELS at 456/600 nm with repeated additions of glucose with a final concentration of 1 mg/mL.

It is noted that for in vivo conditions the amount of glucose fluctuates. Therefore, to determine whether gRuSHELS responds to evolving glucose concentration, repeated injections of glucose into solution were performed following its consumption. FIG. 17 shows a plot of exemplary data depicting the time evolution of the fluorescence intensity of gRuSHELS at 456/600 nm with repeated additions of glucose with a final concentration of 1 mg/mL. For example, after initial administration of glucose into a solution of gRuSHELS with a concentration of $1\times10^{12}$ pts/mL, the glucose is depleted in 2 minutes. Serial administrations of glucose at 2 and 4 minutes with a final concentration of 1 mg/mL resulted in similar curves indicating reproducibility of the response of gRuSHELS to changing glucose concentration.

The disclosed gRuSHELS particles can be included in a nanoparticle sensor device including the exemplary gRuSHELS and an external fluorescence detector. In some examples, the fluorescence detector can be included in an attachable patch or band (e.g., an armband) worn by a subject, e.g., including a human patient or an animal used in a clinical trial or other research study. The fluorescence detector can allow frequent and/or automated measurement of the glucose level externally by detecting the optical fluorescence signals generated from the gRuSHELS (e.g., excited $Ru(phen)_3^{+2}$), e.g., through the skin and/or other tissue of the subject. For example, the nanoparticle sensor device can be portable. For example, the attachable patch or band can include a flexible material, e.g., such as a fabric or polymer such as polydimethylsiloxane (PDMS).

Figure 18:
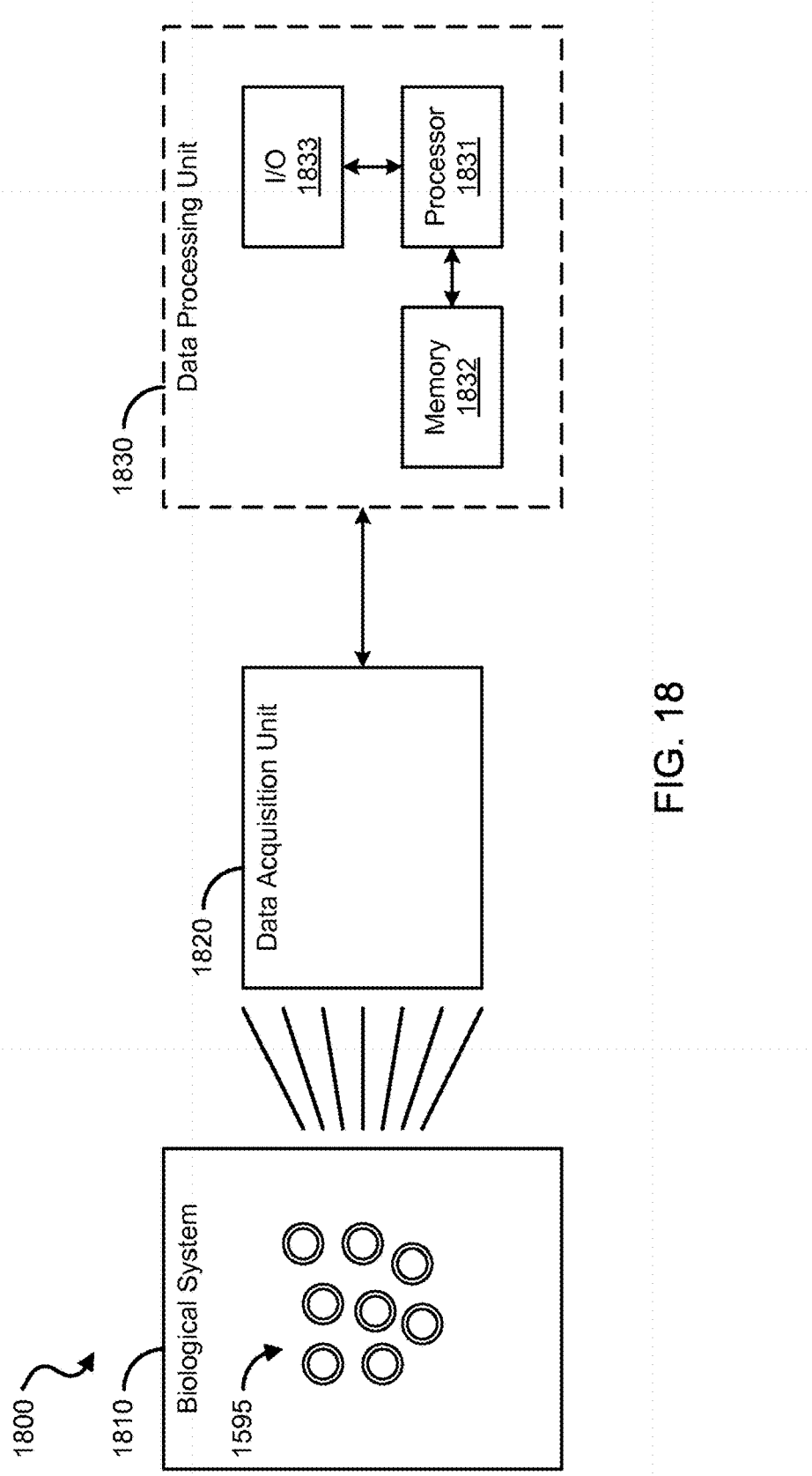
FIG. 18 shows a block diagram of an exemplary enzyme-encapsulated nanoparticle sensor device to measure an analyte in a biological system.

FIG. 18 shows a block diagram of an exemplary enzyme-encapsulated nanoparticle sensor device 1800 to measure an analyte in a biological system. The device 1800 includes SHELS particles of the disclosed technology that includes a light-emitting molecule or entity attached to or enclosed within the shell structure of the SHELS particle, in which the SHELS particle is deployed in a biological system 1810. For example, the SHELS particles of the device 1800 can include SHELS particles 100, 700, 800, 1595, or other nanoparticle structures described in this patent document. For example, the biological system 1810 can include a human subject, non-human animal subject, or other living organism in vivo, or cells of any living organism in vitro. The device 1800 includes an optical signal acquisition unit 1820 to detect an optical signal generated by the SHELS particles based on interaction with an analyte and the enzyme contained within the SHELS structure, in which the analyte is a biological and/or chemical entity capable of being catalyzed by the encapsulated enzyme within the SHELS structure. In some implementations, for example, the optical signal acquisition unit 1820 can include an optical transducer to convert the detected optical signal into an electrical signal and/or signal processing circuits to condition the detected signal. In some implementations, for example, the optical signal acquisition unit 1820 can include an excitation light source and an optical detector to sense the emitted fluorescence from the reporter dye. In the exemplary case of ruthenium, the wavelength of the excitation light source can be configured to be 450-550 nm while the emission wavelength can be around 600 nm. In some implementations, for example, the optical detector can include an image sensor or fluorometer to capture an image that reflects the fluorescence of the fluorescent SHELS particles molecules, and/or a diode, CCCD, or CMOS arrays, which can analyze spectral information. In some implementations, for example, the optical detector can include a spectrometer, photodetector, photo multiplier tube, etc.

In some implementations to improve the sensitivity, for example, ratiometric measurement can be performed, in which case, there will be an additional dye that is not sensitive to the analyte. The ratio the both dyes are fixed in a range in the absence of the analyte. The analyte affects the fluorescence intensity of the reporter dye while not affecting the other dye, therefore, changing the fluorescence emission intensity ratio. Based on a standard curve, one can quantify the analyte concentration using the change in intensity ratio of the both dyes exited by a given light source. The second dye can be a dye that can be excited by the same source that excites the reporter dye, although it is emission wavelength is different from the reporter dye. Or it can be excited by a different wavelength using a separate excitation source.

In some implementations of the nanoparticle sensor device, for example, the device 1800 includes a data processing unit 1830 that can be in wireless or wired data communications with the data acquisition unit 1820 to process the detected optical signal. For example, the wired or wireless communication between the data processing unit 1830 and the data acquisition unit 1820 can include Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces.

The data processing unit 1830 can include a processor 1831 to process data and a memory unit 1832 in communication with the processor 1831 to store data. For example, the processor 1831 can include a central processing unit (CPU) or a microcontroller unit (MCU). For example, the memory unit 1832 can store processor-executable code, which when executed by the processor 1831, configures the data processing unit 1830 to perform various operations, such as receiving information, commands, and/or data, processing information and data, and transmitting or providing information/data to another entity or to a user. In some implementations, the data processing unit 1830 can be implemented by a remote communications device (e.g., such as a smartphone, tablet, or wearable computer communications device such as a smart-watch, etc.), a remote computer and/or a computer system in a communication network accessible via the Internet (referred to as 'the cloud') that includes one or more computational processing devices (e.g., servers in the cloud).

In some implementations, for example, the nanoparticle sensor device 1800 can measure glucose, in vivo, in a living organism such as a human subject or non-human animal, or in vitro in any biological organism. In such exemplary implementations, the device 1800 includes gRuSHELS particles 1595 deployed in the biological system 1810. For example, the biological system 1810 can include a human subject, non-human animal subject, or other living organism in vivo, or cells of any living organism in vitro. The optical signal acquisition unit 1820 is operable to detect a fluorescent optical signal generated by the gRuSHELS particles 1595 based on interaction with glucose catalyzed by the encapsulated glucose oxidase enzyme within the gRuSHELS particles 1595. For example, the oxygen-sensitive fluorophore $Ru(phen)_3^{+2}$ emits a fluorescent signal based on a reduction in oxygen concentration as glucose is catalyzed by the encapsulated glucose oxidase within the particles 1595.

For example, silica and $Ru(phen)_3^{+2}$ are considered to be safe within required dose ranges. The exemplary gRuSHELS can be configured to degrade slowly and prevent any short term or long term toxicity, e.g., enabling use for chronic diabetes monitoring and/or research studies. Additionally, the exemplary SHELS structures are capable to achieve high enzyme entrapment capacity, and at the same time high $Ru(phen)_3^{+2}$ doping efficiency due to their negative surface charge. Nanoporous silica provides high surface area for small molecule diffusion, and hollow structure generates low toxicity.

In some implementations of the gRuSHELS particles, for example, an additional dye that is not sensitive to oxygen and hydrogen peroxide concentration, e.g., preferentially at near infrared range, can also be doped into the shell structure to allow a ratio-metric measurement in order to increase accuracy. Also, in some implementations of the portable nanoparticle sensor device, for example, the detected fluorescent signal can also be coupled to an automated insulin pump, thus, offering a complete solution for diabetes.

III. Exemplary Advantages of the Disclosed Enzyme-Encapsulated Nanoparticles

The disclosed technology provides a low cost nanoparticle platform that can be administered subcutaneously with minimal burden to the patient in a variety of biomedical therapeutic and diagnostic applications. The disclosed nanoparticle platform can encapsulate functional biomolecules, such as enzymes, which act on small molecule substrates in in vivo or in vitro biological environments, where the small molecule substrates can freely diffuse in and out through the nanoparticle's pores. For example, exemplary SHELS devices can be manufactured in large quantities with sizes and characteristics that can be tightly controlled for maximizing entrapment capacity and enzymatic activity. Exemplary implementations demonstrated exemplary results showing that the porous shells effectively encapsulate the enzyme payload while preserving its activity. The shell structure also protects the enzyme payload from specific and nonspecific interference from large biomolecules in vivo and/or in vitro. In addition, surface modifications of SHELS can be able to enhance circulation and targeting in vivo without the need for modification of the enzyme payload. Since nanomasking provides flexible fabrication of SHELS with control of particle dimensions and permeability, SHELS can be tailored and optimized for specific loads and substrates. Moreover, utilization of the hollow nanostructure reduces the amount of carrier material introduced into the body. It has also been described that the disclosed SHELS technology prevents neutralization of foreign enzymes by antibodies in vivo and can be used to achieve systemic effects even while they remain localized. Additionally, for example, the exemplary SHELS fabrication techniques can be applicable to many other materials. Also, for example, in addition to the described examples of biomedical (e.g., diagnostic and therapeutic) applications, the disclosed SHELS devices can be made of different materials and can be used in a variety of applications including non-biomedical ones.

In exemplary biomedical applications, for an enzyme delivery technology to succeed in the clinic, multiple requirements such as stability, immunoprotection, sustained activity, low toxicity, sufficient target retention and broad applicability should be met. The disclosed SHELS technology can achieve all of these requirements and are employable in clinical applications. The disclosed SHELS technology are functional in a variety of biomedical and environmental applications, and exhibit high loading capacity, versatility, low toxicity profile, scalability and easy functionalization ability. In some examples, for systemic delivery applications, the surface of SHELS can be further functionalized for targeting and improved circulation half-life thereby eliminating the need for chemical modification of the enzymatic payload. Under these conditions, for example, stealth SHELS can allow continuous and controlled access of the substrate to the native enzyme cargo, which makes this a promising therapeutic platform for treating metastatic disease. In addition, for example, SHELS can be applicable to in vivo medical diagnostics and monitoring. Enzyme-prodrug therapy, enzymatic depletion of tumor nutrients, and enzyme replacement therapy are among some of the many exemplary applications for implementation of the disclosed technology.

EXAMPLES

The following examples are illustrative of several embodiments of the present technology. Other exemplary embodiments of the present technology may be presented prior to the following listed examples, or after the following listed examples.

In an example of the present technology (example 1), a nanoparticle for catalyzing an analyte includes a shell structure including an internal layer and an external layer, the internal layer structured to enclose a hollow interior region and include one or more holes penetrating through the internal layer, and the external layer formed of a porous material around the internal layer; an enzyme contained within the interior region of the shell structure, the enzyme having entered the shell structure through the one or more holes and is incapable of passing through the external layer; and a biochemical cofactor corresponding to the enzyme, in which the biochemical enzyme is contained in the interior region and capable of binding to the enzyme, in which the pores are of a size that prevents the enzyme to pass through the pores while permitting an analyte smaller than the pore size to pass through the pores, in which the enzyme is capable of catalyzing the analyte within the interior region.

Example 2 includes the nanoparticle as in example 1, in which the enzyme includes an apoenzyme, in which the cofactor binds to the apoenzyme to form a holoenzyme capable of catalyzing the analyte.

Example 3 includes the nanoparticle as in example 1, further including a charged material layer formed in the holes to provide an electrostatic force to further contain the biochemical cofactor in the interior region.

Example 4 includes the nanoparticle as in example 1, in which the enzyme contained within the shell structure includes methioninase, the cofactor includes pyroxidal-5'-phosphate (PLP), and the analyte includes methionine.

Example 5 includes the nanoparticle as in example 4, in which the nanoparticle is capable of being deployed to a biological tissue within an organism through the blood stream, in which the shell structure inhibits antibodies and other substances that degrade methioninase from entering the interior region while permitting the methionine to enter into the interior region through the pores and catalytically interact with the contained methioninase.

Example 6 includes the nanoparticle as in example 4, in which the nanoparticle is configured to increase the catalysis of methionine based on reduced loss of the PLP in the blood stream.

Example 7 includes the nanoparticle as in example 1, further including a ligand molecule conjugated to the shell structure, the ligand molecule having an affinity to a receptor molecule of the biological tissue to attract the shell structure to the biological tissue.

Example 8 includes the nanoparticle as in example 1, in which the nanoparticle is configured to a size capable of in vivo injection including in a range between 100 nm to 500 nm.

Example 9 includes the nanoparticle as in example 1, further including a paramagnetic material in the shell structure.

Example 10 includes the nanoparticle as in example 1, in which the biological system includes a living organism including a non-human animal or a human being.

In an example of the present technology (example 11), an ultrasound-interactive nanoparticle sensor device for detecting reactive oxidative species includes a nanoparticle structured to include a shell structure including an internal layer and an external layer, the internal layer enclosing a hollow interior region and including one or more holes penetrating through the internal layer, and the external layer formed of a porous material around the internal layer; and an enzyme encapsulated within the interior region of the shell structure, in which the enzyme is smaller than the penetrating holes and larger than the pores of the shell structure, thereby incapable of passing through the external layer, and in which the enzyme is capable of catalyzing a reactive oxidative species (ROS) to decompose and yield oxygen, in which the enzyme-encapsulated nanoparticle is configured to produce microbubbles from the oxygen produced by decomposition of the ROS within the nanoparticles, and in which the produced microbubbles are detectable by ultrasonic acoustic energy provided by an ultrasonic acoustic energy device when the enzyme-encapsulated nanoparticle is deployed in a biological system and the ultrasonic acoustic energy is directed at a particular region of the biological system where the nanoparticles are located, and the produced microbubbles cause a change in a returned acoustic waveform carrying information on the microbubbles formed in the particular region and capable of being received by the ultrasonic acoustic energy device.

Example 12 includes the device as in example 11, further including nanoscale structures protruding from the interior surface of the internal layer toward the hollow interior region, in which the nanoscale structures initiate cavitation of oxygen bubbles based on the directed ultrasonic acoustic energy device.

Example 13 includes the device as in example 11, in which the shell structure is configured to prevent proteases from the biological system that are chemically interactive with the enzyme from entering the interior region.

Example 14 includes the device as in example 11, in which the ROS includes hydrogen peroxide.

Example 15 includes the device as in example 11, in which the enzyme includes catalase.

Example 16 includes the device as in example 11, in which the external layer of the nanoparticle includes a nanoporous surface to provide a nucleation site for oxygen microbubble formation.

Example 17 includes the device as in example 11, in which the biological system includes a living organism, and the particular region includes a depth up to 20 cm in a biological tissue of the living organism.

Example 18 includes the device as in example 17, in which the directed ultrasonic acoustic energy is pulsed to elicit nonlinear oscillations of the microbubbles affecting the returned acoustic energy, thereby allowing detection of the ROS in the biological tissue.

Example 19 includes the device as in example 17, in which the nanoparticle includes a ligand molecule conjugated to the shell structure, the ligand molecule having an affinity to a receptor molecule of the biological tissue to attract the shell structure to the biological tissue.

Example 20 includes the device as in example 11, in which the nanoparticle is configured to a size capable of in vivo injection including in a range between 100 nm to 500 nm.

Example 21 includes the device as in example 11, in which the nanoparticle includes a paramagnetic material in the shell structure.

Example 22 includes the device as in example 11, in which the biological system includes a living organism including a non-human animal or a human being.

In an example of the present technology (example 23), a nanoparticle sensor device for detecting analyte includes enzyme-encapsulated nanoparticles capable of being injected into a biological system, in which the enzyme-encapsulated nanoparticles is structured to include a shell structure including an internal layer and an external layer, the internal layer enclosing a hollow interior region and structured to form one or more holes penetrating through the internal layer, and the external layer formed of a porous material around the internal layer, an enzyme contained within the interior region of the shell structure, wherein the enzyme is smaller than the penetrating holes and larger than the pores of the shell structure and thereby incapable of passing through the external layer, wherein the enzyme is capable of a catalyzing an analyte that enters the interior region through the pores, and a fluorophore attached to the shell structure and capable of emitting an optical fluorescent signal based on the concentration of a chemical reactant or chemical product of a catalytic interaction of the enzyme and the analyte. The nanoparticle sensor device includes a light source to direct an excitation light into the biological system to cause emission of the optical fluorescent signal. The nanoparticle sensor device includes an optical detector to detect the emitted optical fluorescent signal generated by the enzyme-encapsulated nanoparticle based on catalytic interaction between the enzyme and the analyte within the shell structure.

Example 24 includes the device as in example 23, in which the enzyme includes glucose oxidase (GLOX), the analyte includes glucose, and the fluorophore includes an oxygen-sensitive fluorophore, e.g., including a ruthenium (II) or ruthenium(III) compound.

Example 25 includes the device as in example 24, in which the wavelength of the excitation light includes 450-550 nm.

Example 26 includes the device as in example 23, further including a data processing unit in data communication with the optical detector to process the detected optical fluorescent signal as data and determine a concentration of the analyte in the biological system.

Example 27 includes the device as in example 26, in which the data processing unit is included in a mobile communication device including at least one of a smartphone, a tablet, or a wearable communication device.

Example 28 includes the device as in example 23, in which the enzyme-encapsulated nanoparticle includes a ligand molecule conjugated to the shell structure, the ligand molecule having an affinity to a receptor molecule of the biological system to attract the shell structure to the biological system.

Example 29 includes the device as in example 23, in which the enzyme-encapsulated nanoparticle is configured to a size capable of in vivo injection including in a range between 100 nm to 500 nm.

Example 30 includes the device as in example 23, in which the enzyme-encapsulated nanoparticle includes a paramagnetic material in the shell structure.

Example 31 includes the device as in example 23, in which the biological system includes a living organism including a non-human animal or a human being.

Example 32 includes the device as in example 31, further including a patch or a band attachable to the living organism and including the optical detector to allow frequent measurement of the emitted optical fluorescent signal through the skin of the living organism.

In an example of the present technology (example 33), a nanoparticle for encapsulating a biomolecule includes a shell structure including an internal layer and an external layer, the internal layer structured to enclose a hollow interior region and include one or more holes penetrating through the internal layer, and the external layer formed of a porous material around the internal layer; and an enzyme contained within the interior region of the shell structure, the enzyme having entered the shell structure through the one or more holes and is incapable of passing through the external layer, in which the pores are of a size that prevents the enzyme to pass through the pores while permitting substances smaller than the pore size to pass through the pores.

Example 34 includes the nanoparticle as in example 33, in which the nanoparticle is configured to have a diameter in a range between 100 nm to 500 nm.

Example 35 includes the nanoparticle as in example 33, in which at least some pores of the external layer penetrate the external layer and align with the penetrating holes of the internal layer.

Example 36 includes the nanoparticle as in example 33, in which the external layer is formed of nanoporous silica.

Example 37 includes the nanoparticle as in example 36, in which the internal layer is formed of nanoporous silica.

Example 38 includes the nanoparticle as in example 33, in which the enzyme contained within the shell structure includes a catalase enzyme.

Example 39 includes the nanoparticle as in example 38, in which the nanoparticle is configured to detect hydrogen peroxide in a fluid via an catalytic interaction between the catalase enzyme and the hydrogen peroxide, in which the shell structure of the nanoparticle provides a nucleation site for formation of oxygen microbubbles as a result of the reaction.

Example 40 includes the nanoparticle as in example 33, in which the enzyme contained within the shell structure includes an enzyme in the L-asparaginase enzyme family.

Example 41 includes the nanoparticle as in example 40, further including a ligand molecule conjugated to the shell structure, the ligand molecule having an affinity to a receptor molecule found on a target structure to attract and bind the shell structure to the target structure.

Example 42 includes the nanoparticle as in example 41, in which the target structure is a living tissue within an organism, the shell structure bound to the living tissue.

Example 43 includes the nanoparticle as in example 42, in which the living tissue is a tumor.

Example 44 includes the nanoparticle as in example 33, in which the enzyme contained within the shell structure includes methioninase.

Example 45 includes the nanoparticle as in example 44, in which the nanoparticle is configured to deliver the methioninase to a tumor in a living tissue within an organism, in which the shell structure inhibits antibodies and other substances that degrade methioninase from entering the interior region.

Example 46 includes the nanoparticle as in example 33, in which the enzyme contained within the shell structure includes uricase.

Example 47 includes the nanoparticle as in example 46, in which the nanoparticle is configured to convert endogenous plasma uric acid to hydrogen peroxide at a diseased tissue site to cause cell death in at least some of the cells of the diseased tissue.

Implementations of the subject matter and the functional operations of the data processing units described in this patent document can be implemented in various systems, digital electronic circuitry, or in computer software, firmware, or hardware, including the structures disclosed in this specification and their structural equivalents, or in combinations of one or more of them. Implementations of such data processing subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A nanoparticle sensor device for detecting an analyte, comprising:
    enzyme-encapsulated nanoparticles capable of being injected into a living organism including a non-human animal or a human being, the enzyme-encapsulated nanoparticles structured to include:
        a shell structure including an internal layer and an external layer, the internal layer enclosing a hollow interior region and structured to form one or more holes penetrating through the internal layer, and the external layer formed of a porous material arranged around the internal layer,
        an enzyme contained within the interior region of the shell structure, wherein the internal layer is structured to form the one or more holes sized to allow the enzyme to pass through the internal layer, wherein the external layer is structured to prevent the enzyme from passing through the external layer but allow an analyte smaller than the enzyme to pass through the external layer, and wherein the enzyme is structured to catalyze the analyte that enters the interior region, and a fluorophore attached to the shell structure and configured to emit an optical fluorescent signal based at least on the concentration of a chemical reactant or chemical product of a catalytic interaction of at least the enzyme and the analyte;

a light source to direct an excitation light through the skin of the living organism to cause emission of the optical fluorescent signal by the enzyme-encapsulated nanoparticles when located in a subcutaneous region of the living organism; and an optical detector to detect the emitted optical fluorescent signal generated by the enzyme-encapsulated nanoparticle based on catalytic interaction between the enzyme and the analyte within the shell structure.

2. The device as in claim 1, wherein the enzyme includes glucose oxidase (GLOX), the analyte includes glucose, and the fluorophore includes an oxygen-sensitive fluorophore including a ruthenium(II) or ruthenium(III) compound.

3. The device as in claim 2, wherein the wavelength of the excitation light includes 450-550 nm.

4. The device as in claim 1, further comprising:
a data processing unit in data communication with the optical detector to process the detected optical fluorescent signal as data and determine a concentration of the analyte in the living organism.

5. The device as in claim 4, wherein the data processing unit is included in a mobile communication device including at least one of a smartphone, a tablet, or a wearable communication device.

6. The device as in claim 1, wherein the enzyme-encapsulated nanoparticle includes a ligand molecule conjugated to the shell structure, the ligand molecule having an affinity to a receptor molecule of the living organism to attract the shell structure to the living organism.

7. The device as in claim 1, wherein the enzyme-encapsulated nanoparticle is configured to a size capable of in vivo injection including in a range between 100 nm to 500 nm.

8. The device as in claim 1, wherein the enzyme-encapsulated nanoparticle includes a paramagnetic material in the shell structure.

9. The device as in claim 1, further comprising:
a patch or a band attachable to the living organism and including the optical detector to allow frequent measurement of the emitted optical fluorescent signal from the subcutaneous region through the skin of the living organism.

10. The device as in claim 9, wherein the patch or band includes a flexible material including a fabric or polymer.

11. A nanoparticle sensor device for detecting an analyte, comprising:
enzyme-encapsulated nanoparticles capable of being injected into a biological system, the enzyme-encapsulated nanoparticles structured to include:
a shell structure including an internal layer and an external layer, the internal layer enclosing a hollow interior region and structured to form one or more holes penetrating through the internal layer, and the external layer formed of a porous material arranged around the internal layer, glucose oxidase (GLOX) contained within the interior region of the shell structure, wherein the internal layer is structured to form the one or more holes sized to allow the GLOX to pass through the internal layer, wherein the external layer is structured to prevent the GLOX from passing through the external layer but allow glucose to pass through the external layer, and wherein the GLOX is structured to catalyze the glucose that enters the interior region, and a fluorophore including a ruthenium(II) or ruthenium(III) compound attached to the shell structure and configured to emit an optical fluorescent signal based at least on the concentration of a chemical reactant or chemical product of a catalytic interaction of at least the GLOX and the glucose;

a light source to direct an excitation light to a region under an outer surface of the biological system to cause emission of the optical fluorescent signal by the enzyme-encapsulated nanoparticles when located in the region under the outer surface of the biological system, wherein the wavelength of the excitation light includes 450-550 nm; and an optical detector to detect the emitted optical fluorescent signal generated by the enzyme-encapsulated nanoparticle based on catalytic interaction between the GLOX and the glucose within the shell structure.

12. The device as in claim 11, further comprising:
a data processing unit in data communication with the optical detector to process the detected optical fluorescent signal as data and determine a concentration of the glucose in the biological system.

13. The device as in claim 12, wherein the data processing unit is included in a mobile communication device including at least one of a smartphone, a tablet, or a wearable communication device.

14. The device as in claim 11, wherein the enzyme-encapsulated nanoparticle includes a ligand molecule conjugated to the shell structure, the ligand molecule having an affinity to a receptor molecule of the biological system to attract the shell structure to the biological system.

15. The device as in claim 11, wherein the enzyme-encapsulated nanoparticle is configured to a size capable of in vivo injection including in a range between 100 nm to 500 nm.

16. The device as in claim 11, wherein the enzyme-encapsulated nanoparticle includes a paramagnetic material in the shell structure.

17. The device as in claim 11, wherein the enzyme-encapsulated nanoparticles include a concentration of the GLOX in a range between 100 to 200 mg/mL.

18. The device as in claim 11, further comprising:
a patch or a band attachable to the living organism and including the optical detector to allow frequent measurement of the emitted optical fluorescent signal through the skin of the living organism.

19. The device as in claim 18, wherein the patch or band includes a flexible material including a fabric or polymer.

20. The device as in claim 11, wherein the biological system includes a living organism including a non-human animal or a human being.

* * * * *